United States Patent
Cox et al.

(10) Patent No.: US 9,611,470 B2
(45) Date of Patent: Apr. 4, 2017

(54) REF NUCLEASE FOR SITE-SPECIFIC REF-MEDIATED DNA CLEAVAGE

(71) Applicant: Wisconsin Alumni Research Foundation, Madison, WI (US)

(72) Inventors: Michael Matthew Cox, Oregon, WI (US); Angela Jo Gruber, Madison, WI (US); Tayla Maria Olsen, Madison, WA (US)

(*) Notice: Subject to any disclaimer, the term of this patent is extended or adjusted under 35 U.S.C. 154(b) by 79 days.

(21) Appl. No.: 14/336,828

(22) Filed: Jul. 21, 2014

(65) Prior Publication Data

US 2015/0023943 A1 Jan. 22, 2015

Related U.S. Application Data

(60) Provisional application No. 61/856,667, filed on Jul. 20, 2013.

(51) Int. Cl.
| | | |
|---|---|---|
| C12N 15/01 | (2006.01) | |
| C12N 9/22 | (2006.01) | |
| C07K 14/005 | (2006.01) | |

(52) U.S. Cl.
CPC ............ *C12N 15/01* (2013.01); *C07K 14/005* (2013.01); *C12N 9/22* (2013.01)

(58) Field of Classification Search
None
See application file for complete search history.

(56) References Cited

U.S. PATENT DOCUMENTS

| 5,229,273 A | 7/1993 | Gottesman et al. |
| 6,153,745 A | 11/2000 | Williams et al. |
| 6,521,453 B1 | 2/2003 | Crameri et al. |
| 6,541,226 B1 | 4/2003 | Shigemori et al. |
| 2012/0208278 A1 | 8/2012 | Yanik et al. |

FOREIGN PATENT DOCUMENTS

WO WO2012021803 * 2/2012

OTHER PUBLICATIONS

Accession I2UGF2. Jul. 11, 2012.*
Accession Q5QBN4. Jan. 4, 2005.*
Accession A7ZQC8. Oct. 23, 2007.*
Chica et al. Curr Opin Biotechnol. Aug. 2005;16(4):378-84.*
Sen et al. Appl Biochem Biotechnol. Dec. 2007;143(3):212-23.*
Altschul, et al., Gapped BLAST and PSI-BLAST: a new generation of protein database search programs (1997), Nucleic Acids Research, 25(17):3389-3402.
Chen, et al., "Mechanism of homologous recombination from the RecA-ssDNA/dsDNA structures" (2008) Nature 453, pp. 489-494.
Cox, et al., "The bacterial RecA protein as a motor protein" (2003) Annu. Rev. Microbiol. 57, pp. 551-577.
Cox, et al., "Regulation of bacterial RecA protein function" (2007) Crit. Rev. Biochem. Mol. Biol. 42, pp. 41-63.
Ferrer-Costa et al., Characterization of disease-associated single amino acid polymorphisms in terms of sequence and structure properties (2002), J Mol Biol, 315:771-786.
Ferrer-Costa et al., Sequence-based prediction of pathological mutations (2004), Proteins, 57(4):811-819.
Ferrer-Costa et al., PMUT: a web-based tool for the annotation of pathological mutations on proteins (2005), Bioinformatics, 21(14):3176-3178.
Gruenig, et al., "RecA-mediated SOS induction requires an extended filament conformation but no ATP hydrolysis" (2008) Mol. Microbiol. 69, pp. 1165-1179.
Gruenig MC, et al. (2011), Creating Directed Double-strand Breaks with the Ref Protein A novel RecA-dependent nuclease from bacteriophage P1. J Biol Chem 286:8240-8251.
Haruta N, Yu Xn, Yang Sx, Egelman Eh, & Cox MM (2003), A DNA pairing-enhanced conformation of bacterial RecA proteins. J Biol Chem 278:52710-52723.
Henikoff and Henikoff, Amino acid substitution matrices from protein blocks (1992), Proc. Natl. Acad. Sci. USA, 89:10915.
Jiang, W. Y., Bikard, D., Cox, D., Zhang, F., and Marraffini, L. A. (2013), RNA-guided editing of bacterial genomes using CRISPR-Cas systems. Nature Biotechnology 31, 233-239.
Jiang, et al., "The active form of DNA polymerase V is UmuD'(2)C-RecA-ATP" (2009) Nature 460, pp. 359-363.
Kopsidas et al., (2007), BMC Biotechnology, 7:18-29; and "error-prone PCR methods."
Laufer, et al., "Enhancement of *Escherichia coli* plasmid and chromosomal recombination by the Ref function of bacteriophage P1" (1989) Genetics 123, pp. 465-476.
Lin-Goerke et al., PCR-based random mutagenesis using manganese and reduced dNTP concentration (1997), Biotechniques, 23:409-412.
Lu, et al., "Stimulation of IS1 excision by bacteriophage P1 ref function" (1989) J. Bacteriol. 171, pp. 3427-3432.
Lusetti et al., Magnesium Ion-dependent Activation of the RecA Protein Involves the C Terminus (2003), J Biol Chem, 278:16381-16388.
Mahillon, et al., "Insertion sequences" (1998) Microbiology and Molecular Biology Reveiws, vol. 62 No. 3 725-774.
Messing J (1983), New M13 vectors for cloning. Methods Enzymol. 101:20-78.
Needleman and Wunsch, A General Method Applicable to the Search for Similarities in the Amino Acid Sequence of Two Proteins (1970), J. Mol. Biol., 48:444-453.
Neuendorf SK & Cox MM, (1986) Exchange of RecA protein between adjacent RecA protein single-stranded DNA complexes. J. Biol. Chem. 261:8276-8282.
Ng and Henikoff, Predicting the Effects of Amino Acid Substitutions on Protein Function (2006), Ann Rev Genomics Hum Genet., 7:61-80.
Opalinska, et al., "Nucleic-acid therapeutics: Basic principles and recent applications" (2002) Nature Review Drug Discovery vol. 1 503-514.
Dsuna et al., Protein evolution by codon-based random deletions (2004), Nucleic Acids Res., 32(17):e136.

(Continued)

*Primary Examiner* — Christian Fronda
(74) *Attorney, Agent, or Firm* — Quarles & Brady, LLP

(57) ABSTRACT

Purified Ref polypeptides with increased nuclease site-specific targeting activity, recombinant nucleic acids and cells for expression of such Ref polypeptides, and methods for using the Ref polypeptides in combination with RecA protein and variants thereof to effect targeted nuclease cleavage of a DNA duplex are disclosed.

17 Claims, 20 Drawing Sheets

(56) References Cited

OTHER PUBLICATIONS

Pearson, Rapid and sensitive sequence comparison with FASTP and FASTA (1990), Meth. Enzymol., 183:63.
Pearson and Lipman, Improved tools for biological sequence comparison (1988), Proc. Nat'l Acad. Sci. USA, 85:2444.
Robu, et al., "Situational repair of replication forks: roles of RecG and RecA proteins" (2004) J. Biol. Chem. 279, pp. 10973-10981.
Ronayne EA & Cox MM (2014), RecA-dependent programmable endonuclease Ref cleaves DNA in two distinct steps. Nucleic Acids Res 42: 3871-3883.
Scott, The zinc finger nuclease monopoly (2005) Nature Biotechnology 23 (8), pp. 915-918.
Sellers, On the Theory and Computation of Evolutionary Distances (1974), SIAM J. Appl. Math., 26:787.
Shigemori, et al., "Specific Cleavage of DNA Molecules at RecA-mediated triple-strand Structure" 2004 Nucleic Acids Research vol. 32, No. 1, p. E4.
Wefers, et al., Design and Generation of Gene-Targeting Vectors (2011), Current Protocols in Mouse Biology, 199-211.
Windle, et al., "A phage P1 function that stimulates homologous recombination of the *Escherichia coli* chromosome" (1986) Proc. Natl. Acad. Sci. U.S.A. 83, pp. 3885-3889.
Wong et al., Sequence saturation mutagenesis (SeSaM): a novel method for directed evolution (2004), Nucleic Acids Res., 10; 32(3):e26).
Xu et al., Random Mutagenesis Libraries: Optimization and Simplification by PCR (1999), Biotechniques, 27:1102-1108.
International Search Report mailed Apr. 11, 2011 for PCT/US2011/047584.

\* cited by examiner

REF NUCLEASE FOR SITE-SPECIFIC REF-MEDIATED DNA CLEAVAGE

CROSS-REFERENCE TO RELATED APPLICATIONS

This application claims the benefit of U.S. Provisional Patent Application Ser. No. 61/856,667 filed on Jul. 20, 2013, which is incorporated by reference herein.

STATEMENT REGARDING FEDERALLY SPONSORED RESEARCH OR DEVELOPMENT

This invention was made with government support under GM032335 awarded by the National Institutes of Health. The government has certain rights in the invention.

BACKGROUND

A variety of endonucleases, designated "restriction enzymes" or "restriction endonucleases," are used in the art to cleave double-stranded DNA. These enzymes bind to specific sequences of DNA (the "recognition site") and cleave the DNA either at the recognition site or at a site that is some distance away from the recognition site.

Although restriction enzymes are an important and widely-used tool in molecular biology applications, the use of restriction enzymes has certain limitations resulting from the functional properties of the restriction enzymes. First, the locations at which restriction enzymes can cleave a given double-stranded DNA molecule are limited to the specific nucleotide sequences on the DNA molecule that correspond to the recognition sites of available restriction enzymes. A given restriction enzyme will cleave DNA only at or a certain distance from a specific DNA sequence corresponding to the restriction enzyme recognition site. Although different restriction enzymes may have different recognition sites, there are a limited number of available restriction enzymes, and thus a limited number of recognition sites at which double-stranded DNA can be cleaved. If cleavage is desired at a certain pre-determined location on the DNA molecule that does not contain a known restriction enzyme recognition site, such a site must be engineered into the DNA molecule, which can be a difficult and time-consuming task.

Second, restriction enzymes often cleave double-stranded DNA at more than one location, even if cleavage is desired at only a single location. Because restriction enzyme recognition sites generally have relatively short nucleotide sequences (e.g. 4-9 nucleotides), a double-stranded DNA molecule may frequently contain a given recognition site at multiple locations. In such a case, the use of restriction enzymes to cleave a double-stranded DNA molecule at a target location may result in cleavage at both the target location and at additional recognition sites where cleavage is not desired.

Zinc finger endonucleases (ZFN) have been used in gene therapy applications to introduce double strand breaks at a specific chromosomal locus and to induce homology-directed repair with an exogenously added donor DNA sequence (Scott, 2005). However, the use of this technology is limited by the need to generate a new ZFN for each specific knockdown target, which is a difficult and expensive task.

Thus, there is a need in the art for a method of cleaving a double-stranded DNA molecule at a pre-determined location in a sequence-directed manner, without requiring either the generation of a novel ZFN or the engineering of a restriction enzyme recognition site at the pre-determined location.

BRIEF SUMMARY OF THE INVENTION

In previous work, we discovered that Ref, in combination with RecA and a single-stranded DNA targeting fragment ("targeting oligonucleotide") having a nucleotide sequence identical to a desired target sequence on a double-stranded (duplex) DNA molecule, can be used to cleave the double-stranded DNA molecule at the desired target sequence. Specifically, RecA will bind to the single-stranded DNA targeting fragment to create a nucleoprotein complex. When this complex encounters a homologous double-stranded DNA molecule, the RecA will invade the double-stranded DNA molecule and pair the single-stranded DNA targeting fragment to the complementary sequence in one strand of the double-stranded DNA molecule. The other strand of the duplex (the one identical in sequence to the targeting oligonucleotide) is displaced, and a structure is formed that is often referred to as a D-loop. In the presence of the RecA-bound and paired DNA targeting fragment, Ref will cleave both strands of the targeted double-stranded DNA molecule at the desired target sequence, within the D-loop. Thus, the RecA, Ref, and single-stranded DNA targeting oligonucleotide act together as a designer nuclease, capable of cleaving any desired target sequence in a double-stranded DNA molecule. All that is required is to provide a single stranded DNA targeting fragment (e.g., an oligonucleotide) that is identical in sequence to the desired target.

The present invention is based on the unexpected finding that N-terminal truncation variants of Ref exhibit enhanced nuclease site-specific targeting activity relative to naturally occurring full length wildtype Ref proteins. Accordingly, the present invention relates generally to novel N-terminal deleted Ref polypeptides, nucleic acids encoding such Ref polypeptides, and related compositions and methods for their use in sequence-targeted cleavage of double-stranded DNA molecules.

In a first aspect described herein is a purified Ref polypeptide comprising an amino acid sequence at least 95% identical to any of SEQ ID NOs:4 and 5, where: (i) the polypeptide does not comprise the entire amino acid sequence of a naturally occurring full length Ref protein of SEQ ID NO:1 or SEQ ID NO:2 in that a section of the n-terminal end of the sequence has been deleted; and (ii) the purified Ref polypeptide exhibits an increased nuclease site-specific targeting activity relative to nuclease site-specific targeting activity of a naturally occurring full length wildtype Ref protein or full length Ref protein comprising the amino acid of any of SEQ ID NOs:1-2.

In some embodiments the above-mentioned purified Ref polypeptide comprises the amino acid sequence of any of SEQ ID NOs:4-5. In other embodiments the Ref polypeptide consists of any of SEQ ID NOs:4-5.

In some embodiments, the Ref polypeptide comprises an amino acid sequence at least 95% identical to any of SEQ ID NOs: 6-7. In other embodiments the purified Ref polypeptide comprises the amino acid sequence of any of SEQ ID NOs: 6-7. In some embodiments the amino acid sequence of the Ref polypeptide consists of any of SEQ ID NOs: 6-7.

In some embodiments the purified Ref polypeptide comprises an amino acid sequence at least 95% identical to any of SEQ ID NOs:8-9. In some embodiments the purified Ref polypeptide comprises the amino acid sequence of any of SEQ ID NOs:8-9. In some embodiments the amino acid sequence of the purified Ref polypeptide consists of any of SEQ ID NOs:8-9.

In further embodiments the purified Ref polypeptide comprises an amino acid sequence at least 95% identical to any of SEQ ID NOs:10-11. In some embodiments, the purified Ref polypeptide comprises the amino acid sequence of any of SEQ ID NOs:10-11. In further embodiments the amino acid sequence of the Ref polypeptide consists of any of SEQ ID NOs:10-11.

In other embodiments the purified Ref polypeptide is a fusion polypeptide.

In a related aspect described herein is a kit that includes: (i) one of the above-mentioned purified Ref polypeptides; and (ii) a purified RecA polypeptide comprising an amino acid sequence at least 95% identical to any of SEQ ID NOs:12-16, where the activity of the purified RecA polypeptide is at least 70% of the activity of at least one full length RecA protein comprising the amino acid sequence of any of SEQ ID NOs:12-16. In some embodiments, the purified RecA included in the kit comprises an amino acid sequence at least 95% identical to SEQ ID NO:13. In some embodiments, the amino acid sequence of the purified RecA polypeptide consists of SEQ ID NO:13.

In some embodiments, the above-mentioned kit also includes a targeting oligonucleotide. In some embodiments the targeting oligonucleotide is 30-150 nucleotides in length. In some embodiments the targeting oligonucleotide is 100-140 nucleotides in length.

In some embodiments, the kit also includes a reaction buffer suitable for an in vitro nuclease site-specific targeting reaction in the presence of the purified Ref polypeptide (i), the purified RecA polypeptide (ii), a targeting oligonucleotide, and a double stranded DNA comprising a target sequence to be cleaved.

In a second aspect described herein is a recombinant nucleic acid encoding a Ref polypeptide comprising an amino acid sequence at least 95% identical to any of SEQ ID NOs:4 and 5, where (i) the encoded polypeptide does not comprise the entire amino acid sequence of a naturally occurring full length Ref protein; SEQ ID NO:1; or SEQ ID NO:2; and (ii) the encoded polypeptide exhibits an increased nuclease site-specific targeting activity relative to Nuclease site-specific targeting activity of a full length wildtype Ref, or a Ref protein comprising the amino acid sequence of any of SEQ ID NOs:1-2.

In some embodiments, the recombinant nucleic acid also includes a heterologous nucleic acid sequence on its 5' or 3' end. In some embodiments, the heterologous nucleic acid is a 5' UTR, a 3' UTR, a Kozak consensus sequence, Shine-Delgarno sequence, or a promoter.

In some embodiments the recombinant nucleic acid is provided as a vector that includes the recombinant nucleic acid sequence.

In a related aspect provided herein is a recombinant cell containing the above-mentioned recombinant nucleic acid encoding the Ref polypeptide.

In a third aspect provided herein is a method for cleaving a DNA duplex within a target-defined nucleotide sequence, which method includes the steps of: (i) providing a complex of a RecA protein, a double stranded DNA, and a targeting oligonucleotide comprising a sequence homologous to a target sequence found within the double stranded DNA; and (ii) contacting the complex from (i) with a purified Ref polypeptide comprising an amino acid sequence at least 95% identical to any of SEQ ID NOs:4-5, where (a) the purified Ref polypeptide does not comprise the entire amino acid sequence of a naturally occurring full length Ref protein, or a Ref protein comprising the amino acid sequence of any of SEQ ID NOs:1-2; and (b) the purified Ref polypeptide exhibits an increased Nuclease site-specific targeting activity relative to Nuclease site-specific targeting activity of a full length wildtype Ref, or a Ref protein comprising the amino acid sequence of any of SEQ ID NOs:1 or 2.

In some embodiments the polypeptide to be used in the method comprises an amino acid sequence at least 95% identical to any of SEQ ID NOs: 6-7. In some embodiments, the Ref polypeptide to be used comprises the amino acid sequence of any of SEQ ID NOs: 6-7. In other embodiments the amino acid sequence of the polypeptide consists of any of SEQ ID NOs: 6-7.

In further embodiments the Ref polypeptide used comprises an amino acid sequence at least 95% identical to any of SEQ ID NOs:8-9. In other embodiments the Ref polypeptide comprises the amino acid sequence of any of SEQ ID NOs:8-9. In some embodiments the amino acid sequence of the Ref polypeptide used in the methods consists of any of SEQ ID NOs:8-9.

In some embodiments of the method the Ref polypeptide to be used comprises an amino acid sequence at least 95% identical to any of SEQ ID NOs:10-11. In other embodiments, the Ref polypeptide comprises any of SEQ ID NOs:10-11. In some embodiments, the amino acid sequence of the polypeptide consists of any of SEQ ID NOs: 10-11.

In other embodiments the targeting oligonucleotide used in the above-mentioned methods is from 30-1,000 nucleotides in length. In other embodiments the targeting oligonucleotide is from 60-150 nucleotides in length. In other embodiments the targeting oligonucleotide is from 100-140 nucleotides in length.

These and other features of the present invention will become apparent to the skilled artisan from the following detailed description considered in conjunction with the accompanying drawings.

Figure 1:
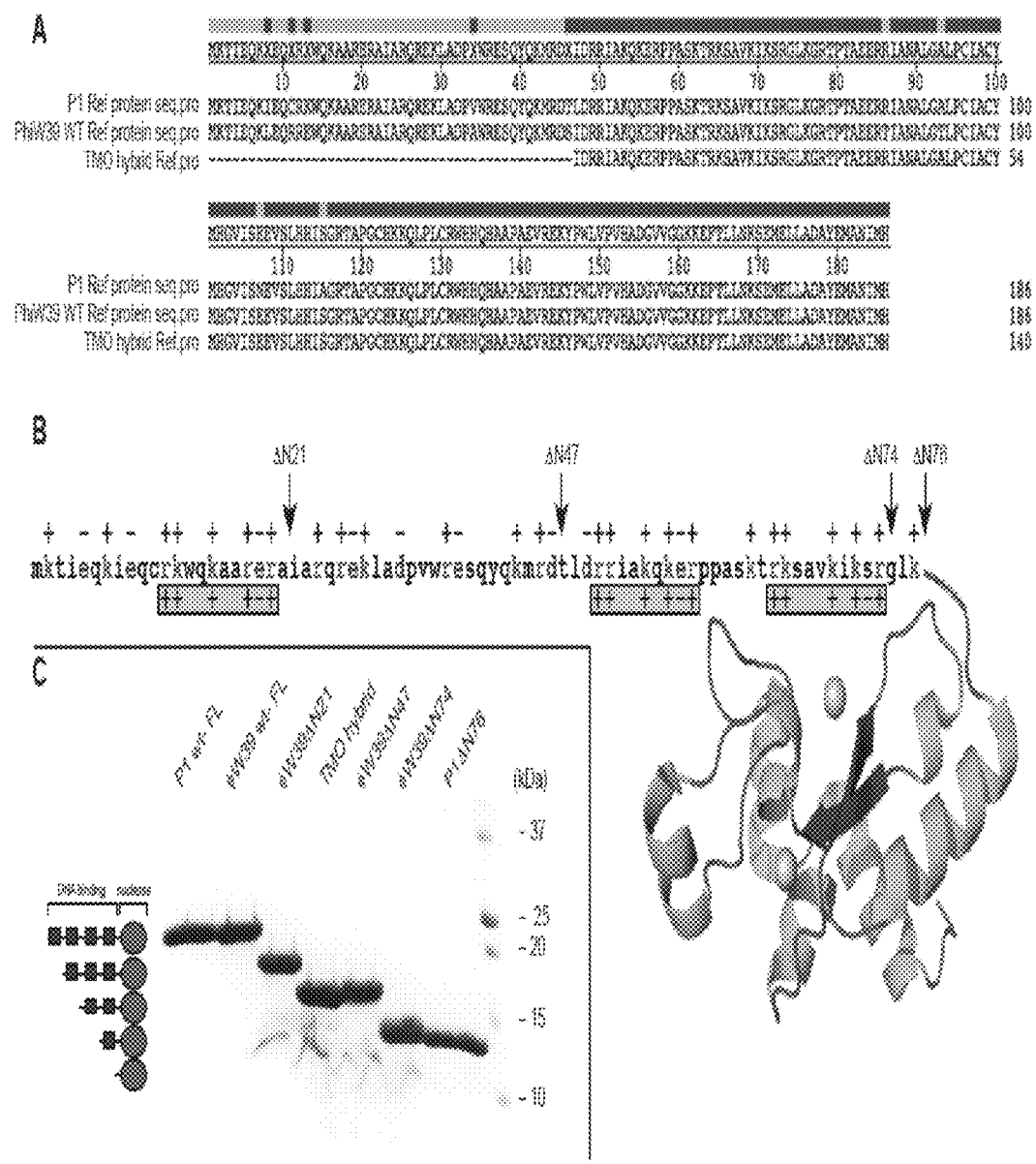
FIG. 1 shows a sequence alignment and overview of Ref truncation variants based on charge distribution. (A) Protein sequence alignment of P1 Ref (SEQ ID NO:1), φW39 Ref (SEQ ID NO:2), and TMO hybrid Ref (SEQ ID NO:3) proteins. There are ten amino acid differences between P1 Ref and φW39 Ref. TMO hybrid is a truncated version with a mix of P1 Ref and φW39 Ref amino acids. (B) Schematic of protein sequence and charge distribution of unstructured N-terminal 76 amino acids of P1 Ref (amino acid residues 1-76 of SEQ ID NO:1). Based on the signature charge distribution (++ + +-+) pattern shown below the sequence, various truncations of φW39 Ref were cloned and purified. (C) Schematic of Ref truncations and image of a Coomassie-stained SDS-page gel containing ~4 ug of each construct, left and right panels respectively. All proteins were soluble and the C-terminal core was folded properly.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

We have developed improved variants of Ref exhibiting increased Rec-dependent, sequence-targeted nuclease activity, as well as related compositions and methods. Methods and kits for cleaving a double-stranded (duplex) DNA molecule at a homologous target sequence, where homologous is defined as a site with one strand identical and the other complementary to the sequence of a single-stranded DNA targeting fragment, are disclosed. In addition to the targeted duplex DNA molecule and the single-stranded DNA targeting fragment, the method requires both a RecA protein, homolog or variant, and a Ref protein, homolog or variant. The method is preferably performed in the presence of ATP and a divalent cation, such as $Mg^{2+}$ or $Mn^{2+}$.

I. Definitions

"Duplex DNA" encompasses all such molecules, including without limitation genomic, non-genomic, synthetic, or semisynthetic double-stranded DNA molecules or fragments thereof. Non-limiting examples of duplex DNA include prokaryotic and eukaryotic chromosomes, plasmids and plasmid vectors, double-stranded viral DNA, double-stranded mitochondrial DNA, double-stranded synthetic oligonucleotides, and fragments thereof.

A "fusion polypeptide" refers to a polypeptide comprising at least two heterologous amino acid sequences, where a first amino acid sequence is linked to the amino terminus or carboxy terminus of a second amino acid sequence to generate a contiguous amino acid sequence that is not naturally occurring.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

A "purified polypeptide," refers to a polypeptide that is substantially removed from or concentrated with respect to its presence in its natural environment.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

A "recombinant" nucleic acid refers to a polydeoxynucleotide or polyribonucleotide that is not naturally occurring. In some cases a recombinant nucleic acid includes juxtaposed heterologous sequences that are not found naturally adjacent or in close proximity to one another. In other cases, a recombinant nucleic acid consists of a DNA or RNA nucleotide subsequence, which itself is not found naturally, but which is found within a larger sequence that is naturally occurring, e.g., an RNA encoding a fragment of a Ref polypeptide.

A "targeting oligonucleotide" refers to a single stranded DNA fragment designed to share homology, preferably of at least 30 nucleotides, with a duplex DNA molecule sequence of interest. Preferably, the targeting oligonucleotide contains no more than 2 mismatches with respect to a target sequence per 30 nucleotides of sequence. A targeting oligonucleotide typically ranges in length from at least 30 nucleotides to about 1000 nucleotides. In preferred cases, the length of a targeting oligonucleotide ranges from about 60 to about 150 nucleotides. In other preferred cases, the length of a targeting oligonucleotide ranges from about 100 to about 140 nucleotides.

II. Compositions

Purified Ref Fragment Polypeptides with Enhanced Nuclease Activity

Described herein are purified Ref polypeptides comprising N-terminal sequence truncation or deletion variants of a Ref polypeptide. Unexpectedly, such Ref variants exhibit increased Rec-dependent, sequence-targeted nuclease activity relative to a full length Ref protein comprising the amino acid sequence of any of SEQ ID NOs 1-2.

P1 Phage full length Ref (GenBank Accession No. YP_006474.1; SEQ ID NO: 1-residues 67-186 are shown in bold):

(SEQ ID NO: 1)
MKTIEQKIEQCRKWQKAARERAIARQREKLADPVWRESQYQKMRDTL

DRRIAKQKERPPASKTRKSAVKIKSRGLKGRTPTAEERRIANALGAL

PCIACYMHGVISNEVSLHHIAGRTAPGCHKKQLPLCRWHHQHAAPAE

VREKYPWLVPVHADGVVGGKKEFTLLNKSEMELLADAYEMANIMH

φW39 Phage full length Ref Protein-underlined residues indicate differences relative to P1 wildtype Ref (GenBank Accession No. WP_001568010.1; SEQ ID NO: 2):
MKTIEQKLEQRREWQKAARERAIARQREKLADPAWRESQYQKMRDSI

DRRIAKQKERPPASKTRKSAVKIKSRGLKGRTPTAEERTIANALGTL

PCIACYMHGVISEEVSLHHISGRTAPGCHKKQLPLCRWHHQHAAPAE

VREKYPWLVPVHADGVVGGKKEFTLLNKSEMELLADAYEMANIMH

TMO hybrid Ref (SEQ ID NO: 3):
IDRRIAKQKERPPASKTRKSAVKIKSRGLKGRTPTAEERRIANALGA

LPCIACYMHGVISEEVSLHHISGRTAPGCHKKQLPLCRWHHQHAAPA

EVREKYPWLVPVHADGVVGGKKEFTLLNKSEMELLADAYEMANIMH

In some embodiments a purified Ref polypeptide disclosed herein comprises an amino acid sequence at least 90% identical to any of SEQ ID NOs 4 and 5, corresponding to amino acids 67-186 of any of SEQ ID NOs:1 or 2, respectively, e.g., 91%, 92%, 93%, 94%, 95%, 96%, 97%, 98%, 98%, 99%, or another percent identity from 90% to 100% identical to any of SEQ ID NOs:1-3; where such purified Ref polypeptides (i) do not comprise the full length amino acid sequence of a naturally occurring Ref such as that of SEQ ID NOs:1 or 2 in that a section of the n-terminal sequence has been deleted; and (ii) such purified Ref polypeptides exhibit an increased nuclease site-specific targeting activity relative to that of P1 wildtype full length Ref (SEQ ID NO:1) or φW39 Phage wildtype full length Ref (SEQ ID NO:2).

The skilled artisan will appreciate that this nuclease site-specific targeting activity requires two strand cleavage events. While not wishing to be bound by theory, it is believed that these cuts are ordered, such that the first cut occurs rapidly on the strand that is paired with the targeting oligonucleotide oligo in the D-loop (the paired strand), and the second cut occurs on the displaced strand. The first cut is believed is to be much faster than the second cut, which is comparatively slow and limits the rate of the overall reaction. It is believed that the Ref polypeptides described herein greatly increase the rate of the first cut (as much as five fold), which, when followed by the slower second cut yields an overall increased nuclease site-specific targeting activity. In some embodiments, the increased nuclease site-specific targeting activity of the purified Ref polypeptides disclosed herein is at least 20% to 1000% greater than the nuclease site-specific targeting activity of a full length Ref protein comprising the amino acid sequence of any of SEQ ID NOs:1-2, e.g., 30%, 40%, 50%, 60%, 70%, 80%, 100%, 150%, 200%, 250%, 300%, 350%, 400%, 500%, 600%, 650%, 700%, 750%, 800%, 850%, or 900% greater nuclease activity than a full length Ref protein comprising any of SEQ ID NOs:1-2. In some embodiments, the nuclease site-specific targeting activity of the purified Ref polypeptide is about 20% to about 60% greater than the nuclease site-specific targeting activity of a full length Ref protein comprising the amino acid sequence of any of SEQ ID NOs:1-2.

In some embodiments, a purified Ref polypeptide disclosed herein comprises the amino acid sequence of any of SEQ ID NOs: 4 or 5, which correspond to the amino acid sequence of residues 67-186 of SEQ ID NOs:1 and 2, respectively. In some embodiments the amino acid sequence of the purified Ref polypeptide consists of any of SEQ ID NOs:4 or 5.

SEQ ID NO: 4(amino acids 67-186 of SEQ ID NO: 1):
AVKIKSRGLKGRTPTAEERRIANALGALPCIACYMHGVISNEVSLHHI

AGRTAPGCHKKQLPLCRWHHQHAAPAEVREKYPWLVPVHADGVVGGKK

EFTLLNKSEMELLADAYEMANIMH

SEQ ID NO: 5(amino acids 67-186 of SEQ ID NO: 2):
AVKIKSRGLKGRTPTAEERTIANALGTLPCIACYMHGVISEEVSLHHI

SGRTAPGCHKKQLPLCRWHHQHAAPAEVREKYPWLVPVHADGVVGGKK

EFTLLNKSEMELLADAYEMANIMH

In some embodiments, the purified Ref polypeptides provided herein comprise an amino acid sequence that is at least 95% identical to any of SEQ ID NOs 6 or 7, which correspond to amino acids 48-186 of SEQ ID NOs:1 and 2, respectively. In some embodiments the purified Ref polypeptides comprise the amino acid sequence of any of SEQ ID NOs:6 or 7. In some embodiments the amino acid sequence of the purified Ref polypeptide consists of any of SEQ ID NOs:6 or 7.

(SEQ ID NO: 6):
DRRIAKQKERPPASKTRKSAVKIKSRGLKGRTPTAEERRIANALGALP

CIACYMHGVISNEVSLHHIAGRTAPGCHKKQLPLCRWHHQHAAPAEVR

EKYPWLVPVHADGVVGGKKEFTLLNKSEMELLADAYEMANIMH (SEQ ID NO: 7):
DRRIAKQKERPPASKTRKSAVKIKSRGLKGRTPTAEERTIANALGTLP

CIACYMHGVISEEVSLHHISGRTAPGCHKKQLPLCRWHHQHAAPAEVR

EKYPWLVPVHADGVVGGKKEFTLLNKSEMELLADAYEMANIMH

In other embodiments, the purified Ref polypeptides described herein comprise an amino acid sequence that is at least 95% identical to any of SEQ ID NOs:8 or 9, corresponding to amino acids 22-186 of SEQ ID NOs: 1 and 2, respectively. In some embodiments, the purified Ref polypeptides comprise the amino acid sequences of any of SEQ ID NOs:8 or 9. In some embodiments the amino acid sequence of the purified Ref polypeptide consists of any of SEQ ID NOs:8 or 9.

(SEQ ID NO: 8):
AIARQREKLADPVWRESQYQKMRDTLDRRIAKQKERPPASKTRKSAVK

IKSRGLKGRTPTAEERRIANALGALPCIACYMHGVISNEVSLHHIAGR

TAPGCHKKQLPLCRWHHQHAAPAEVREKYPWLVPVHADGVVGGKKEFT

LLNKSEMELLADAYEMANIMH (SEQ ID NO: 9):
AIARQREKLADPAWRESQYQKMRDSIDRRIAKQKERPPASKTRKSAVK

IKSRGLKGRTPTAEERTIANALGTLPCIACYMHGVISEEVSLHHISGR

TAPGCHKKQLPLCRWHHQHAAPAEVREKYPWLVPVHADGVVGGKKEFT

LLNKSEMELLADAYEMANIMH

In other embodiments the purified Ref polypeptides described herein comprise an amino acid sequence at least 95% identical to any of any of SEQ ID NOs:10 or 11, corresponding to amino acids 11-186 of SEQ ID NOs:1 and 2, respectively. In some embodiments the amino acid sequence of the purified Ref polypeptide consists of any of SEQ ID NOs:10 or 11.

(SEQ ID NO: 10):
CRKWQKAARERAIARQREKLADPVWRESQYQKMRDTLDRRIAKQKERP

PASKTRKSAVKIKSRGLKGRTPTAEERRIANALGALPCIACYMHGVIS

NEVSLHHIAGRTAPGCHKKQLPLCRWHHQHAAPAEVREKYPWLVPVHA

DGVVGGKKEFTLLNKSEMELLADAYEMANIMH (SEQ ID NO: 11):
RREWQKAARERAIARQREKLADPAWRESQYQKMRDSIDRRIAKQKERP

PASKTRKSAVKIKSRGLKGRTPTAEERTIANALGTLPCIACYMHGVIS

EEVSLHHISGRTAPGCHKKQLPLCRWHHQHAAPAEVREKYPWLVPVHA

DGVVGGKKEFTLLNKSEMELLADAYEMANIMH

Evaluating the structural and functional homology of two or more polypeptides generally includes determining the percent identity of their amino acid sequences to each other. Sequence identity between two or more amino acid sequences is determined by conventional methods. See, for example, Altschul et al., (1997), *Nucleic Acids Research,* 25(17):3389-3402; and Henikoff and Henikoff (1982), *Proc. Natl. Acad. Sci. USA,* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the shorter sequence plus the number of gaps introduced into the longer sequence in order to align the two sequences])(100).

Those skilled in the art will appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman (1988), *Proc. Nat'l Acad. Sci. USA,* 85:2444, and by Pearson (1990), *Meth. Enzymol.,* 183:63. Briefly, FASTA first characterizes sequence similarity by identifying regions shared by the query sequence (e.g., any of SEQ ID NOs:4-11) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch (1970), *J. Mol. Biol.,* 48:444-453; Sellers (1974), *SIAM J. Appl. Math.,* 26:787), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson (1990), *Meth. Enzymol.,* 183:63.

A number of considerations are useful to the skilled artisan in determining if a particular amino acid sequence variant of a Ref polypeptide is likely to have increased nuclease site-specific targeting activity relative to the activity exhibited by wildtype P1 phage Ref or φW39 phage Ref. These considerations include, but are not limited to: (1) known structure-function relationships for the variant polypeptide, e.g., the number of motifs such as the signature charge distribution (SCD) motif described herein; (2) the presence of amino acid sequence conservation among naturally occurring homologs (e.g., in paralogs and orthologs) of the Ref polypeptide, as revealed by sequence alignment algorithms as described herein. Notably, a number of bioinformatic algorithms are known in the art that successfully predict the functional effect, i.e., "tolerance" of particular amino substitutions in the amino acid sequence of a protein on its function. Such algorithms include, e.g., pMUT, SIFT, PolyPhen, and SNPs3D. For a review see, e.g., Ng and Henikoff (2006), *Ann Rev Genomics Hum Genet.*, 7:61-80. For example, pMUT predicts with a high degree of accuracy (about 84% overall) whether a particular amino acid substitution at a given sequence position affects a protein's function based on sequence homology. See Ferrer-Costa et al., (2005), *Bioinformatics,* 21(14):3176-3178; Ferrer-Costa et al., (2004), *Proteins,* 57(4):811-819; and Ferrer-Costa et al., (2002), *J Mol Biol,* 315:771-786. The SIFT algorithm server is publicly available on the world wide web at: blocks.fhcrc.org/sift/SIFT.html. Thus, for any Ref polypeptide amino acid sequence, an "amino acid substitution matrix" can be generated that provides the predicted neutrality or deleteriousness of any given amino acid substitution on Ref polypeptide function.

In preferred embodiments, where an amino acid is to be substituted within one of the Ref polypeptide sequences disclosed herein, the amino acid substitution is a conservative amino acid substitution. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Non-naturally occurring sequence variants can be generated by a number of known methods. Such methods include, but are not limited to, "Gene Shuffling," as described in U.S. Pat. No. 6,521,453; "RNA mutagenesis," as described in Kopsidas et al., (2007), BMC Biotechnology, 7:18-29; and "error-prone PCR methods." Error prone PCR methods can be divided into (a) methods that reduce the fidelity of the polymerase by unbalancing nucleotides concentrations and/or adding of chemical compounds such as manganese chloride (see, e.g., Lin-Goerke et al., (1997), *Biotechniques,* 23:409-412), (b) methods that employ nucleotide analogs (see, e.g., U.S. Pat. No. 6,153,745), (c) methods that utilize 'mutagenic' polymerases (see, e.g., Cline, J. and Hogrefe, H. H. (2000), *Strategies* (Stratagene Newsletter), 13:157-161 and (d) combined methods (see, e.g., Xu et al., (1999), *Biotechniques,* 27:1102-1108. Other PCR-based mutagenesis methods include those, e.g., described by Osuna et al., (2004), *Nucleic Acids Res.,* 32(17):e136 and Wong et al., (2004), *Nucleic Acids Res.,* 10; 32(3):e26), and others known in the art.

Confirmation of the retention, loss, or gain of function of the amino acid sequence variants of a Ref polypeptide variant relative to a full length Ref protein, e.g., P1 phage Ref (SEQ ID NO:1) or ϕW39 phage Ref (SEQ ID NO:2) can be determined by using a nuclease site-specific targeting assay as described herein.

The N-terminal (1-76) amino acids of full length Ref proteins, such as those comprising the amino acids sequences of SEQ ID NOs:1 and 2, are characterized by a signature charge distribution (SCD) motif in the form "++..+. +-+" repeated three times across residues 1-76 (12-21; 49-57; and 64-73). While not wishing to be bound by theory, it is believed that this motif may modulate the ability of a Ref polypeptide to bind to DNA and to dimerize. Based on the results described herein, the presence of all three motifs, as found in full length Ref proteins, increases the affinity of the polypeptide for DNA, but may decrease the amount of nuclease site-specific targeting due to competition with RecA DNA binding. On the other hand, elimination of all three motifs abolishes the ability of a Ref polypeptide to bind DNA, dimerize, and nuclease activity. Thus, the skilled artisan will appreciate that in generating a purified Ref polypeptide as described herein, the underlying amino acid sequence should retain at least one SCD motif.

The purified Ref polypeptides described herein can be prepared by a number of methods known in the art, though preferably, they are purified from a recombinant expression host organism, e.g, *E. coli*. In one exemplary embodiment, Ref variant polypeptides are purified as follows.

Competent cells of *E. coli*, e.g., strain BL21(DE3) are transformed with an inducible expression vector. Ten liters of transformant culture are grown in LB broth to an A600 of 0.51. Ref protein expression is induced by the addition of isopropyl 1-thio-β-d-galactopyranoside to 0.4 mm. After a 3-h 10-min outgrowth at 37° C., cells are harvested by centrifugation, flash-frozen in liquid N2, and stored at −80° C.

All purification steps are carried out at 4° C. Purification includes sequential polyethyleneimine precipitation and pellet extraction, precipitation with $(NH_4)_2SO_4$, and chromatography successively using butyl-Sepharose, Source 15 Q, ceramic hydroxyapatite columns, and Sephacryl S-100 gel filtration columns. This is followed by another butyl-Sepharose chromatography step. Optionally, additional ceramic hydroxyapatite and butyl-Sepharose steps may be used. The protein is concentrated using Amicon Centricon-Plus 20 and dialyzed against Ref storage buffer (20 mM TrisHcl 80% cation, pH 7.6, 1 mM EDTA, and 10% glycerol; and 200 mm potassium glutamate), flash-frozen in liquid $N_2$, and stored at 80° C. Ref polypeptides purified by this method are typically >99% pure and free of detectable non-specific nuclease activity when incubated at 37° C. for 2 h with different DNA substrates (circular ssDNA, linear and supercoiled dsDNA, and labeled oligonucleotides) in a buffer containing 25 mm Tris-OAc (80% cation, pH 7.6), 1 mm DTT, 3 mm potassium glutamate, 10 mm $Mg(OAc)_2$, and 5% (w/v) glycerol (buffer A).

Protein concentration is determined by absorbance at 280 nm. Protein identity is confirmed by excising the protein band from a gel and digesting with trypsin followed by MALDI-TOF/TOF mass spectrometry.

Nuclease site-specific targeting activity of the purified Ref polypeptides described herein can be determined by a number of methods known in the art. In one exemplary embodiment, this activity is tested as follows. Reactions are carried out at 37° C. in buffer A, (containing 25 mM Tris-acetate (pH 8.5), 1 mM DTT, 3 mM potassium glutamate, 15 mM magnesium acetate, and 5% w/v glycerol) and an ATP regeneration system (10 U/mL pyruvate kinase and 3.5 mM phosphoenolpyruvate. The above components are incubated for 10 minutes with a targeting oligonucleotide (4 µM nt, rlb1 150mer-SEQ ID NO:17) and RecA E38K (1.33 µM) (SEQ ID NO:13). ATP (3 mM) is then added and the reaction is incubated an additional 20 minutes, followed by addition of M13mp18 circular dsDNA (8 µM nt) and another 20 minute incubation. Before adding a purified Ref polypeptide to be tested, a zero time point is taken, then the polypeptide (100 nM) is added. The reactions are stopped at various time points (e.g., 10 minutes, 30 minutes, and 60 minutes) up to an hour by removing 20 µL from the reaction and adding it to 20 µL of stop solution (12 mM Tris acetate pH 7.5, 10.8% (w/v) Ficoll, 0.15% (w/v) each bromophenol blue and xylene cyanol, 8% SDS) and incubating at 37° C. an additional 30 minutes. Samples are then analyzed by electrophoresis on a 0.8% agarose gel with TAE buffer, stained with SYBR Gold stain, and imaged using the SYBR gold settings on a Typhoon FLA 9000 (GE Healthcare) or a comparable gel image acquisition system. The gel image is then analyzed using ImageQuant TL software (GE Healthcare). Lanes are normalized for loading conditions by reporting individual band intensity as a percentage of the total band intensity in that lane. Accordingly, the nuclease site-specific targeting activity of a purified Ref polypeptide described herein, e.g., a Ref fragment polypeptide can be compared to the activity of a full length Ref protein, e.g., that of wildtype P1 Phage Ref protein (SEQ ID NO:1) or wildtype 039 phage Ref protein (SEQ ID NO:2).

Kits

Also described herein are kits that include at least: (i) a purified Ref polypeptide as described herein; and (ii) a purified RecA polypeptide.

In some embodiments, the RecA polypeptide comprises the amino acid sequence of a full length wildtype RecA at least 95% identical to the amino acid sequence of SEQ ID NO:12 (Uniprot P0A7G6):

```
                                           (SEQ ID NO: 12)
MAIDENKQKALAAALGQIEKQFGKGSIMRLGEDRSMDVETISTGSLSL

DIALGAGGLPMGRIVEIYGPESSGKTTLTLQVIAAAQREGKTCAFIDA

EHALDPIYARKLGVDIDNLLCSQPDTGEQALEICDALARSGAVDVIVV

DSVAALTPKAEIEGEIGDSHMGLAARMMSQAMRKLAGNLKQSNTLLIF

INQIRMKIGVMFGNPETTTGGNALKFYASVRLDIRRIGAVKEGENVVG

SETRVKVVKNKIAAPFKQAEFQILYGEGINFYGELVDLGVKEKLIEKA

GAWYSYKGEKIGQGKANATAWLKDNPETAKEIEKKVRELLLSNPNSTP

DFSVDDSEGVAETNEDF
```

In some embodiments, the purified RecA polypeptide comprises the amino acid sequence of SEQ ID NO:13.

In other embodiments, the purified RecA polypeptide to be included in the kit comprises the amino acid sequence of SEQ ID NO:13, which contains an E38K substitution:

```
                                           (SEQ ID NO: 13)
MAIDENKQKALAAALGQIEKQFGKGSIMRLGEDRSMDVKTISTGSLSL

DIALGAGGLPMGRIVEIYGPESSGKTTLTLQVIAAAQREGKTCAFIDA

EHALDPIYARKLGVDIDNLLCSQPDTGEQALEICDALARSGAVDVIVV

DSVAALTPKAEIEGEIGDSHMGLAARMMSQAMRKLAGNLKQSNTLLIF

INQIRMKIGVMFGNPETTTGGNALKFYASVRLDIRRIGAVKEGENVVG
```

```
-continued
SETRVKVVKNKIAAPFKQAEFQILYGEGINFYGELVDLGVKEKLIEKA

GAWYSYKGEKIGQGKANATAWLKDNPETAKEIEKKVRELLLSNPNSTP

SDFVDDSEGVAETNEDF
```

In some embodiments, the kit also includes a reaction buffer suitable for an in vitro nuclease site-specific targeting reaction in the presence of a purified Ref polypeptide described herein, a purified RecA polypeptide, a targeting oligonucleotide, and a double stranded DNA comprising a target sequence to be cleaved. In one exemplary embodiment, a suitable reaction buffer contains 25 mM Tris-acetate (pH 8.5), 1 mM DTT, 3 mM potassium glutamate, 15 mM magnesium acetate, and 5% w/v glycerol) and an ATP regeneration system (10 U/mL pyruvate kinase and 3.5 mM phosphoenolpyruvate.

Recombinant Nucleic Acids and Cells

Also described herein are recombinant nucleic acids (e.g., DS-DNA, SS-DNA, DS-RNA, or SS-RNA) encoding a polypeptide comprising an amino acid sequence at least 95% identical to any of SEQ ID NOs:4-11, where: (i) the encoded polypeptide does not comprise the entire amino acid sequence of a full length Ref polypeptide; SEQ ID NO:1; or SEQ ID NO:2; in that a section of the n-terminal end of the sequence has been deleted; and (ii) the encoded polypeptide exhibits an increased nuclease site-specific targeting activity relative to nuclease site-specific targeting activity of a full length wildtype Ref (SEQ ID NO:1) or SEQ ID NO:2.

One of ordinary skill in the art will appreciate that, due to the redundancy of the genetic code, many nucleic acid sequences having diverse nucleotide sequences can encode polypeptides having the same amino acid sequence. Further, the skilled artisan will appreciate that where a recombinant nucleic acid is used to express an encoded Ref polypeptide described herein within a particular expression host, the specific nucleotide sequence encoding the polypeptide can be chosen based on a preferred codon usage information for the particular expression host. Such codon usage information is publicly available, as found, e.g., on the world wide web at kazusa.or.jp/codon/.

In some embodiments, the above-mentioned recombinant nucleic acid also includes a heterologous nucleic acid sequence linked to its 5' or 3' end. In some embodiments, the recombinant nucleic acid includes any of a 5' UTR, a Kozak consensus sequence, a Shine-Delgarno sequence, or a promoter.

In some embodiments, the recombinant nucleic acid is a linear double-stranded DNA cassette for in vitro transcription, where the cassette includes a promoter for an RNA polymerase, e.g., T7 or SP6 polymerase followed by a 5' UTR, an open reading frame encoding a Ref polypeptide as described herein, and a 3' UTR.

In some embodiments, the recombinant nucleic acid is a vector, e.g., a plasmid vector, a viral vector (e.g., a phage vector), or a phagemid vector. In some embodiments, the vector is an expression vector suitable for expression of the encoded polypeptides described herein. In some cases the expression vector is a prokaryotic vector suitable for expression in, e.g., a prokaryotic host such as *E. coli*. In other embodiments, the expression vector is a eukaryotic expression vector. In some embodiments expression vectors include a promoter operable for expression in chosen host cells, a 5' UTR, an open reading frame encoding a Ref polypeptide as described herein, and a 3' UTR. In other embodiments, the recombinant nucleic acid is a synthetic mRNA. Such synthetic mRNAs encoding a Ref polypeptide can be transiently transfected into a host cell to drive translation of a Ref polypeptide as needed without needing to establish a stably transfected cell line or otherwise stably introducing the recombinant nucleic acid encoding Ref into a host cell. In some embodiments, such synthetic mRNAs incorporate ribonucleotide analogs that reduce their degradation by RNAses or reduce a cellular interferon response. For example, the synthetic RNA may incorporate a 5' anti-reverse cap analog (ARCA) or pseudouridine to enhance translation. Suitable methods for in vitro synthesis, transfection, and expression of mRNA in mammalian cells are described in, e.g., U.S. patent application Ser. No. 13/455,327.

Also provided herein are recombinant cells (AKA recombinant host cells) comprising one of the above-described vectors. Such recombinant cells include, e.g., recombinant prokaryotic cells (e.g., *E. coli*) and recombinant Eukaryotic cells, e.g., yeast cells and mammalian cells. In preferred embodiments, the recombinant cells express a Ref polypeptide encoded by one of the above-described vectors. Expression may be constitutive or inducible. In some embodiments, a recombinant cell is generated by transient transfection with an expression vector encoding a Ref polypeptide described herein. In other embodiments the recombinant cell is generated by stable transfection or transformation into a host cell. A variety of methods for transient or stable transfection of vectors, particularly expression vectors are well established and routinely used in the art.

In some embodiments, a recombinant cell is a mammalian cell that comprises a Ref polypeptide as described herein, a RecA polypeptide (e.g., a RecA E38K variant), and at least one targeting oligonucleotide of at least 30 to about 200 nucleotides, wherein the nucleotide sequence of the targeting oligonucleotide is at least 95% identical over its entire length to an endogenous genomic sequence in the recombinant mammalian host cell. In some embodiments, the just mentioned mammalian recombinant cell comprises two targeting oligonucleotides directed to genomic sequences flanking a genomic target region (GTR), and in addition a targeting vector comprising a homology targeting insert, which contains at least left "arm" and right arm sequences having at least 99% homology to genomic target region over their entire length. The sequence flanked by the two homology arms may contain, e.g., a region with at least 95% homology to the genomic target region sequence, but containing a point mutation, a deletion, or an insertion with respect to the genomic target region sequence. Alternatively, the intervening sequence between the homology arms may contain one or more of a selection cassette, a reporter protein, a stop codon, or an intron. Homology targeting vectors and their use for genome targeting are known in the art as described in, e.g., Wefers et al (2011)), *Current Protocols in Mouse Biology*, 199-211.

In some embodiments, the recombinant mammalian cells described herein are pluripotent stem cells, e.g., mouse embryonic stem cells (mESCs), mouse induced pluripotent stem cells (miPSCs), human embryonic stem cells (hESCs), or human induced pluripotent stem cells (hiPSCs). Recombinant pluripotent stem cells comprising the Ref polypeptides described herein are particularly advantageous for gene targeting applications, as such cells following gene targeting events can then be differentiated into a number of genetically modified primary cell types incorporating a modified genomic locus.

III. Methods

Also described herein are methods for cleaving a DNA duplex within a target-defined nucleotide sequence using one of the Ref polypeptides described herein. Accordingly, in a first aspect, the invention encompasses a method of cleaving a duplex DNA molecule at a target nucleotide sequence using one of the Ref polypeptides described herein. In some embodiments, the method includes the steps of (i) providing a complex of a RecA protein, a double stranded DNA, and a targeting oligonucleotide comprising a sequence homologous to a target sequence found within the double stranded DNA; and (ii) contacting the complex from (i) with a purified Ref polypeptide comprising an amino acid sequence at least 95% identical to any of SEQ ID NOs:4 and 5, where the following conditions are met: (a) the purified Ref polypeptide does not comprise the entire amino acid sequence of a naturally occurring full length Ref protein; SEQ ID NO:1; or SEQ ID NO:2; in that a section of the n-terminal end of the sequence has been deleted; and (b) the purified Ref polypeptide exhibits an increased nuclease site-specific targeting activity relative to nuclease site-specific targeting activity of a naturally occurring full length wildtype Ref, or a Ref comprising the amino acid sequence of any of SEQ ID NOs:1-2.

The duplex (double stranded) DNA molecule that is cleaved is limited only in that it is a double-stranded DNA molecule, meaning that is contains two DNA strands that have complementary nucleotide sequences, with each strand aligned in an antiparallel direction relative to the other strand (3'-5' versus 5'-3'). The duplex DNA that is cleaved using the method is not limited by the surrounding environment or by any associated structures. Accordingly, the method can be used in any environment, including without limitation in an in vitro, in situ, in vivo, or ex vivo environment. The duplex DNA may be associated with one or more DNA-binding proteins, including histones and other proteins that are known to facilitate the formation of DNA-protein complexes.

The method includes the step of assembling a complex between (a) a targeting oligonucleotide comprising a nucleotide sequence that is homologous to a target nucleotide sequence of a duplex DNA molecule and (b) a RecA protein, a RecA protein homolog, or a polypeptide having at least 95% sequence identity to a RecA protein. This step may be performed in any setting known in the art, including without limitation an in vitro, ex vivo, in vivo, or in situ setting.

Formation of this complex further requires the presence of $Mg^{2+}$ or $Mn^{2+}$ ion, and ATP or an ATP analog. This step may be performed in any setting known in the art, including without limitation an in vitro, ex vivo, or in vivo or in situ setting. The duplex DNA molecule has a target nucleotide sequence that is homologous to a nucleotide sequence of the DNA targeting fragment at the location where DNA duplex molecule is to be cleaved, but is not otherwise limited. The DNA duplex molecule may be linear or circular, and may be genomic or non-genomic. The DNA molecule may be of viral, prokaryotic, eukaryotic, or synthetic origin, and optionally may be purified before being used in the method.

Since the RecA-promoted D-loop formation reaction is highly dependent on sequence identity, we anticipate that no more than two nucleotide mismatches can be tolerated within a 30 nucleotide DNA target. The sequence of interest is at the location where the duplex DNA molecule is to be cleaved. The actual cleavage sites include sequences near the 3' end of the targeting DNA segment. Preferably, the targeting fragment is 30-1,000 nucleotides long; more preferably, it is 60-1,000 or 90-1,000 nucleotides long. More preferably, the targeting fragment is from 60-150 or from 100-140 nucleotides long.

The targeting oligonucleotide may be initially double-stranded and rendered single-stranded using a variety of techniques, including without limitation (a) heat denaturation, (b) asymmetric PCR, or (c) specific degradation of the complementary strand by nucleases using a procedure that blocks the degradation of the desired strand, or by the combined activity of a nuclease/helicase combination. Alternatively, the targeting oligonucleotide may be created as a single-stranded molecule. Methods of synthesizing small single-stranded oligonucleotides are well-known in the art, and oligonucleotides having a specified sequence can also be custom ordered from a variety of commercial sources.

It is preferred that the RecA protein used in the method is either *E. coli* (strain K12) RecA protein (Uniprot sp P0A7G6) having the amino acid sequence of SEQ ID NO:12, or the mutated RecA protein (RecAE38K) having the amino acid sequence of SEQ ID NO:13.

Homologs of *E. coli* RecA protein can also be used in the method. By homolog, we mean a protein putatively derived from a common ancestor that performs the same function as RecA in other bacterial species or related families. Non-limiting examples of RecA homologs known in the art include the RecA proteins from *Deinococcus radiodurans*, having the amino acid sequence of SEQ ID NO:14 (NCBI Accession No. BAA21330; Version BAA21330.1) and the RecA protein from *Pseudomonas aeruginosa*, having the amino acid sequence of SEQ ID NO:15 (NCBI Accession No. ACT64220; Version ACT64220.1):

```
                                              (SEQ ID NO: 14)
MSKDATKEISAPTDAKERSKAIETAMSQIEKAFGKGSIMKLGAESKLD

VQVVSTGSLSLDLALGVGGIPRGRITEIYGPESGGKTTLALAIVAQAQ

KAGGTCAFIDAEHALDPVYARALGVNTDELLVSQPDNGEQALEIMELL

VRSGAIDVVVVDSVAALTPRAEIEGDMGDSLPGLQARLMSQALRKLTA

KILSKTGTAAIFINQVREKIGVMYGNPETTTGGRALKFYASVRLDVRI

GQPTKVGNDAVANTVKIKTVKNKVAAPFKEVELALVYGKGFDQLSDLV

GLAADMDIIKKAGSFYSYGDERIGQGKEKTIAYIAERPEMEQEIRDRV

MAAIRAGNAGEAPALAPAPAAPEAAEA (SEQ ID NO: 15)
ERQFGKGAVMRMGDHERQAIPAISTGSLGLDIALGIGGLPKGRIVEIY

GPESSGKTTLTLSVIAEAQKQGATCAFVDAEHALDPDYAGKLGVNVDD

LLVSQPDTGEQALEITDMLVRSNAVDVIIVDSVAALVPKAEIEGEMGD

AHVGLQARLMSQALRKITGNIKNANCLVIFINQIRMKIGVMF
```

Another example, the RecA protein derived from *Neisseria gonorrhoeae*, having the amino acid sequence of SEQ ID NO:16 (NCBI Accession No. AAB49193; Version AAB49193.1), is fully functional as a co-nuclease for a Ref polypeptide described herein.

```
                                              (SEQ ID NO: 16)
AIMKMDGSQQEENLEVISTGSLGLDLALGVGGLPRGRIVEIFGPESS

GKTTLCLEAVAQCQKNGGVCAFVDAEHAFDPVYARKLGVKVEELYLS

QPDTGEQALEICDTLVRSGGIDMVVVDSVAALVPKAEIEGDMGDSHV

GLQARLMSQALRKLTGHIKKTNTLVVFINQIRMKIGVMFGSPETTTG

GNALKFYSSVRLDIRRTGSIKKGEEVLGNETRVKVIKNKVAPPFRQA

EFDILYGEGISWEGELIDIGVKNDIINKSGAWYSYNGAK
```

The method also includes the use of RecA polypeptide variants having at least 90% sequence identity over the full length of any of the above-mentioned Rec protein sequences, e.g., at least 92%, 93%, 95%, 96%, 97%, 99%, or another percent sequence identity from at least 90% to 100% identical to the foregoing Rec protein sequences. We envision that other RecA mutants in addition to RecAE38K that are more effective than the wild type RecA protein can be created and can substitute for the RecA protein in the method described herein. Procedures for creating and screening such mutants are well known in the art.

The method additionally includes the step of contacting any of the Ref polypeptides disclosed herein excluding naturally occurring, full length Ref proteins. Specifically, in the disclosed Ref polypeptides, a section of the n-terminal end of the naturally occurring, full length Ref proteins has been deleted. In some embodiments, the Ref polypeptide to be used comprises an amino acid sequence at least 95% identical to any of SEQ ID NOs:4-11. In other embodiments, the Ref polypeptide to be used in the method comprises the amino acid sequence of any of SEQ ID NOs:4-11. In yet other embodiments, the amino acid sequence of the Ref polypeptide to be used consists of the amino acid sequence of any of SEQ ID NOs:4-11. The Ref polypeptide contact step may be performed in any setting known in the art, including without limitation an in vitro, ex vivo, or in vivo or in situ setting.

When the steps are performed as described, the duplex DNA molecule is cleaved at the target nucleotide sequence. Although it is preferred that the above-described steps are performed in the order presented above, performing the steps in this order is not essential to the cleavage of that duplex DNA molecule. Thus, the described steps may be performed in any order. Furthermore, the step using the RecA protein, homolog or variant, and the step using a Ref protein, homolog or variant may be performed at the same time. In such embodiments, a fusion protein encompassing both the RecA protein, homolog or variant, and the Ref protein, homolog or variant may be used in the method.

Successful cleavage of the duplex DNA molecule further requires the presence of ATP and a divalent metal ion. Preferably, the divalent metal ion is $Mg^{2+}$ or $Mn^{2+}$; more preferably, the divalent metal ion is $Mg^{2+}$. Accordingly, one or more of the steps described above may be performed in the presence of ATP and/or a divalent metal ion. The divalent metal ion is preferably $Mg^{2+}$ or $Mn^{2+}$ and is more preferably $Mg^{2+}$.

Preferably, one or more of the steps is performed in a suitable buffer. A preferred buffer has a pH of 6.5 to 8.5 and magnesium ion concentration of 3-12 mM and may contain ATP or dATP and an ATP regeneration system (e.g., Phosphoenolpyruvate and pyruvate kinase, or creatine phosphate and creatine kinase). Recipes for preferred buffers are described, for example, in Gruenig et al (2011), *J Biol Chem*, 286, 8240-8251.

The compositions and methods disclosed herein will facilitate the cleavage of double-stranded DNA in a directed manner not provided by any other technique currently known in the art. As a research tool, the methods and kits can be used for directed ex vivo DNA cleavage, and could also be used to create eukaryotic or bacterial cell gene knockouts or transgenic organisms for use in research.

The methods and kits may also be used therapeutically. For example, the methods and kits could be used to digest HIV gene sequences embedded in a human genome. Because the disclosed Ref variant polypeptide/RecA endonuclease system and associated method can be targeted to any genomic sequence by using a specific single-stranded DNA targeting fragment homologous to a targeted genome sequence, any specific genome sequence can be targeted for inactivation or removal using the same Ref/RecA system/method.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Methods for Generation and Analysis of N-Terminal Truncation Variants of Ref Proteins Introduction Recently, the P1 bacteriophage Ref protein was identified as a RecA-dependent, HNH-like endonuclease (Gruenig et al 2011, *J Biol Chem*, 286:8240-8251). In the presence of RecA, ATP, and $Mg^{2+}$, Ref produces extensive degradation of single-stranded (ss) DNA. More importantly, Ref will cleave both strands of the targeted DNA within a D-loop formed with RecA, creating double-strand breaks (DSBs) within a small target area.

The early in vitro targeting assay employs M13mp18 circular dsDNA (cdsDNA) and a homologous single-stranded 150-mer oligonucleotide. RecA forms a nucleoprotein filament on the oligonucleotide and initiates strand invasion in the homologous region of the cdsDNA. Strand invasion creates a D-loop. Ref then cleaves both strands of the targeted duplex DNA within the D-loop region. Recent work in the lab has elucidated that Ref creates targeted DSBs in the D-loop in two sequential nicking steps in a RecA-dependent manner (manuscript in prep). Ref first nicks the strand paired to the oligonucleotide, followed by nicking of the displaced strand. These two reactions exhibit somewhat different requirements, suggesting mechanistic distinctions (manuscript in prep).

We have continued to pursue a more thorough characterization of the Ref protein. The crystal structure of the C-terminal domain of Ref was determined to 1.4 Å. The N-terminal 76 amino acids are disordered in the crystal structure, leading us to investigate the importance of this domain in Ref functions such as DNA binding, oligomerization, and nuclease activity. Previous work on the P1 ΔN76 Ref protein determined that at least part of this domain is necessary for DNA binding. Although a complete N-terminal deletion still retains nuclease activity, a 100× higher concentration is needed to reach wild type cleavage levels. The N-terminal region is highly charged with 25 positive and nine negative charges. Upon, analysis of the N-terminal charges, we identified a pattern in the distribution of the charged amino acid residues. We interpreted this as a potential signature charge distribution motif that we decided to utilize in a directed effort to dissect the function of the N-terminal region of Ref. An understanding of N-terminal domain function is critical to further development of the Ref system in biotechnology applications.

Since the Ref protein can be targeted to a specific sequence via an oligonucleotide, this system has potential to contribute to the toolbox available for genomic editing. The Ref system is not limited by any target DNA sequence constraints. Due to the length of the oligonucleotide employed, nonspecific cleavage of off-target sites should be minimal or absent. It would retain some advantages of CRISPR systems in that the nuclease utilized is always the same. However, the guide would be DNA instead of RNA. In order to optimize Ref protein function for all applications, a more complete characterization of the protein is necessary. In the following, we address the importance of the N-terminal 76 amino acids, provide evidence for Ref dimerization, and provide engineered truncation variants that have optimized activity for creating targeted DSBs.

Materials and Methods:

DNA Substrates.

The M13mp18 circular ssDNA (7249 nucleotides) was prepared as described previously (Messing 1983, *Methods in Enzym.*, 101:20-78; Neuendorf et al 1986, *J Biol Chem.*, 261:8276-8282). The concentration of circular ssDNA was determined by absorbance at 260-nm using 108 µM nt $ml^{-1}$ $A260^{-1}$ as the conversion factor. The M13mp18 circular dsDNA was prepared as described previously (Messing, Neuendorf, supra). The concentration of circular dsDNA was determined by absorbance at 260-nm using 151 µM nt $ml^{-1}$ $A260^{-1}$ as the conversion factor. All DNA concentrations are given in µM nucleotides (µM nt). Oligonucleotides were purchased from Integrated DNA technologies. Sequences of oligonucleotides used in this study are as follows:

rlbl 150 mer (SEQ ID NO: 17):
5'-TTTTGGTTTTTATCGTCGTCTGGTAAACGAGGGTTATGATAGTGTT

GCTCTTACTATGCCTCGTAATTCCTTTTGGCGTTATGTATCTGCATTAG

TTGAATGTGGTATTCCTAAATCTCAACTGATGAATCTTTCTACCTGTAA

TAATGT-3'

AJM25 71 mer (SEQ ID NO: 18):
5'-56FAM/CAGAAGTAAGTTGGCCGCAGTGTTATCACTCATGGTTATG

GCAGCACTGCATAATTCTCTTACTGTCATGC-3'

AJG52 71 mer-(SEQ ID NO: 19)
5'GCATGACAGTAAGAGAATTATGCAGTGCTGCCATAACCATGAGTGAT

AACACTGCGGCCAACTTACTTCTG-3'

Proteins:

The *E. coli* RecA E38K protein was purified as described previously (Lusetti et al 2003, *J Biol Chem*, 278:16381-16388) with the following modifications. After washing the protein pellet with 20 mM Tris-Cl (80% cation), pH 7.7, 1 mM EDTA, 10% glycerol (R buffer), the pellet was resuspended containing 1 M $NH_4(SO_4)_2$ and applied to a butyl-Sepharose (Amersham Biosciences) column. The sample was eluted with a linear gradient from R buffer plus 1 M $NH_4(SO_4)_2$ to R buffer. RecA E38K fractions were pooled and dialyzed into P buffer (20 mM phosphate, pH 7.0, 1 mM EDTA and 10% glycerol). The protein was loaded onto a ceramic hydroxyapatite (Bio-Rad) column as in the previous reference, but with the linear gradient from 20-500 mM P buffer. The fractions were dialyzed against R buffer and loaded on to a Source 15Q column. RecA E38K was eluted with a linear gradient from no salt to 1 M KCl. Peak fractions were identified as above, pooled, and dialyzed against R buffer. The pooled fractions were loaded onto a DEAE sepharose column and eluted with a linear gradient from R buffer to R buffer plus 1 M KCl. The peak fractions were identified and pooled as above, precipitated with ammonium sulfate (45% final concentration), and resuspended in R buffer plus 1 M KCl. The protein was applied to a HiPrep 16/60 Sephacryl S-300 (Amersham Biosciences) column equilibrated in R buffer plus 1 M KCl. RecA E38K was precipitated with $NH_4(SO_4)_2$ as above, and resuspended in R buffer plus 1 M ammonium sulfate. The protein was loaded on a butyl sepharose column and eluted in a linear gradient to R buffer. The fractions were identified, pooled, and precipitated as above and dialyzed against R buffer. The protein was flash frozen in liquid N2 and stored at −80° C. The concentration of the purified RecA protein was determined from the absorbance at 280 nm using the extinction coefficients of $2.23 \times 10^4$ $M^{-1}$ $cm^{-1}$.

Cloning, Overexpression, and Purification of Ref and Ref Variants:

φW39 wild type Ref was made by mutagenesis of pEAW584, which is wild type P1 Ref in the protein expression vector pET21A (Novagen). The mutations were I8L, C11R, K13E, V34A, T46S, L47I, R86T, A93T, N107E, and A115S. Silent mutations to improve codon usage were also made and the resulting plasmid is pTMO9. TMO hybrid Ref vector is PTMO8, which is P1 Ref, in pET21A, with mutations at I8L, C11R, K13E, V34A, T46S, L47I, N107E, and A115S. It lacks the R86T and A93T mutations found in φW39 wild type Ref. φW39 ΔN74 Ref-pTMO9 was used as the template in a PCR with an upstream primer consisting of a NdeI site followed by bases 175-202 of phiW39 ref, with a G to T change at base 192 to make a silent mutation for better codon use at aa 64. The ATG bases included in the NdeI site code for the first Met codon of the gene. The downstream primer consists of a BamHI site followed by bases 544-561 of the φW39 ref gene in 5' to 3' orientation. The PCR product was digested with NdeI and BamHI and inserted into pET21A digested with the same enzymes. The resulting plasmid was directly sequenced to confirm the presence of φW39 ΔN74 Ref. φW39 ΔN47 Ref-pEAW865 was constructed in the same manner as pEAW885 except the upstream primer consisted of bases 142-154 of phiW39 ref, with a C to T change at base 147 to make a silent mutation for better codon use at aa 49. φW39 ΔN21 Ref-pEAW886 was constructed in the same manner as pEAW885 except the upstream primer consisted of bases 64-101 of φW39 ref, with several changes for improved codon usage.

The P1 wild type Ref and P1 ΔN76 proteins were purified as described previously (Gruenig et al 2011, supra) and concentration was determined using an extinction coefficient of $2.851 \times 10^4$ $M^{-1}$ $cm^{-1}$ and $1.5220 \times 10^4$ $M^{-1}$ $cm^{-1}$, respectively.

The φW39 wild type Ref and φW39 ΔN74 Ref were purified with procedures using similar growth, induction, cell harvesting, and early fractionation steps as P1 wild type Ref. Both of these overexpression vectors were transformed into BL21(DE3) cells. Purification entailed polyethyleneimine precipitation and pellet extraction, precipitation with $(NH_4)_2SO_4$, and chromatography successively using butyl-Sepharose (120 mL CV), Source 15 Q, Source 15S, and Sephacryl S-100 gel filtration columns. This was followed by another butyl-Sepharose (20 mL CV) chromatography step. After the first butyl-Sepharose column, the protease inhibitor Pefabloc SC (Sigma) was added to 0.1 mg/ml final concentration. Concentration was determined using an extinction coefficient of $2.788 \times 10^4$ $M^{-1}$ $cm^{-1}$ for φW39 wild type and $1.5220 \times 104$ $M^{-1}$ $cm^{-1}$ for φW39 ΔN74.

The φW39 ΔN21 Ref and φW39 ΔN47 Ref were purified similarly to the above proteins with two major modifications: both of these overexpression vectors were transformed into BLR (DE3) cells which prevents RecA contamination during the purification and the last butyl-sepharose chromatography step was omitted. Concentration was determined using an extinction coefficient of $2.219 \times 10^4$ $M^{-1}$ $cm^{-1}$ for φW39 ΔN21 and $1.5220 \times 10^4$ $M^{-1}$ $cm^{-1}$ for φW39 ΔN47. All proteins were stringently tested for exonuclease and endonuclease contamination and all were free from detectable nuclease activity in the absence of RecA protein.

Fluorescence polarization DNA binding assay—Ref (or a variant) at 0.5-10,000 nM was incubated with 2 nM AJM25 71mer ssDNA or AJM25 annealed with AJG52 71mer to make dsDNA substrate in 25 mM Tris-acetate (pH 8.5), 3 mM potassium glutamate, 15 mM magnesium acetate, and 5% w/v glycerol at room temperature for 15 minutes. Fluorescence anisotropy (FA) was measured at 25° C., using a Tecan Infinite M1000 instrument with 470-nm excitation and 535-nm emission wavelengths for at least three replicates; the average FA values were plotted with one standard deviation of the mean shown as error. Prism software was used to convert FA values to the fraction of DNA bound and apparent dissociation constants were the Ref concentration (or variant) needed for 50% binding saturation.

Gel Filtration Chromatography:

All Ref variants (~100-150 µM) were applied to a Superdex 200 10/300 GL column pre-equilibrated with 20 mM Tris-HCl (pH 7.5), 0.1 mM EDTA, 10% glycerol, 200 mM KCl and run at 4° C. at a flow rate of 0.5 ml/min. Standards used to calibrate the column: Cytochrome C (12.4 kDa), Carbonic anhydrase (29 kDa), Alcohol dehydrogenase (150 kDa), and Apoferritin (443 kDa). The calibration curve was used to calculate the molecular masses of each Ref variant by interpolating elution volumes onto the curve.

Circular ssDNA Nuclease Assay:

Reactions were incubated with Buffer A (containing 25 mM Tris-acetate (pH 8.5), 3 mM potassium glutamate, 15 mM magnesium acetate, and 5% w/v glycerol), an ATP regeneration system (10 U/mL pyruvate kinase and 3.5 mM phosphoenolpyruvate), 4 µM nt M13mp18 cssDNA, and 2.4 µM RecA E38K at 37° C. for 10 min. Reactions were incubated an additional 15 min with 3 mM ATP to allow an active RecA nucleoprotein filament to form prior to the addition of Ref at 24 nM. After 20 min, 20 µL of the reaction mixture were added to 10 µL, of stop solution (9% Ficoll, 0.25% bromphenol blue, 0.25% xylene cyanol, and 4% SDS) then incubated another 30 min at 37° C. Samples were analyzed by electrophoresis in 0.8% agarose gel with TAE buffer (40 mM Tris-Acetate, 1 mM EDTA), stained with SYBR gold, and visualized using the SYBR gold settings on a Typhoon FLA 9000 (GE Healthcare).

Nuclease Site-Specific Targeting Assay:

The reactions were carried out at 37° C. in buffer A, (containing 25 mM Tris-acetate (pH 8.5), 1 mM DTT, 3 mM potassium glutamate, 15 mM magnesium acetate, and 5% w/v glycerol) and an ATP regeneration system (10 U/mL pyruvate kinase and 3.5 mM phosphoenolpyruvate. The above components were incubated for 10 minutes with a targeting oligonucleotide (4 µM nt, rlb1 150mer) and RecA E38K (1.33 µM). ATP (3 mM) was added and incubated an additional 20 minutes, followed by M13mp18 circular dsDNA (8 µM nt) and another 20 minute incubation. Before adding Ref, a zero time point was taken, then Ref (100 nM) was added. The reactions were stopped at the noted time points by removing 20 µL from the reaction and adding it to 20 µL of stop solution (12 mM Tris acetate pH 7.5, 10.8% (w/v) Ficoll, 0.15% (w/v) each bromophenol blue and xylene cyanol, 8% SDS) and incubating at 37° C. an additional 30 minutes. Samples were analyzed by electrophoresis on a 0.8% agarose gel with TAE buffer, stained with SYBR Gold stain, and imaged using the SYBR gold settings on a Typhoon FLA 9000 (GE Healthcare). Gel image was analyzed using ImageQuant TL software (GE Healthcare). Lanes were normalized for loading conditions by reporting individual band intensity as a percentage of the total band intensity in that lane.

Example 2

Charge Distribution in the Ref N-Terminal Region Displays a Signature Charge Pattern The bacteriophage P1 Ref protein creates double-strand breaks within a D-loop created by a RecA filament (Gruenig et al 2011, supra). In this study, we characterize the function of the inherently unstructured N-terminal 76 amino acids of Ref.

An examination of sequence databases revealed very few homologs of P1 Ref protein, essentially all of them encoded by bacteriophages or cryptic bacteriophage remnants closely related to P1. We first examined the Ref proteins encoded by phages φW39 and P7 in hope of finding a more efficient targeting nuclease. The P7 Ref protein has 13 amino acid changes in comparison to wild type P1 Ref and an additional 30 amino acids on the C-terminus. Unfortunately, the wild type P7 Ref protein was found to be insoluble in several conditions tested (unpublished data). The wild type φW39 Ref has ten amino acid changes in comparison to the P1 Ref (6 of these in the unstructured N-terminus), but no additional C-terminus region. Lab stocks of φW39 bacteriophage were unavailable, so DNA cloning techniques were used to mutate the gene encoding P1 Ref to the reported sequence of φW39 Ref Sequence alignment of these two proteins (FIG. 1A) identifies the ten amino acid differences between the two proteins. Also included in the alignment is a variant we refer to as the TMO hybrid Ref protein, which was serendipitously cloned and purified. The TMO hybrid was an intermediate in the construction of the φW39 Ref. Of the four amino acid residues in the C-terminal core domain that differ between the two proteins, the TMO hybrid has only two of the changes characteristic of the conversion of P1 Ref to φW39 Ref, N107E and A115S (FIG. 1A). The TMO hybrid also lacks 47 amino acid residues from the amino terminus, due to a precise but apparently spontaneous degradation that occurred during purification. Following this purification, we looked more closely at the N-terminus region to determine if there was a pattern in charge distribution that might signal substructure and/or might explain the spontaneous deletion. We found a signature charge pattern (++ + +-+) repeated three times as shown below the N-terminus sequence in FIG. 1B. Using this pattern as a guide, we cloned a series of specific truncation variants that removed one or more of these putative motifs (FIG. 1B). The Ref protein truncations purified included φW39 ΔN21, φW39 ΔN47, and φW39 ΔN74. The P1 ΔN76 Ref that was previously purified (Gruenig et al 2011, supra) was included in many assays for comparison purposes (FIG. 1C). Protease inhibitors were used to prevent any further spontaneous degradation during purification. The molecular weight of each variant was verified by mass spectrometry following purification and each variant exhibited normal folding and solubility.

Example 3

N-Terminal Domain Truncated Variants of Ref Up to Residue 47 Retain DNA Binding

Figure 2:
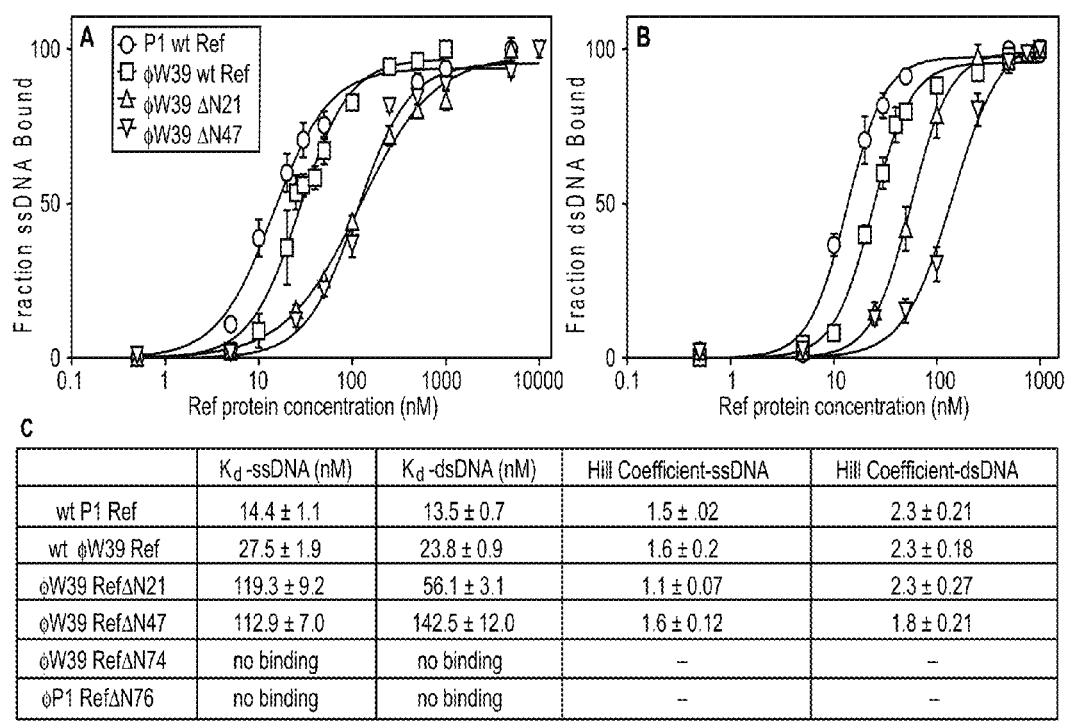
FIG. 2 shows equilibrium binding isotherms of wild type Refs and truncations in presence of labeled ssDNA or dsDNA as monitored by fluorescence anisotropy. All data are the average of at least three experiments. Error bars are one standard deviation from the mean. (A) φW39 ΔN21 Ref and φW39 ΔN47 Ref show reduced affinity for ssDNA in comparison to wild type Refs. (B) φW39 ΔN21 Ref and φW39 ΔN47 Ref also show a decreasing affinity for dsDNA as more of the N-terminus is removed in comparison to wild type Refs. (C) Table of apparent $K_D$ values and Hill coefficients for each Ref protein analyzed from at least three replicates. No DNA binding was observed with the φW39 ΔN74 Ref or P1 ΔN76 Ref.

Previous work had shown that the P1 ΔN76 Ref truncation protein no longer exhibited any DNA-binding activity, indicating that at least part of the N-terminal 76 amino acids are necessary for DNA binding. Fluorescence polarization assays with labeled DNA substrates (ssDNA and dsDNA) were carried out to determine dissociation constants of each of the N-terminal domain truncations. When assayed with a labeled 71mer ssDNA (AJM25), the full-length wild type P1 and φW39 Ref proteins exhibited similar KD values of 14.4 nM and 27.5 nM, respectively (FIG. 2A, 2C). However, the φW39 ΔN21 and φW39 ΔN47 Ref proteins showed about a 6-fold reduction in binding with KD values of 119.3 nM and 112.9 nM, respectively (FIG. 2A, 2C). The φW39 ΔN74 and P1 ΔN76 Ref proteins showed no DNA binding (FIG. 2C). For the P1 ΔN76 Ref protein, this is consistent with EMSA data from the earlier study (Gruenig et al 2011, supra). This indicates that at least 47 amino acids can be removed from the N-terminal Ref without completely eliminating DNA binding, whereas deletion of 74 N-terminal residues completely abolishes DNA binding. This indicates the presence of a critical sequence domain between residues 47-74.

The truncations were also assayed with 71mer dsDNA substrate. The dsDNA substrate was made by annealing the labeled 71mer oligonucleotide (AJM25) with the complementary 71mer oligonucleotide (AJG52). Again the full-length, wild type P1 and φW39 Ref proteins exhibited very similar binding constants of 13.5 nM and 23.8 nM respectively (FIG. 2B, 2C). Binding affinity for dsDNA was not entirely retained for φW39 ΔN21 Ref (56.1 nM) and φW39 ΔN47 Ref (142.5 nM), as was observed for ssDNA. Instead, an increase in KD is seen as more of the N-terminus is truncated (FIG. 2B, 2C). Also, there is an apparent cooperativity when binding to dsDNA, and this cooperativity decreases as the N-terminus is truncated (FIG. 2C). This provides evidence that the N-terminal region of Ref is necessary for DNA binding. Specifically, the amino acids between position 47 and 74 are particularly important. Interestingly, one of the signature amino acid charge patterns described above is present in this area.

Example 4

Figure 3:
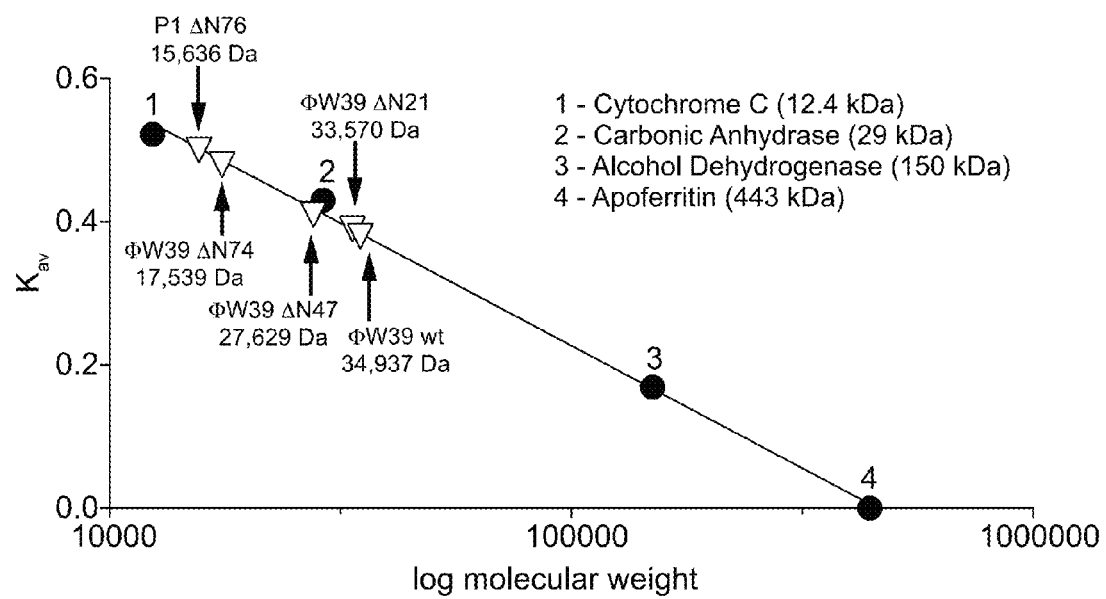
FIG. 3 shows a graph of a gel filtration elution profile of full-length φW39 Ref and truncation variants. Standards used to generate the elution volume standard curve are shown. Gel filtration results were verified by ultracentrifugation. The data shown illustrate that full-length wild type φW39 Ref, φW39 ΔN21 Ref, and φW39 ΔN47 Ref are dimers in solution, while the φW39 ΔN74 Ref and P1 ΔN76 Ref are monomeric.

N-Terminal Domain Truncated Variants of Ref Up to Residue 47 are Competent to Form Oligomers We determined the oligomeric status of full-length Ref and all truncations in solution using gel filtration chromatography. Preliminary ultracentrifugation data suggested P1 wild type Ref to be a mixture of monomer and dimer, while the P1 ΔN76 was only observed in monomeric form (supplementary data). This led us to believe that the N-terminal unstructured region is also important for dimerization of the Ref protein. The elution profile of full-length wild type φW39 Ref (35 kDa) corresponds with a dimer using the calculated mass of 21.3 kDa, which was consistent with the ultracentrifugation data (FIG. 3). φW39 ΔN21 Ref and φW39 ΔN47 Ref both eluted from the column in dimeric form as well (33.6 kDa and 27.6 kDa respectively, FIG. 3). In contrast, the φW39 ΔN74 Ref and P1 ΔN76 Ref eluted at 17.5 and 15.6 kDa respectively, indicating that they were present in monomeric form (FIG. 3). Ultracentrifugation was carried out on all tested variants and all were consistent, except the φW39 ΔN74 Ref. This variant in the ultracentrifugation exhibited a higher order aggregation that potentially was a dimeric species. However, this species was much more difficult to detect and analyze than dimeric wild type Ref. The φW39 ΔN74 may retain some capability to dimerize. Overall, the data provides evidence that the residues between 47-74 play a significant role in the dimerization of Ref. The similarity of these results and the DNA binding results may indicate that dimerization and DNA binding are linked to some unknown extent.

Example 5

The N-Terminus of Ref is Necessary for ssDNA Degradation

Figure 4:
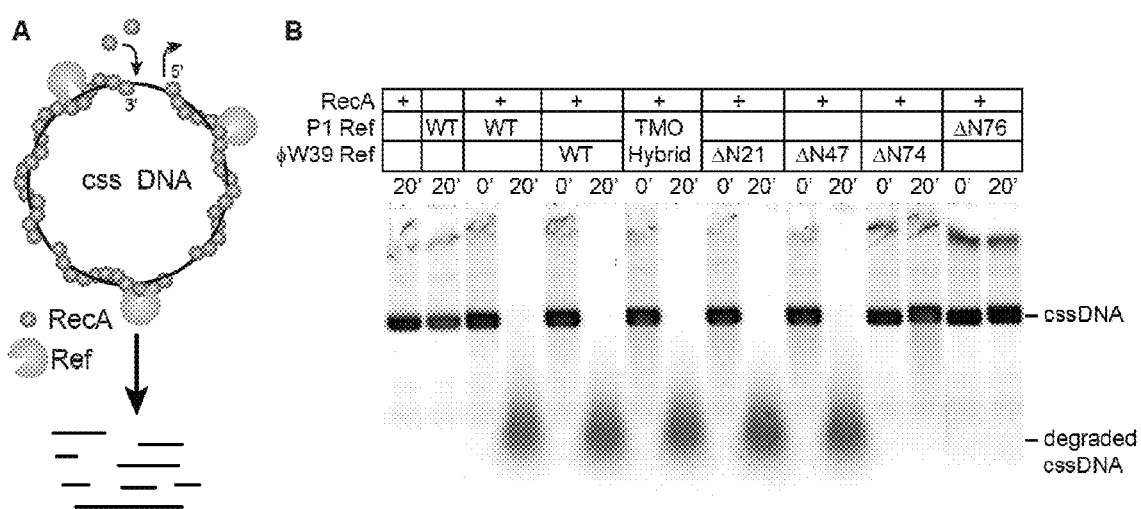
FIG. 4 shows (A) Schematic of Ref cssDNA nuclease assay. RecA E38K (2.4 uM) was incubated with M13mp18 cssDNA (uM nt) in Buffer A with an ATP regeneration system for 10 minutes. ATP (3 mM) was added to initiate the formation of an active RecA filament and incubated for 10 minutes, followed by the addition of 24 nM of each Ref variant for 20 minutes. (B) Agarose gel of reactions after 20 minute incubation of all Ref variants. All cssDNA is degraded within 20 minutes with full-length Ref (P1 and φW39), TMO hybrid, φW39 ΔN21, φW39 ΔN47 Ref. The φW39 ΔN74 Ref exhibits greatly reduced nuclease activity and P1 ΔN76 Ref does not show any nuclease activity at this concentration.

P1 Ref is a RecA dependent-nuclease on ssDNA (Gruenig et al 2011, supra). In the presence of M13mp18 circular ssDNA, RecA protein, ATP, and $Mg^{2+}$ there is extensive degradation of the DNA within twenty minutes. To test whether the truncations had any affect on nuclease activity, this assay was carried out on all truncation variants at the same concentration (24 nM). All proteins used were rigorously tested for exonuclease and endonuclease contamination following purification. In the presence of RecA only or Ref only there is no degradation of the ssDNA. After twenty minutes, the P1 wild type, φW39 wild type, φW39 ΔN21, and φW39 ΔN47 Ref all exhibited similar amounts of degradation (FIG. 4A). However, there was a dramatic decrease in the amount of nuclease activity with the φW39 ΔN74 Ref and almost no degradation with P1 ΔN76 Ref (FIG. 4A). When concentrations of φW39 ΔN74 were increased ten-fold or higher, levels of degradation similar to those produced by wild type Ref were obtained (data not shown). This indicates that the N-terminus is important for the nuclease activity of Ref. Again, it was the amino acids between residue 47 and 74 that appeared critical. The dramatic deficiency in the activity φW39 ΔN74 Ref and P1 ΔN76 Ref seems to coincide well with the deficient DNA binding and dimerization data.

Figure 5:
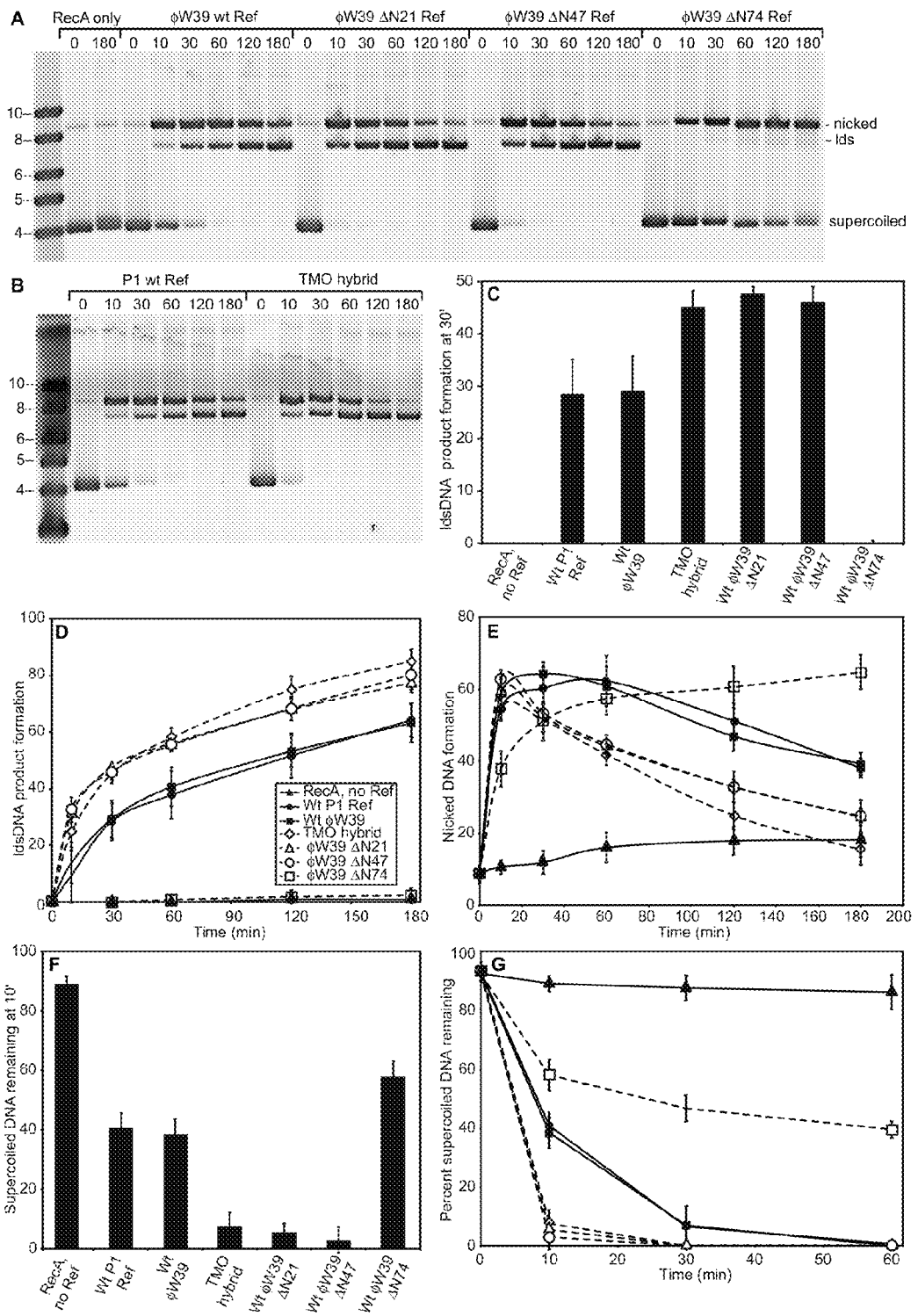
FIG. 5 (A) shows an agarose gel representing time points from the targeted nuclease assay with all Ref variants. Supercoiled DNA is the starting material (bottom band), which is converted first to nicked DNA (top band) and subsequently to linear DNA (middle band). RecA E38K (1.33 μM) was incubated with rlb1 oligonucleotide (4 μM nt) in Buffer A* with an ATP regeneration system for 10 minutes to form a RecA filament. ATP (3 mM) was added and incubated for 20 minutes, followed by the addition of M13mp18 circular dsDNA (8 μM nt). This was incubated for 20 minutes and a D-loop structure formed at the site of homology between the dsDNA and rlb1 oligonucleotide. Ref (100 nM) was added and DNA was cleaved within the D-loop. One nick by Ref results in nicked circular dsDNA, while two cuts results in ldsDNA. (B) shows an agarose gels representing time points from the targeted nuclease assay using the P1 wild type Ref and TMO hybrid Ref using same reaction conditions as above. (C) Quantification of ldsDNA product after 30 minutes. TMO hybrid Ref, φW39 ΔN21 Ref, and φW39 ΔN47 Ref all show almost two-fold greater product formation in comparison to wild type Ref (φW39 or P1). φW39 ΔN74 Ref is almost completely deficient in ldsDNA formation at this concentration. (D) Graphical representation of ldsDNA product formation over time of A averaged over at least three independent experiments. Throughout the time course TMO hybrid Ref, φW39 ΔN21 Ref, and φW39 ΔN47 Ref all show enhanced production of ldsDNA in comparison to wild type Refs. (E) Graphical representation of nicked product formation over time of A averaged over at least three independent experiments. Throughout the time course TMO hybrid Ref, φW39 ΔN21 Ref, and φW39 ΔN47 Ref all show faster nicking kinetics in comparison to wild type Refs. The φW39 ΔN74 Ref is proficient in nicking DNA, but shows slightly slower kinetics. (F) Quantification of disappearance of supercoiled substrate after 10 minutes. TMO hybrid Ref, φW39 ΔN21 Ref, and φW39 ΔN47 Ref are all at least five times more efficient at creating the first nick in comparison to wild type Ref (φW39 or P1). (G) Graphical representation of supercoiled DNA remaining over time of A averaged over at least three independent experiments. TMO hybrid Ref, φW39 ΔN21 Ref, and φW39 ΔN47 Ref are much more efficient at creating the initial nick early on, but by 30 minutes the wild type Refs are comparable to the truncations.

Some Ref truncation variants showed enhanced efficiency in double-strand break formation: The genomic engineering potential of Ref relies on nuclease activity being restricted to D-loops that are created by RecA. We have developed an in vitro assay to test Ref in this capacity as well as optimize the formation of targeted double-strand breaks for downstream applications (Gruenig et al 2011, supra). In this assay, Ref cleaves both strands of a duplex DNA at the site of a D-loop formed by RecA-coated oligonucleotide complementary to that site. The mechanistic details of this reaction are not completely understood. However, there is evidence that Ref protein nicks on the paired strand first and then creates a second nick in the opposite duplex strand (Ronayne, manuscript in prep). In the reaction, supercoiled M13mp18 dsDNA is incubated with a homologous 150-mer oligonucleotide and RecA protein, which pairs the homologous oligonucleotide and duplex DNA. The RecA E38K variant is used in all experiments because of an observed enhancement of nuclease activity relative to wild type RecA protein. Upon quantification of supercoiled DNA, nicked DNA product and linear double-stranded DNA (ldsDNA) product, we observed that the two wild type Ref proteins were identical in reaction kinetics with about 63% of supercoiled DNA being linearized after 3 hours (FIG. 5C). In comparison, the φW39 ΔN21, φW39 ΔN47, and TMO hybrid Ref shared similar kinetics and increased ldsDNA product formation by about 20% (FIG. 5C). The truncations showed faster kinetics such that at 30 minutes they produced about a two-fold increase in ldsDNA formation relative to the wild type proteins (FIG. 5B). These truncation variants seem to show enhanced ldsDNA product formation over wild type proteins primarily because of faster kinetics in making the first nick on supercoiled DNA. Here, the advantage of the truncation variants was even more evident. The amount of supercoiled DNA remaining after ten minutes is substantially different between the wild type Refs and the truncation variants (FIGS. 5E and 5F). The defining difference between the variants and wild type proteins seemed to be in the first ten minutes of the reaction. At ten minutes, the amount of supercoiled DNA remaining for the truncation variants was only 3-7%, however, 40% remained for the wild type proteins. This indicates that φW39 ΔN21, φW39 ΔN47, and TMO hybrid Ref have nicked the paired strand considerably faster, creating a greater amount of nicked intermediate. This eventually leads to faster formation of ldsDNA product.

The φW39 ΔN74 Ref was able to nick the first strand at a reduced rate. However, when used at the same concentration as the wild type Ref, it did not produce any ldsDNA product. If the concentration of φW39 ΔN74 was increased 50-fold, we observe almost the same amount of ldsDNA product formation as wild type Ref and similar nicking kinetics. This indicates that the DNA binding and dimerization deficiencies can be overcome by mass action of the protein.

This work leads to two significant conclusions about the function of the unstructured N-terminus of Ref. First, at least part of the N-terminal region is required for (a) Ref binding to DNA, (b) Ref dimerization, and (c) efficient Ref-mediated DNA cleavage. It is reasonable to suspect that these various functions are linked in some way. Second, removal of part, but not all of the N-terminus increases the efficiency of targeted Ref cleavage at D-loops created by the action of RecA protein. The most efficient Ref variants examined in this study lacked either 21 or 47 N-terminal amino acid residues. In contrast, removal of 74 N-terminal amino acid residues led to a dramatic decrease in Ref function as a targeting endonuclease.

Our data provides a first look at the function of the N-terminal, disordered region of the Ref protein. Removal of between 21 and 47 amino acid residues from the N-terminus represents at least part of an optimization strategy for creating targeted double-strand breaks in vitro with Ref. In the N-terminus, we have identified a possible motif consisting of a +.+...+.+-+ charge distribution pattern. This putative motif is found three times in the N-terminal region of Ref (FIG. 1B). If this motif has functional importance, the results indicate that removal of one repeat improves Ref function in the targeted cleavage assay, while removal of all three motifs creates notable deficiency in function. The critical region in which truncations may be beneficial likely falls between approximately residues 10 and 66.

The TMO hybrid, φW39 ΔN21, and φW39 ΔN47 all behaved very similarly, with enhanced activity in the targeted nuclease assay. One possible explanation for this observation is that since these proteins display a lower affinity for ssDNA, there may be less competition between RecA and Ref for binding to the oligonucleotide in the targeted assay. This allows for more RecA to remain as a stable filament on the oligonucleotide, which is essential for activation of Ref nuclease activity. In optimizing the targeted assay based on concentrations, pH, Mg+2 concentration, and Ref/RecA concentrations, it was found that higher concentrations of Ref actually cause a large reduction in the amount of double-strand breaks generated (Ronayne, unpublished data). Instead, it was determined that a substoichiometric amount of Ref (100 nM) in comparison to 1.33 μM of RecA was the optimized ratio to use. Also wt RecA has an apparent KD of ~133 nM on a similar DNA substrate used in the fluorescence polarization experiments. Wild type Ref proteins had an apparent KD ~20 nM, indicating they most likely have a higher binding affinity for ssDNA than RecA. However, the truncation variants all had ssDNA KD values ~120 nM, such that these variants may compete less well for DNA binding relative to RecA.

Example 6

Further Details and Additional Extensions of Examples 1-5

This Example reiterates and summarizes much of the data presented in Examples 1-5 above, while further extending the data to encompass additional truncated Ref variants and the results of additional experiments.

Abstract.

The bacteriophage P1 Ref (recombination enhancement function) protein is a RecA-dependent, HNH endonuclease. It can be directed to create targeted double-strand breaks within a displacement loop formed by RecA. The 76 amino acid N-terminal region of Ref is positively charged (25/76 amino acid residues) and inherently unstructured. Our investigation of N-terminal truncation variants shows this region is required for DNA binding, contains a Cys involved in incidental dimerization, and is necessary for efficient Ref-mediated DNA cleavage. Specifically, Ref N-terminal truncation variants lacking between 21 and 47 amino acids are more effective RecA-mediated targeting nucleases.

Significance.

The *Escherichia coli* RecA and bacteriophage P1 Ref system potentially expands the growing toolbox for genome-editing. Similar to CRISPR/Cas9, the RecA/Ref system uses an oligonucleotide guide to create targeted double-strand breaks. The present work provides key structure-function information that is essential to optimizing this system and focuses on the oligomeric form and the function of an unusual and inherently unstructured N-terminal DNA binding domain of Ref. We show that truncations in the N-terminal region lead to a more efficient targeted-nuclease activity, which can potentially contribute to optimization of the system.

Introduction.

An effort to characterize the bacteriophage P1 Ref protein as a suspected RecA-regulator protein led to our previous discovery of the Ref nuclease function. Ref has the novel property that it will only cleave DNA to which RecA protein is bound. In the absence of any cofactors or proteins, Ref will bind to both single-stranded DNA (ssDNA) and double-stranded DNA (dsDNA), but no DNA cleavage occurs. When RecA, ATP, and $Mg^{2+}$ are added, Ref produces extensive degradation of ssDNA. The ATP and $Mg^{2+}$ are required for an active RecA nucleoprotein filament, and this in turn is necessary for Ref nuclease activity. More importantly, Ref will create double-strand breaks (DSBs) in a small target area within a RecA formed displacement loop (D-loop). RecA forms a nucleoprotein filament on an oligonucleotide (100-150 nucleotides in length) and initiates strand invasion in the homologous region of a dsDNA. In strand invasion, the RecA-bound oligonucleotide base pairs to the complementary strand and the other strand of the duplex is displaced. Ref then cleaves the paired and displaced strands of the targeted duplex DNA in a sequential and ordered pathway within the D-loop region. The second cut on the displaced strand is produced at a much slower rate and is mechanistically distinct from the paired strand cut.

The structure of the C-terminal globular domain of Ref has been determined to 1.4-Å resolution (PDB ID: 3PLW). Electron density for the N-terminal region was absent, and the sequence of this domain exhibits recognized hallmarks of an inherently disordered region. The asymmetric unit of Ref contains a monomer and two stably bound $Zn^{2+}$ ions. The structure features an HNH domain defined by a ββα metal-binding core. Outside of this core element, HNH nucleases are structurally and catalytically diverse, including group I and II homing endonucleases, transposases, restriction endonucleases, and bacterial colicins. Colicins digest dsDNA non-specifically, while homing endonucleases create nicks or DSBs at specific DNA sequences. Ref does not exhibit any dominant sequence specificity, however there is a preference for a phosphodiester bond to the 5" side of a pyrimidine base.

Here, we characterize key aspects of structure-function in the Ref protein, with a focus on the active oligomeric form and the function of the inherently unstructured N-terminal 76 amino acids. Visual inspection of the sequence revealed a possible signature charge distribution motif, which was used to guide the design of N-terminal deletion variants. We demonstrate that partial removal of the N-terminal region provides enhancement in targeted Ref cleavage at D-loops.

Results.

A Repeating Pattern in the Charge Distribution in the N-Terminal Domain.

An examination of sequence databases revealed few homologues of the P1 Ref protein, essentially all of them encoded by bacteriophages or cryptic bacteriophage remnants closely related to P1. We investigated P1 Ref homologues from bacteriophages P7 and ϕW39 to determine if targeting efficiency could be increased. The ϕW39 Ref protein proved to be tractable, identical to P1 Ref in its RecA-dependence, and at least as active as P1 Ref in all RecA-dependent nuclease assays. The P1 and ϕW39 Ref enzymes are 95% identical in amino acid sequence. One difference at residue 11 ultimately helped define oligomeric properties. The two proteins are used interchangeably in this study, and the N-terminal deletion variants were constructed in ϕW39 Ref.

The P7 Ref protein has 13 amino acid changes in comparison to P1 WT Ref in the N-terminal and core domains, and also features an additional 30 amino acids on the C-terminus. It was insoluble in several conditions tested (unpublished data). The ϕW39 WT Ref has ten amino acid changes in comparison to the P1 Ref (6 of these in the unstructured N-terminus), but no additional C-terminal amino acid residues (FIG. 1A). Stocks of ϕW39 bacteriophage were unavailable. Therefore, the reported sequence of ϕW39 Ref was reconstructed by directed mutagenesis of the P1 ref gene. An intermediate in the construction of the ϕW39 Ref, referred to as the TMO hybrid Ref protein, is also included in this study and was serendipitously cloned and purified (FIG. 1A). Of the four amino acid residues in the C-terminal core domain that differ between the two proteins, the TMO hybrid has only two of the changes characteristic of the conversion of P1 Ref to ϕW39 Ref, N107E and A115S (FIG. 1A). The TMO hybrid also lacks 47 amino acid residues from the amino terminus, due to a precise but apparently spontaneous degradation event that occurred during purification.

Examining the N-terminus region more closely, we identified a potential signature charge pattern (++ + +-+) repeated three times as shown in FIG. 1B. This pattern guided the design of a series of specific truncation variants with one or more of these putative motifs removed (FIG. 1B). The Ref protein truncations purified included ϕW39 ΔN21, ϕW39 ΔN47, ϕW39 ΔN59, ϕW39 ΔN66, and ϕW39 ΔN74 (FIG. 1C). The P1 ΔN76 Ref that was previously purified was included in many assays for purpose of comparison. Protease inhibitors were used to prevent any further spontaneous degradation, and molecular weights were verified by mass spectrometry in all cases.

Removing Charge Motifs' in the N-Terminal Domain Decreases DNA Binding Affinity.

The P1 ΔN76 Ref no longer exhibits DNA-binding activity, indicating the N-terminus has a DNA binding role. We employed fluorescence polarization with labeled DNA to determine apparent dissociation constants ($K_{d,app}$), thereby measuring the DNA binding function of this domain. One key parameter needed to determine true $K_d$ values, the DNA binding site size of Ref, is currently unknown and may change with each truncation variant. Our data analysis was thus limited to reporting apparent $K_d$, $K_{d,app}$, values that provide a measure of relative DNA binding affinity.

Figure 6:
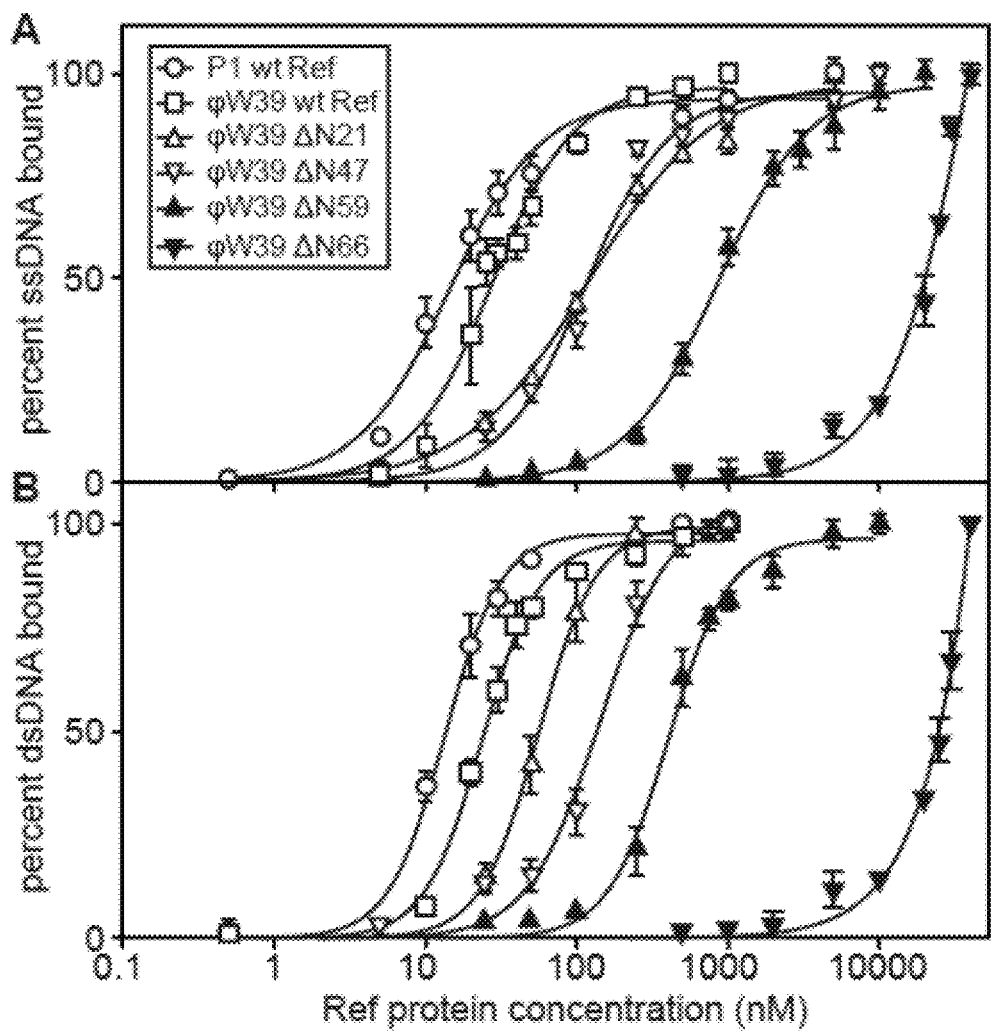
FIG. 6 shows Ref truncations have distinct affinities for ssDNA and dsDNA in comparison to wild type Ref. Equilibrium binding isotherms of WT Ref and truncations in presence of labeled ssDNA or dsDNA as monitored by fluorescence polarization. All data are the average of at least three experiments. Error bars are one standard deviation from the mean. (A) φW39 ΔN21 Ref and φW39 ΔN47 Ref show reduced affinity for ssDNA in comparison to WT Ref. (B) φW39 ΔN21 Ref and φW39 ΔN47 Ref also show a decreasing affinity for dsDNA as more of the N-terminus is removed in comparison to WT Ref. C) Table of apparent Kd,app values for each Ref protein analyzed from at least three replicates. No DNA binding was observed with the φW39 ΔN74 Ref or P1 ΔN76 Ref.

When assayed with a labeled 71mer ssDNA (AJM25), the full-length P1 WT and φW39 WT Ref proteins exhibited similar $K_{d,app}$ values (14±1 nM and 28±2 nM, respectively) (FIG. 6A, 6C). However, upon removing one putative charge motif, the φW39 ΔN21 and φW39 ΔN47 Ref proteins exhibited a six-fold reduction in binding (119±9 nM and 113±7 nM, respectively) (FIG. 6A, 6C). Removal of the second charge motif in the φW39 ΔN59 resulted in a 40-fold reduction in binding affinity.

The φW39 ΔN66, which has a partial deletion of the third motif, exhibited further reduction in ssDNA binding, and DNA saturation was not attainable. Upon removal of the third charge motif in φW39 ΔN74 and P1 ΔN76 Ref proteins, DNA binding was no longer detectable (FIG. 6C). For the P1 ΔN76 Ref protein, this is consistent with EMSA data from the earlier study. Our results suggest that each charge motif (or sequence features in or near these putative motifs) contributes to ssDNA binding.

The truncations were also assayed with a 71mer dsDNA substrate made by annealing the labeled 71mer oligonucleotide (AJM25) with the complementary 71mer oligonucleotide (AJG52). The P1 WT Ref and φW39 WT Ref proteins exhibited very similar $Kd_{app}$ (14±1 nM and 24±1 nM respectively) (FIG. 6B, 2C). Binding affinity for dsDNA was also reduced as the charge motifs were removed. However, φW39 ΔN21 Ref (56±3 nM) and φW39 ΔN47 Ref (143±12 nM) did not have similar $K_{d,app}$ values as seen with the ssDNA. As the second motif and part of the third motif were removed in the φW39 ΔN59 and φW39 ΔN66, dsDNA binding was further reduced. As with the ssDNA, φW39 ΔN74 and P1 ΔN76 Ref had no observable dsDNA binding. Overall we provide evidence that the N-terminal region of Ref is necessary for DNA binding, and the putative charge motifs may contribute collectively to that function.

Cys11 is Necessary for Disulfide Formation and Dimerization of Ref.

We determined the oligomeric status of full-length Ref and all truncations. Preliminary ultracentrifugation data suggested P1 WT Ref to be a mixture of monomer and dimer, while the P1 ΔN76 was only observed in monomeric form (unpublished data). We initially hypothesized that the N-terminal region is important for Ref dimerization.

Figure 7:
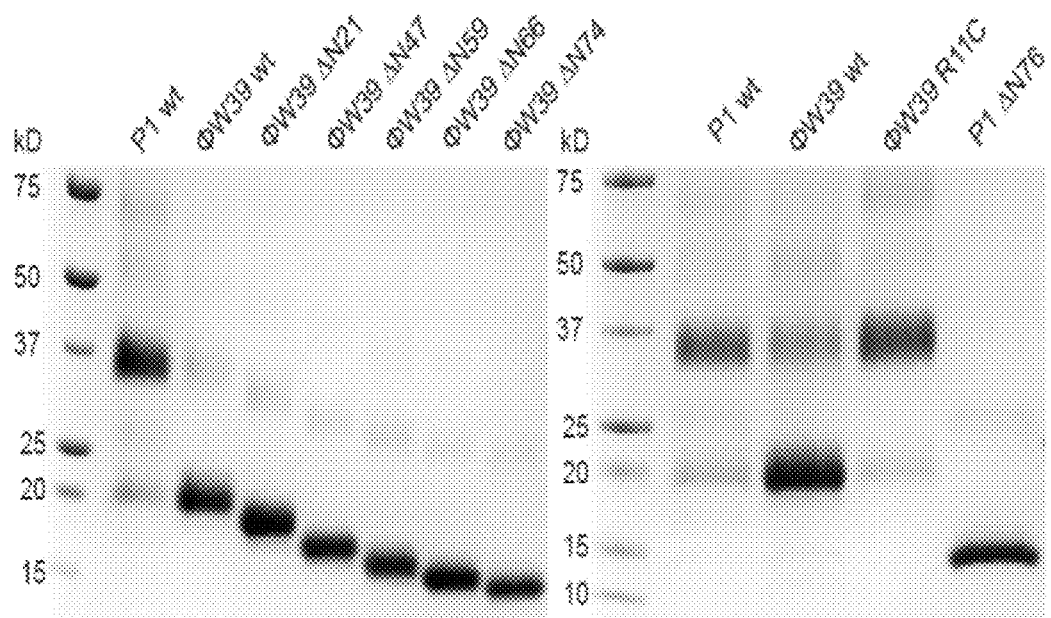
FIG. 7 shows SDS-PAGE of Ref truncations and variants after treatment with disuccinimidyl glutarate (DSG), a nonspecific primary amine crosslinker. The crosslinking covalently traps Ref in oligomeric states. P1 WT and φW39 R11C exhibit dimerization while WT φW39 Ref, φW39 ΔN21, φW39 ΔN47, φW39 ΔN59, φW39 ΔN66, φW39 ΔN74, and P1 ΔN76 show only background amounts of dimerization. Cys11 is responsible for dimerization of the P1 Ref protein.

Dimeric forms of P1 WT Ref were often observed on SDS-PAGE, but none of the truncated variants derived from φW39 Ref exhibited oligomeric properties. The non-specific crosslinker, disuccinimidyl glutarate (DSG), was used to covalently trap the oligomeric states of Ref, and the P1 WT Ref was again the only Ref that exhibited significant dimer formation (FIG. 7). Surprisingly, the φW39 WT Ref did not form a dimer even though it is indistinguishable from P1 WT Ref in DNA binding and other Ref nuclease assays. Upon amino acid sequence analysis of P1 WT and φW39 WT, we noticed that P1 Ref contains Cys11 while φW39 Ref contains Arg11.

Figure 8:
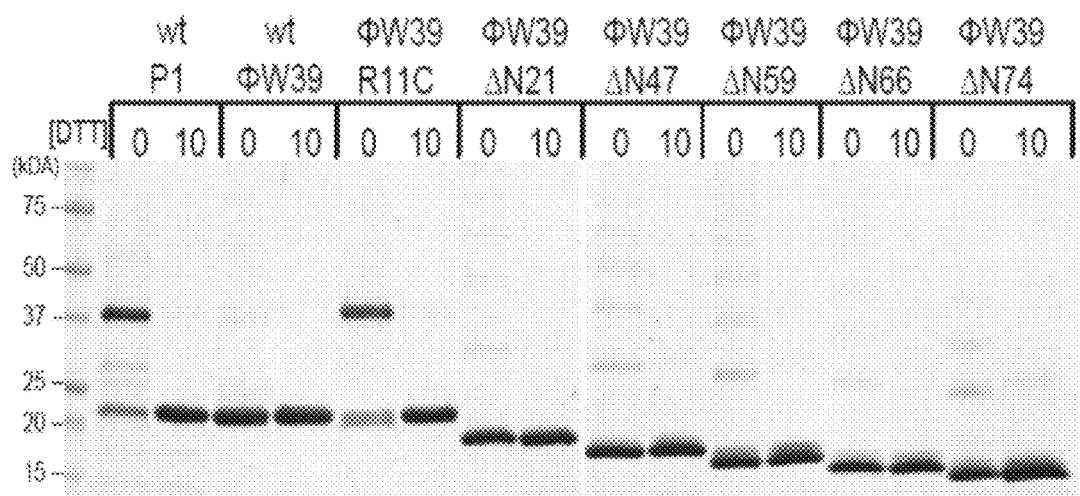
FIG. 8 shows P1 Ref Cys11 is necessary for disulfide formation and dimerization of Ref. SDSPAGE of dimerization assay in absence or presence of 10 mM DTT. WT P1 Ref and φW39 R11C Ref form stable dimers in non-reducing conditions, which are reduced in the presence of 10 mM DTT. WT φW39 Ref, φW39ΔN21 Ref, φW39ΔN47, φW39ΔN59, φW39ΔN66, φW39ΔN74 exhibit minimal formation of dimers and higher oligomeric complexes, and all are absent in the presence of 10 mM DTT.
Figure 9:
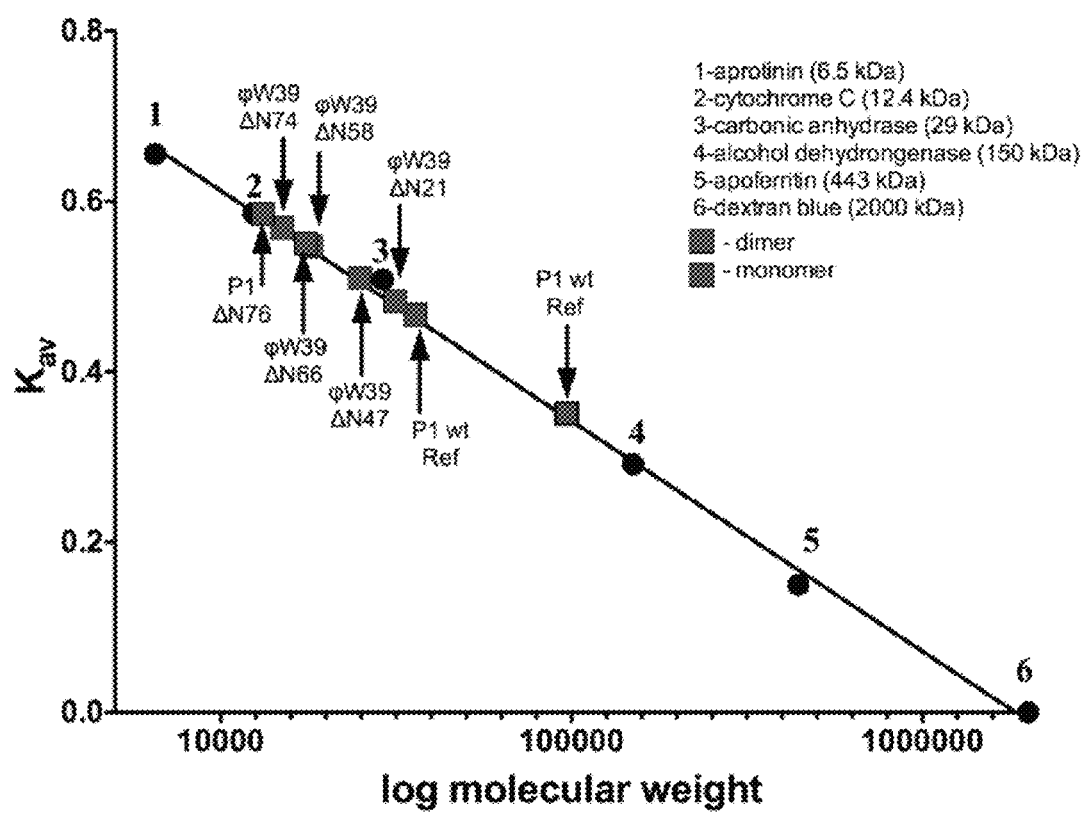
FIG. 9 shows only P1 WT Ref forms a dimer in solution. Graph of gel filtration elution profile of Ref truncation variants. Standards used to generate the elution volume standard curve are shown. An isocratic elution of Ref proteins was performed in 20 mM Tris-HCl, pH 7.5, 0.1 mM EDTA, 10% glycerol, and 200 mM KCl.

In order to determine the role of Cys11, a φW39 R11C variant was constructed and purified. In the DSG crosslinking experiment, the φW39 R11C dimerized at levels comparable to WT P1 Ref (FIG. 7). This result suggested that a disulfide bond was responsible for oligomerization of Ref. The P1 WT Ref, φW39 WT Ref, and all truncation variants were incubated in the absence or presence of 10 mM DTT and then run under non-reducing conditions on a SDS-PAGE. As shown in FIG. 8, the P1 WT Ref and φW39 R11C exhibited a dimer under non-reducing conditions, while the φW39 WT Ref and truncation variants exhibited negligible amounts of oligomerization. DTT substantially reduced the dimerization of P1 WT Ref and φW39 R11C. The truncation variants' monomeric state was verified by analytical size exclusion (FIG. 9). Although we previously hypothesized that the entire N-terminal domain was responsible for dimerization, these data provide evidence that Cys11 is the essential residue for dimerization of P1 Ref.

Figure 10:
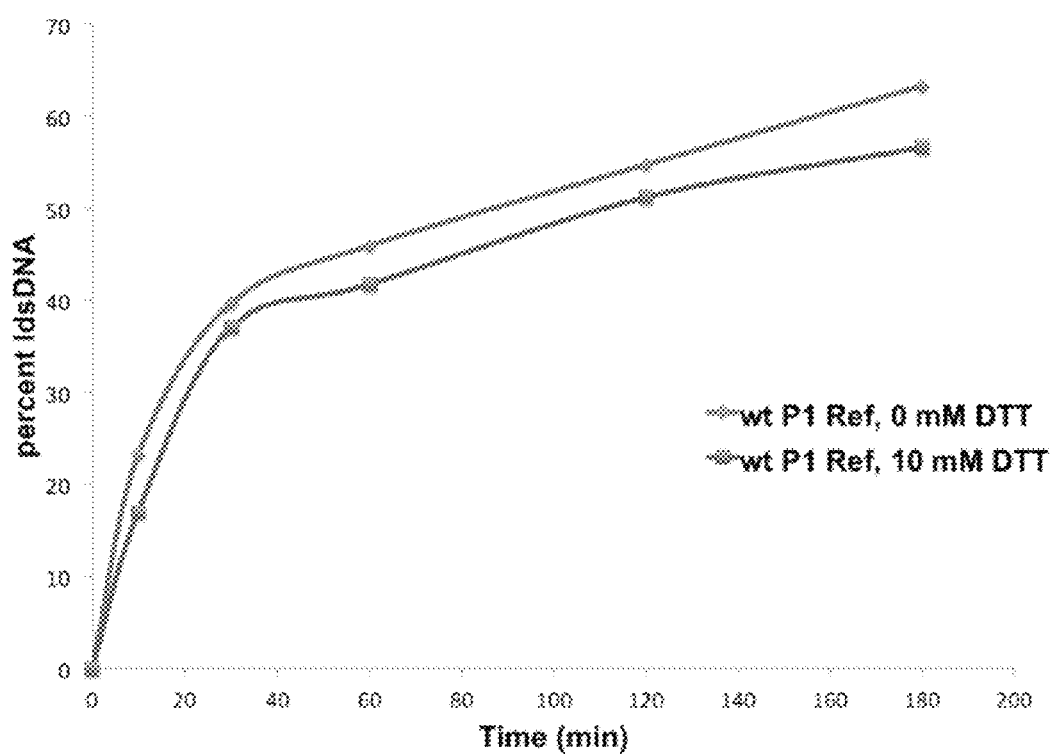
FIG. 10 is a graphical representation of ldsDNA formation over time from the nuclease site-specific targeting assay. Reactions were carried out as described in SI materials and methods, except 10 mM DTT was added immediately before Ref addition. P1 WT Ref was not affected by the inclusion of 10 mM DTT, indicating the Ref protein is functional as a monomer.

A recent model of Ref nuclease cleavage hypothesized that Ref acts as a dimer due to the preliminary ultracentrifugation data from P1 WT Ref. We now conclude that the active form of Ref is monomeric. The targeted nuclease activity of P1 WT Ref and φW39 R11C Ref was not affected by the inclusion of 10 mM DTT (FIG. 10). Since the P1 WT Ref and φW39 WT Ref have similar kinetics and the presence of DTT has no effect, it is likely that Ref is active as a monomer.

The N-Terminus of Ref is Necessary for ssDNA Nuclease Activity.

P1 Ref is a RecA dependent-nuclease on ssDNA (7). In the presence of M13mp18 cssDNA, RecA protein, ATP, and $Mg^{2+}$ there is extensive degradation of the DNA within twenty minutes (FIG. 11A). To test whether the truncations had any effect on nuclease activity, this assay was carried out using all truncation variants at the same concentration (24 nM). In the presence of RecA or Ref only there is no degradation of the cssDNA. After twenty minutes, the P1 WT, φW39 WT, φW39 ΔN21, and φW39 ΔN47 Ref all produced similar amounts of degradation in the presence of RecA (FIG. 11B). However, there was a clear decrease in nuclease activity as the truncations progressed to φW39 ΔN59, φW39 ΔN66, and φW39 ΔN74 Ref (FIG. 11B). The decrease in activity exhibited a gradient that is consistent with the removal of the putative charge motifs. When concentrations of φW39 ΔN59, φW39 ΔN66, φW39 ΔN74 Ref were increased ten-fold, levels of degradation similar to those produced by WT Ref were observed (FIG. 11B). The dramatic deficiency in the activity of φW39 ΔN66 and φW39 ΔN74 Ref coincides well with the deficiency in DNA binding.

Partial N-Terminal Ref Truncation Enhances Targeted Double-Strand Cleavage.

Figure 12:
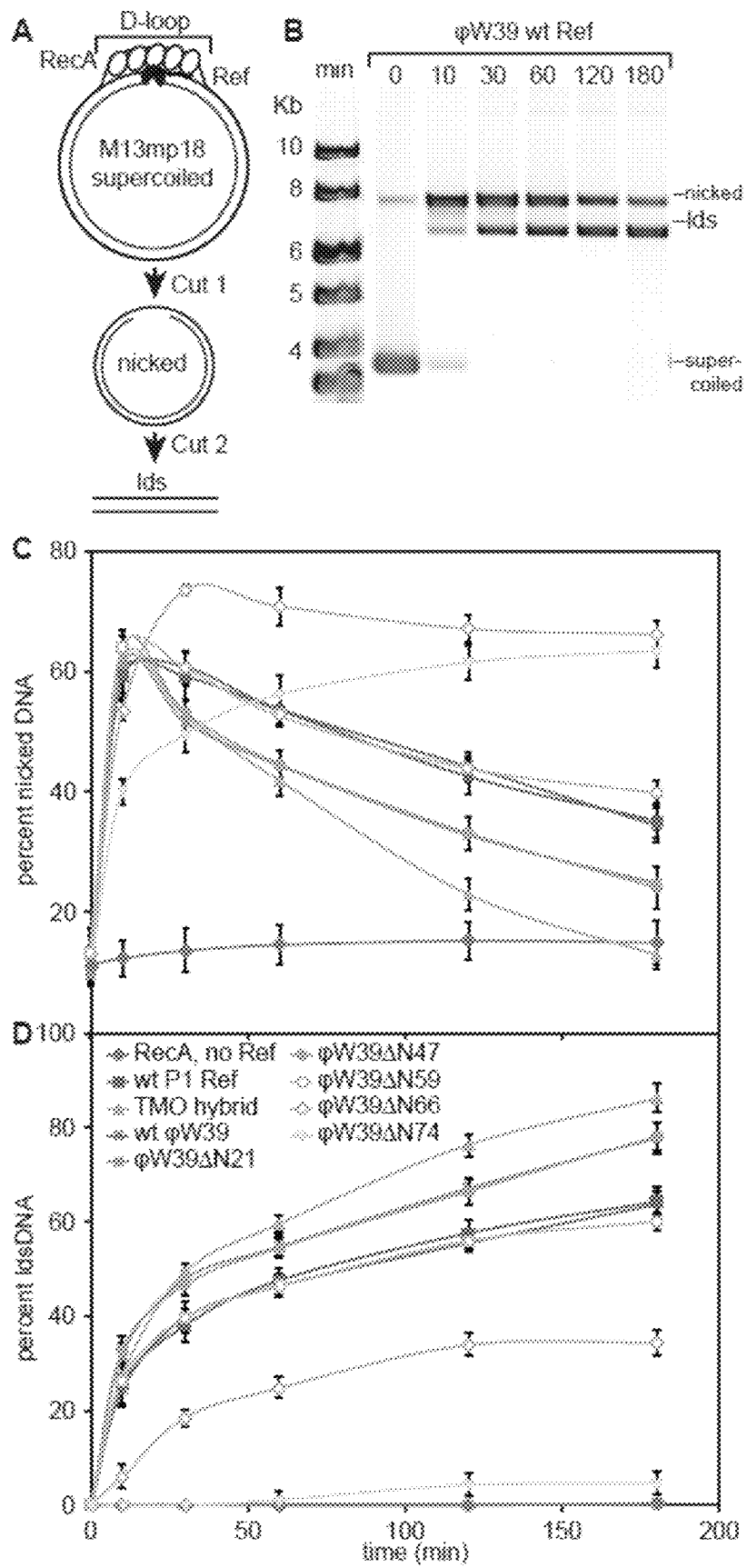
FIG. 12 shows that TMO hybrid Ref, φW39 ΔN21 Ref, and φW39 ΔN47 Ref show increased efficiency in creating targeted double strand breaks. (A) Reaction schematic of nuclease site-specific targeting assay. (B) Agarose gel representing time points from the targeted nuclease assay with φW39 WT Ref. Supercoiled DNA is the starting material (bottom band), which is converted first to nicked DNA (top band) and subsequently to linear DNA (middle band). Reactions were carried out as described in Methods. (C) Graphical representation of nicked product formation over time, averaged over at least three independent experiments. At 10 minutes all Ref proteins exhibit similar amounts of nicking. At 30 minutes the TMO hybrid Ref, φW39 ΔN21 Ref, and φW39 ΔN47 Ref show a greater decrease in nicked product, which corresponds to an increase in ldsDNA formation due to the second cut on the displaced strand. (D) Graphical representation of ldsDNA product formation over time, averaged over at least three independent experiments. Throughout the time course TMO hybrid Ref, φW39 ΔN21 Ref, and φW39 ΔN47 Ref all exhibit enhanced production of ldsDNA in comparison to WT Refs.
Figure 13:
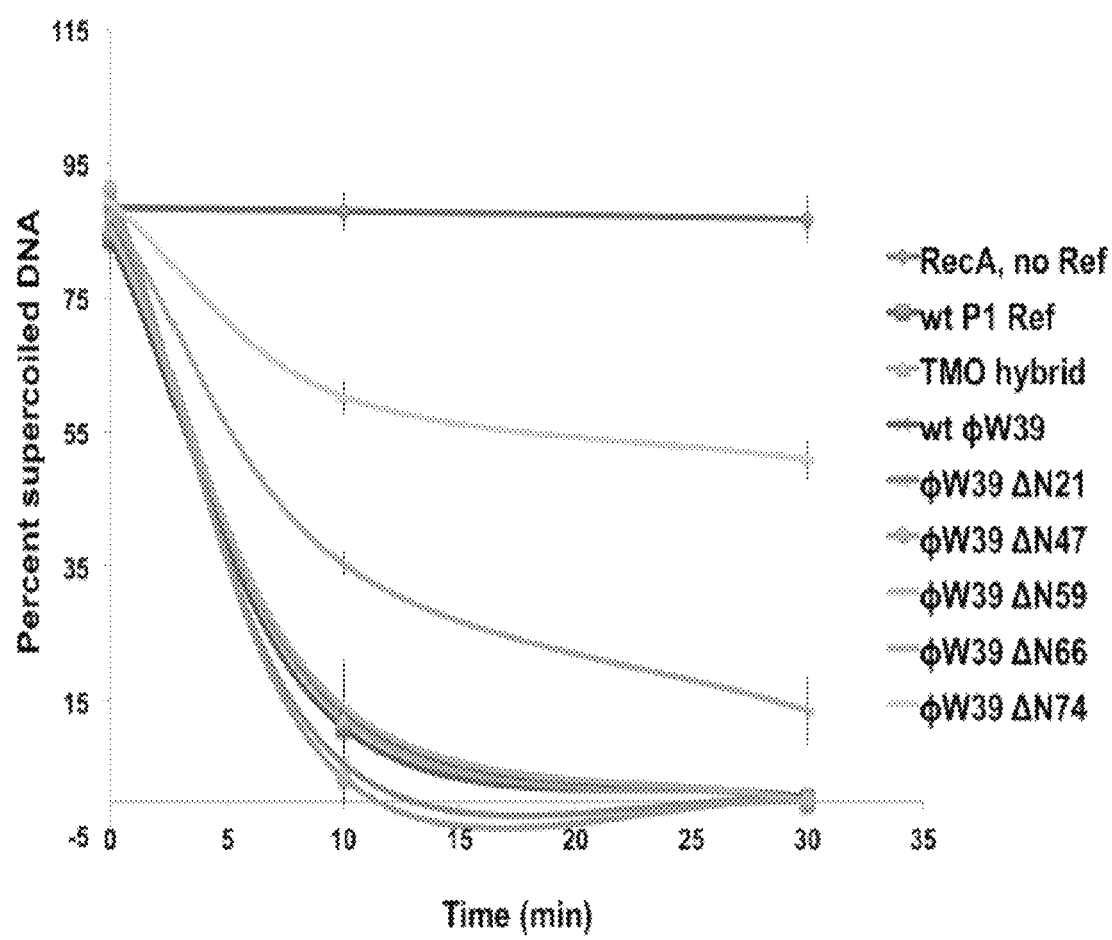
FIG. 13 is a graphical representation of supercoiled DNA disappearance over time from the nuclease site-specific targeting assay. Reactions were carried out as described in the materials and methods. P1 WT Ref, WT φW39 Ref, TMO hybrid, φW39 ΔN21, φW39 ΔN47, and φW39 ΔN59 show similar kinetics in the first 30 minutes. The φW39 ΔN66 and φW39 ΔN74 are much slower in comparison. Overall this suggests the first cut to produce nicked DNA, is not different between the Ref proteins tested.

Using an assay established previously (see Ronayne E A & Cox M M (2014), RecA-dependent programmable endonuclease Ref cleaves DNA in two distinct steps. *Nucleic Acids Res* 42: 3871-3883), we examined the efficiency of targeted dsDNA cleavage. In the reaction, supercoiled M13mp18 cdsDNA is incubated with a complementary 150-mer oligonucleotide and the RecA protein, which pairs the complementary oligonucleotide and duplex DNA (FIG. 12A). Within a RecA-created D-loop, Ref nicks the strand paired to the oligonucleotide rapidly, followed by a slower cleavage in the displaced strand to create a 7.25-kb (ldsDNA) (FIG. 12A). A representative agarose gel of the products formed in the presence of φW39 WT Ref is displayed in FIG. 12B. The supercoiled cdsDNA (FIG. 13), nicked cdsDNA (FIG. 12C) and ldsDNA (FIG. 12D) were measured as a percentage of the total DNA in each lane and followed over time.

The P1 WT, φW39 WT, and φW39 ΔN59 proteins exhibited identical reaction kinetics with about 63% of supercoiled DNA being linearized (FIG. 12D). Strikingly and reproducibly, the φW39 ΔN21, φW39 ΔN47, and TMO hybrid Ref increase ldsDNA product formation by 15-20% (FIG. 12D). At 30 minutes the φW39 ΔN21, φW39 ΔN47, and TMO hybrid Ref differed in kinetics compared to WT Refs by exhibiting a greater decrease in nicked DNA at the 30 minute timepoint (FIG. 12C). This decrease in nicked DNA corresponded to the second cleavage event, producing ldsDNA. The ldsDNA time course corroborated this. At 30 minutes we observed that the φW39 ΔN21, φW39 ΔN47, and TMO hybrid Ref produced about 10% more ldsDNA than the WT Refs. This enhanced ldsDNA product formation over wild type proteins may be the result of a faster second cleavage event on the displaced strand.

Figure 11:
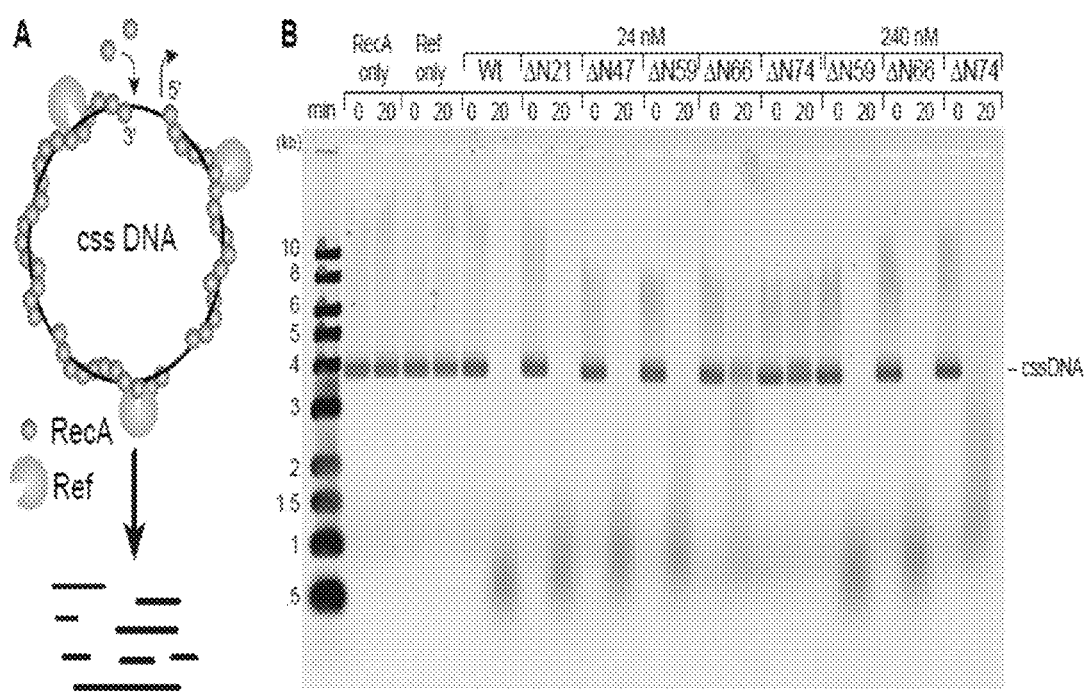
FIG. 11 shows the amino acids between position 47 and 74 are important for Ref nuclease activity on cssDNA. (A) Schematic of Ref cssDNA nuclease assay, as described in Methods. (B) Agarose gel of reactions after 20-minute incubation of cssDNA with all Ref variants. All cssDNA is degraded within 20 minutes with full-length WT φW39, φW39 ΔN21, φW39 ΔN47, and φW39 ΔN59 Ref. The φW39 ΔN66 and φW39 ΔN74 showed reduced activity at similar concentrations, but regained WT activity level with a 10-fold increase in protein concentration.

In contrast, the φW39 ΔN66 and φW39 ΔN74 exhibited decreased targeted assay efficiency. This corresponded with a deficiency in DNA binding (FIG. 6) and nuclease activity on cssDNA (FIG. 11). The φW39 ΔN66 Ref had a two-fold reduction in targeted nuclease activity, indicating that the removal of the 7 amino acids following the second charge motif is detrimental to the Ref activity. Upon removal of the remaining third putative charge motif, the φW39 ΔN74 Ref only generated 4% ldsDNA product in 3 hours. Both the φW39 ΔN66 and φW39 ΔN74 are capable of producing reduced but significant levels of nicked DNA, suggesting that the second cut needed to produce ldsDNA is especially compromised.

Discussion.

The present study elucidates the function of the intrinsically disordered N-terminal region of the Ref protein with two significant conclusions. First, the N-terminal region (a) is required for Ref binding to DNA, (b) contains a Cys necessary for the observed dimerization unique to the P1 WT Ref, and (c) is necessary for efficient Ref-mediated DNA cleavage. Second, removal of part, but not all of the N-terminus increases the efficiency of targeted Ref cleavage at D-loops. The most efficient Ref variants examined in this study lacked either 21 or 47 N-terminal amino acid residues. In contrast, removal of additional amino acid residues first reduced reaction efficiency to wild type levels (φW39 ΔN59) and ultimately a dramatic decrease in Ref function (φW39 ΔN66 and φW39 ΔN74) as a targeting endonuclease.

Via its action at RecA-created D-loops, Ref cleavage is programmable and can be targeted to any DNA sequence. Exploiting this technology for genome editing and other potential biotechnology applications requires a detailed understanding of Ref's mechanism of action and structure-function relationships. Removal of between 21 and 47 amino acid residues from the N-terminus is a first optimization strategy for creating targeted DSBs in vitro with Ref. In the N-terminus, we have identified a possible motif consisting of a ++ + +-+ charge distribution pattern. This putative motif is found three times in the N-terminal region of Ref (FIG. 1A). The results indicate that removal of one repeat improves Ref function in the targeted cleavage assay, while removal of multiple motifs results in notable deficiency in function. Amino acid sequence analysis of the N-terminus did not reveal any known DNA binding domains such as helix-turn-helix, helix-hairpin-helix, or NUMODs.

Figure 14:
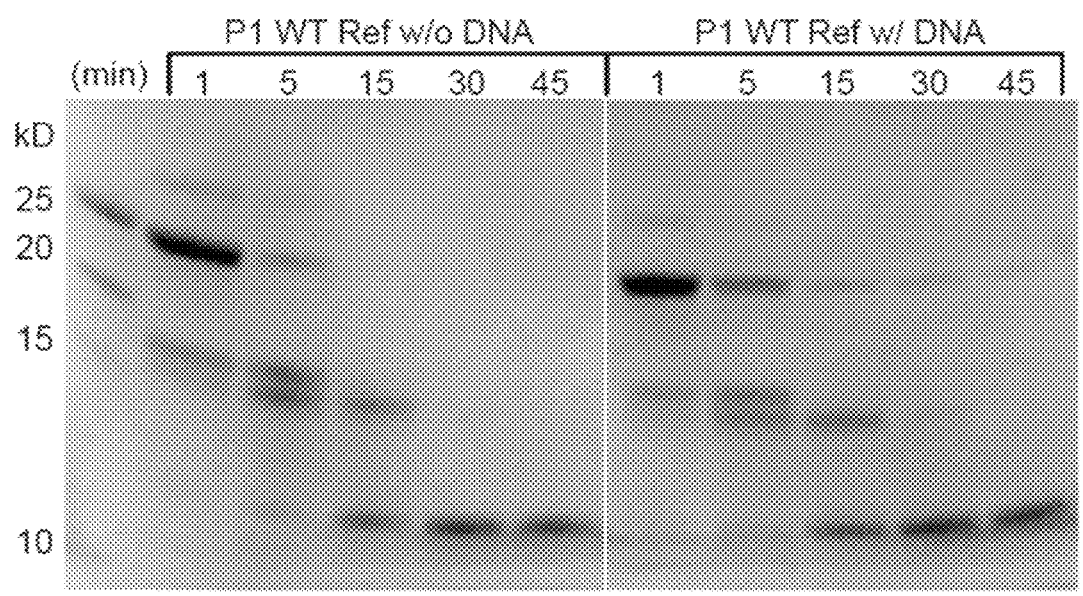
FIG. 14 shows limited proteolysis of P1 WT Ref. Images of Coomassie-stained SDS-gels of trypsin-limited proteolysis time-course experiments performed on P1 WT Ref in the absence or presence of a poly dT100 oligonucleotide. Reactions were carried out in Buffer A and aliquots were removed at the indicated time points. In the presence and absence of DNA, there was no difference in protease sensitivity.

Based on preliminary ultracentrifugation data on the P1 WT Ref (dimer-active) and P1ΔN76 (monomer-limited activity), we previously proposed that Ref functioned as a dimer. Although we now postulate that Ref is functionally monomeric, we cannot exclude the possibility that dimer formation occurs upon association with RecA or DNA. However, limited proteolysis in the absence or presence of DNA (FIG. 14) did not reveal a change in the protease sensitivity pattern. This suggests that Ref conformation and surface accessibility does not change in the presence of DNA in a manner that can be detected by this method.

Figure 15:
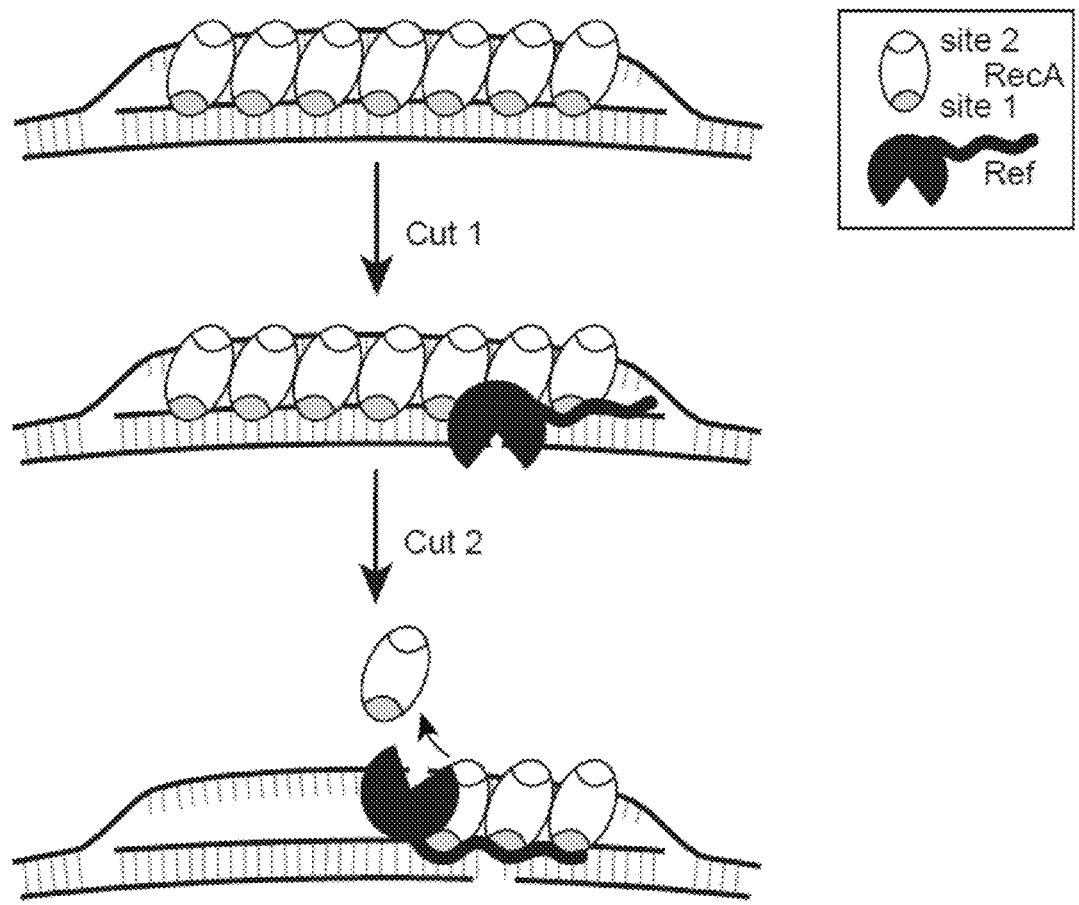
FIG. 15 shows a revised model for the creation of targeted DSBs by Ref. RecA creates a D-loop by binding the targeting oligonucleotide in the primary binding site (gray), and after finding homology, binds the displaced strand in the secondary site (white). The N-terminal domain of Ref binds the paired strand or DNA within the RecA filament groove, positioning the Ref for the first cut. ATP hydrolysis-dependent disassembly of the RecA filament occurs in the 5' to 3' direction. Upon RecA disassembly, Ref can access the displaced strand and create cut 2. The N-terminal domain anchors the Ref protein and a rearrangement occurs to allow the C-terminal nuclease domain access to the displaced strand.

Combining the present results with previous work, we present an updated model for the production of targeted DSBs by Ref (FIG. 15). The Ref protein cleaves the paired strand to create cut one, and subsequently cleaves the displaced strand to produce a targeted DSB. The properties of the first cleavage step suggest that it occurs within the RecA filament groove. The slower, second cleavage event has unique requirements that suggest it may occur only during or after RecA filament disassembly. Once RecA filament disassembly occurs in proximity to the Ref protein, we hypothesize that the Ref monomer rearranges to cut the displaced strand (FIG. 15).

In our new model, we propose that the N-terminal DNA binding domain of Ref acts as a tether to the DNA and/or RecA filament (FIG. 15). We hypothesize that the region of Ser66 and Ala82 may serve as a flexible linker, allowing the HNH nuclease domain to rearrange for a sequential nicking mechanism. Since the φW39 ΔN59 Ref retains similar nuclease levels to φW39 WT Ref, but the φW39 ΔN66 Ref activity is substantially reduced, the region between Pro59 and Ser66 constitutes the minimal N-terminal portion necessary for DNA binding without loss of nuclease efficiency.

There have been significant advances in genome editing, but there is room for expansion of this toolbox. The CRISPR/Cas 9 genome editing system has found abundant application in human cell lines, mice, zebrafish embryos, Drosophilia, yeast and other model organisms. The genomic sequence of interest is targeted with a chimeric guide RNA (gRNA) that directs genomic DNA cleavage by the endonuclease, Cas9. The gRNA complementary sequence in the genome needs to be preceded by a NGG sequence, termed a protospacer adjacent motif (PAM). This modestly restricts sequences that can be targeted for editing. In addition, significant off-target cleavage has been observed in human cells, limiting some therapeutic and research applications.

At present, the Ref system is limited by the need to introduce three components for cleavage (RecA, Ref, and a targeting oligonucleotide). However, the Ref system has no target DNA sequence constraints. Due to the length of the oligonucleotide employed, nonspecific cleavage of off-target sites can in principle be controlled.

Materials and Methods.

DNA Substrates.

The M13mp18 circular ssDNA (7249 nucleotides) was prepared as described previously (See Messing J (1983), New M13 vectors for cloning. *Methods Enzymol.* 101:20-78; Neuendorf S K & Cox M M (1986), Exchange of RecA protein between adjacent RecA protein single-stranded DNA complexes. *J. Biol. Chem.* 261:8276-8282). The M13mp18 circular dsDNA was prepared as described previously (See Messing J (1983), New M13 vectors for cloning. *Methods Enzymol.* 101:20-78; Neuendorf S K & Cox M M (1986), Exchange of RecA protein between adjacent RecA protein single-stranded DNA complexes. *J. Biol. Chem.* 261:8276-8282; Haruta N, Yu X N, Yang S X, Egelman E H, & Cox M M (2003), A DNA pairing-enhanced conformation of bacterial RecA proteins. *J Biol Chem* 278: 52710-52723). All DNA concentrations are given in µM nucleotides (µM nt). Oligonucleotides were purchased from Integrated DNA technologies.

Cloning Ref and Ref Variants.

The WT ref gene from bacteriophage φW39 was not available, as stocks of this phage no longer exist. The φW39 ref gene was reconstructed to match the reported sequence by mutagenesis of the P1 ref gene in pEAW584 (WT P1 ref in protein expression vector pET21A (Novagen)). Detailed cloning procedures for all Ref variants can be found below.

Proteins.

The *E. coli* RecA E38K protein was purified as described previously (See Ronayne 2014, supra). The P1 WT Ref and P1 ΔN76 proteins were purified as described previously (see Gruenig M C, et al. (2011), Creating Directed Double-strand Breaks with the Ref Protein A novel RecA-dependent nuclease from bacteriophage P1. *J Biol Chem* 286:8240-8251). All Ref variants were purified in their native form using standard chromatography procedures, and quantified, as described further below. The mass of all variants was confirmed by mass spectrometry. All proteins were stringently tested for exonuclease and endonuclease contamination and all were free from detectable nuclease activity in the absence of RecA protein.

Fluorescence Polarization DNA Binding Assay.

Ref proteins at 0.5-10,000 nM were incubated with 2 nM AJM25 71mer ssDNA or AJM25 annealed with AJG52 71mer to make a linear 71 bp dsDNA substrate in 25 mM Tris-acetate (pH 8.5), 3 mM potassium glutamate, 15 mM magnesium acetate, and 5% w/v glycerol at room temperature for 15 minutes. Fluorescence anisotropy (FA) was measured at 25° C., using a Tecan Infinite M1000 instrument with 470-nm excitation and 535-nm emission wavelengths for at least three replicates. The average FA values were plotted with one standard deviation of the mean shown as error. Prism software was used to convert FA values to the percent of DNA bound and apparent dissociation constants were determined using one-site, specific binding with Hill coefficient.

Circular ssDNA Nuclease Assay.

Ref proteins were tested for nuclease activity as previously described (see Gruenig 2011, Supra). See further details below.

Nuclease Site-Specific Targeting Assay.

Ref proteins were tested for targeted nuclease activity in assays as previously described (See Ronayne 2014, supra). See details below.

Non-Reducing SDS-PAGE.

All Ref proteins were dialyzed into 20 mM sodium phosphate (pH 7.5), 200 mM sodium choloride, and 10% glycerol to remove DTT present from purification. Each reaction contained 6.5 µg Ref protein, 50 mM sodium phosphate (pH 7.5), 75 mM sodium chloride, and in indicated reactions 10 mM dithio (DTT). Non-reducing cracking buffer (80 mM Tris-HCl pH 6.8, 2% SDS, 10% glycerol, 0.2% bromophenol blue) was added to each sample and then run on a 4-15% gradient SDS-PAGE.

DNA Substrates.

Sequences of oligonucleotides used in this study are as follows:

```
rlb1 150 mer (SEQ ID NO: 17):
TTTTGGTTTTTATCGTCGTCTGGTAAACGAGGGTTATGATAGTGTTGC

TCTTACTATGCCTCGTAATTCCTTTTGGCGTTATGTATCTGCATTAGT
```

```
-continued
TGAATGTGGTATTCCTAAATCTCAACTGATGAATCTTTCTACCTGTAA

TAATGT

AJM25 71 mer (SEQ ID NO: 18):
56FAM/CAGAAGTAAGTTGGCCGCAGTGTTATCACTCATGGTTATGGC

AGCACTGCATAATTCTCTTACTGTCATGC

AJG52 71 mer (SEQ ID NO: 19):
GCATGACAGTAAGAGAATTATGCAGTGCTGCCATAACCATGAGTGATA

ACACTGCGGCCAACTTACTTCTG
```

Cloning Ref and Ref Variants.

The WT ref gene from bacteriophage φW39 was not available, as stocks of this phage no longer exist. The gene was reconstructed to match the published sequence by mutagenesis of the P1 ref gene in pEAW584 (WT P1 ref in protein expression vector pET21A (Novagen)). The mutations were I8L, C11R, K13E, V34A, T46S, L47I, R86T, A93T, N107E, and A115S. Silent mutations to improve codon usage were also made and the resulting plasmid is pTMO9.

The φW39ΔN59 Ref.

Plasmid pTMO9 was used as a PCR template with an upstream primer consisting of a NdeI site followed by bases 178-202 of φW39 ref with a G to T change at base 192, and a T to C change at base 198 to make silent mutations for better codon use at codons 64 and 66. The ATG bases included in the NdeI site encode the first Met codon of the gene. The downstream primer consists of a BamHI site followed by bases 544-561 of the φW39 ref gene in 5" to 3" orientation. The PCR product was digested with NdeI and BamHI and inserted into pET21A digested with the same enzymes. The resulting plasmid, pEAW920 was directly sequenced to confirm the presence of φW39 ΔN59 Ref.

The φW394N21, ΔN47, ΔN66, and ΔN74 Refs.

Each plasmid was constructed in the same manner as pEAW920 except the upstream primers consisted of bases 64-101, 142-154, 199-222, 223-248, respectively of φW39 Ref, with several changes for improved codon usage at codons 49, 70, 75, 77, and 78 in one or more constructs. This generated plasmids pEAW886, pEAW865, pEAW919, and pEAW971, respectively.

The φW39 R11C Ref.

Plasmid pTMO9 was used as the PCR template with an upstream primer consisting of a NdeI site followed by bases 4-45 of φW39 Ref, with the CGC coding for Arg at amino acid 11 changed to GCT to make a Cys substitution. The downstream primer consists of a BamHI site followed by bases 544-561 of the φW39 Ref gene in 5' to 3' orientation. The PCR product was digested with NdeI and BamHI and inserted into pET21A digested with the same enzymes. The resulting plasmid, pEAW933, was directly sequenced to confirm the presence of φW39 R11C.

TMO hybrid Ref vector is PTMO8, which encodes the P1 Ref protein in pET21A, with mutations at I8L, C11R, K13E, V34A, T46S, L47I, N107E, and A115S. It lacks the R86T and A93T mutations found in φW39 WT Ref.

Overexpression and Purification of Ref and Ref Variants.

The φW39 WT Ref and φW39 ΔN59 Ref were purified with procedures using similar growth, induction, cell harvesting, and early fractionation steps as P1 WT Ref. Both of these over-expression vectors were transformed into BL21 (DE3) cells. Purification entailed polyethyleneimine precipitation, precipitation with (NH4)2SO4, and chromatography successively using butyl-Sepharose (120 mL CV), Source Q, Source 15S, and Sephacryl S-100 gel filtration columns. This was followed by another butyl-Sepharose (20 mL CV) chromatography step. Before cell lysis, the protease inhibitor Pefabloc SC (Sigma) was added to 0.1 mg/ml final concentration. Concentrations were determined using ProteinCalculator v3.4 calculated extinction coefficients of $2.788\times10^4 M^{-1} cm^{-1}$ for φW39 WT Ref and $1.5220\times10^4 M^{-1} cm^{-1}$ for φW39 ΔN59.

The φW39 ΔN21 Ref, φW39 ΔN47 Ref, φW39 ΔN66 Ref, φW39 ΔN74 Ref, and φW39 R11C Ref were purified similarly to the above proteins with one major modification: the overexpression vectors were transformed into BLR (DE3) cells. This prevents RecA contamination during the purification. Concentrations were determined using ProteinCalculator v3.4 calculated extinction coefficients of $2.219\times10^4 M^{-1} cm^{-1}$ for φW39 ΔN21, $1.5220\times10^4 M^{-1} cm^{-1}$ for φW39 ΔN47, φW39 ΔN66, φW39 ΔN74, and $2.788\times10^4 M^{-1} cm^{-1}$ for φW39 R11C. All proteins were stringently tested for exonuclease and endonuclease contamination and all were free from detectable nuclease activity in the absence of RecA protein.

The TMO Hybrid Ref was purified with procedures using similar growth, induction, cell harvesting, and early fractionation steps as P1 WT Ref. Similarly, the over-expression vector was transformed into BL21(DE3) cells. Purification included polyethyleneimine precipitation, precipitation with (NH4)2SO4, and chromatography successively using butyl-Sepharose (120 mL CV), hydroxyapatite, Source 15Q, and SP Fast Flow (GE17-5157-01) columns. These steps were followed by another butyl-Sepharose (20 mL CV) chromatography step. Significant degradation of the protein occurred during the hydroxyapatite step and successive chromatography steps were performed to purify the specific-sized degradation product lacking 47 N-terminal amino acid residues. Electrospray ionization and tandem mass spectrometry were used verify the amino acid position of degradation. Concentration was determined using ProteinCalculator v3.4 calculated extinction coefficient of $1.6500\times10^4 M^{-1} cm^{-1}$.

Circular ssDNA Nuclease Assay.

Reactions are incubated with Buffer A (containing 25 mM Tris-acetate (pH 8.5), 3 mM potassium glutamate, 15 mM magnesium acetate, and 5% w/v glycerol), an ATP regeneration system (10 U/mL pyruvate kinase and 3.5 mM phosphoenolpyruvate), 4 µM nt M13mp18 cssDNA, and 2.4 µM RecA E38K at 37° C. for 10 min. Reactions are incubated an additional 15 min with 3 mM ATP to allow an active RecA nucleoprotein filament to form prior to the addition of Ref at 24 nM (or as indicated). After 20 min, 20 µL of the reaction mixture are added to 10 µL of stop solution (9% Ficoll, 0.25% bromphenol blue, 0.25% xylene cyanol, and 4% SDS) then incubated another 30 min at 37° C. Samples were analyzed by electrophoresis in 0.8% agarose with TAE buffer (40 mM Tris-Acetate, 1 mM EDTA), stained with SYBR gold, and visualized using the SYBR gold setting on a Typhoon FLA 9000 (GE Healthcare).

Nuclease Site-Specific Targeting Assay.

The reactions were carried out at 37° C. in buffer A, (containing 25 mM Tris-acetate (pH 8.5), 1 mM DTT, 3 mM potassium glutamate, 15 mM magnesium acetate, and 5% w/v glycerol) and an ATP regeneration system (10 U/mL pyruvate kinase and 3.5 mM phosphoenolpyruvate. The above components were incubated for 10 minutes with a targeting oligonucleotide (4 µM nt, rlb1 150mer) and RecA E38K (1.33 µM). ATP (3 mM) was added and incubated an additional 20 minutes, followed by M13mp18 circular dsDNA (8 µMnt) and another 20 minute incubation. Before adding Ref, a zero time point was taken, then Ref (100 nM) was added. The reactions were stopped at the noted time points by removing 20 µL from the reaction and adding it to 20 µL of stop solution (12 mM Tris acetate pH 7.5, 10.8% (w/v) Ficoll, 0.15% (w/v) each bromophenol blue and xylene cyanol, 8% SDS) and incubating at 37° C. an additional 30 minutes. Samples were analyzed by electrophoresis on a 0.8% agarose gel with TAE buffer, stained with SYBR Gold stain, and imaged using the SYBR gold settings on a Typhoon FLA 9000 (GE Healthcare). Gel image was analyzed using ImageQuant TL software (GE Healthcare). Lanes were normalized for loading conditions by reporting individual band intensity as a percentage of the total band intensity in that lane.

Example 7

Ref In-Vitro Targeting Assays: Optimizing Components and Concentrations

In this Example, we demonstrate how parameters and concentrations used in the disclosed methods can be optimized. Specifically, using the in-vitro nuclease assays described previously, we determined that the following components and parameters facilitate optimal Ref nuclease activity: 1.33 uM RecA; 3 mM ATP; pyruvate kinase (10 U/ml)—ATP regeneration system; phosphoenolpyruvate (3.5)—ATP regeneration system; 0.1 uM Ref; 8 uM n.t. dsDNA (1.1 nM molecules); 4 uM n.t. targeting oligo (4/3=1.3 uM RecA binding sites); 15 mM Mg2+; pH 8.5.

In this optimized assay, the RecA/Ref ratio=13.3 RecA's for 1 Ref. The RecA is equimolar with the targeting oligonucleotide. Preferably, RecA is equimolar or slight excess of targeting oligo for the most efficient reaction. If the RecA concentration is less than the available DNA binding sites, then RecA filaments do not form as well. If the oligo concentration is increased to 16 uM, linear DNA production is reduced, and if oligo concentration is decreases to 0.4 uM, there is also significant reductions in linear product.

Figure 16:
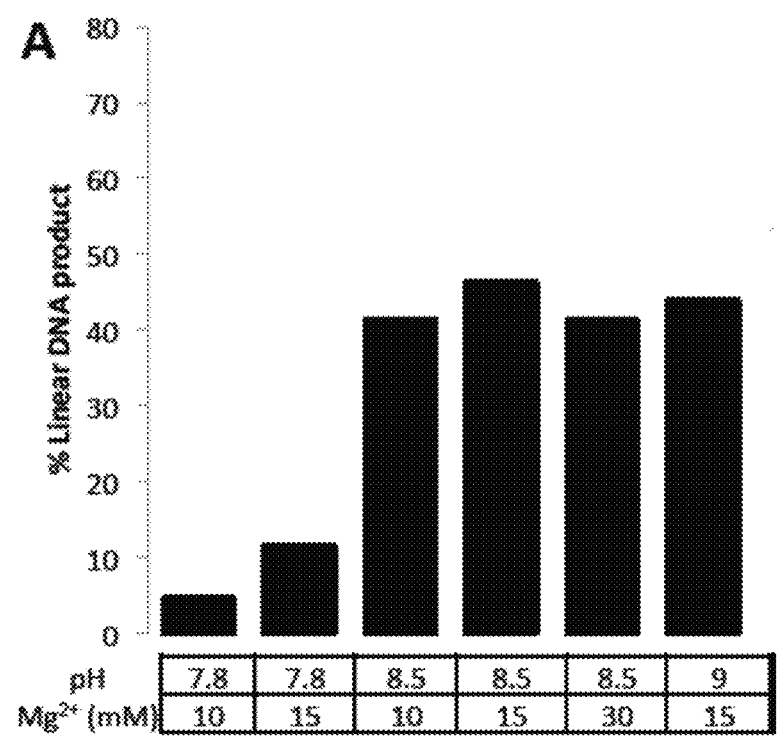
FIG. 16 is a graphical representation of optimized parameters for targeted nuclease assays. (A) Bar graph showing effects of varying pH and Mg2+ concentration. (B) Bar graph showing effects of varying Ref concentration. (C) Bar graph showing effects of varying RecA/Ref ratio.
Figure 16:
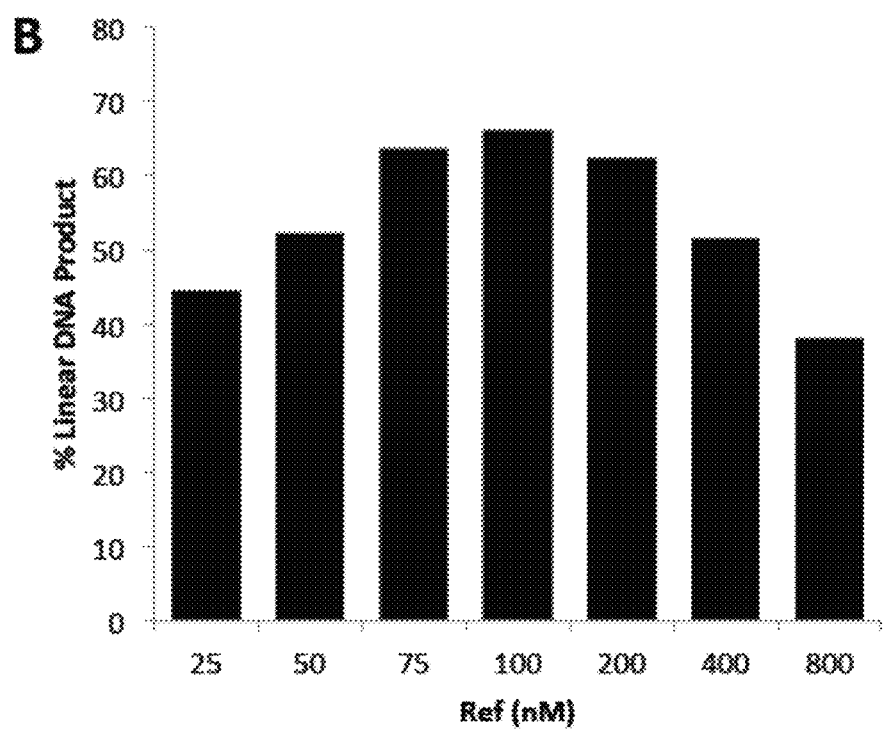
Figure 16:
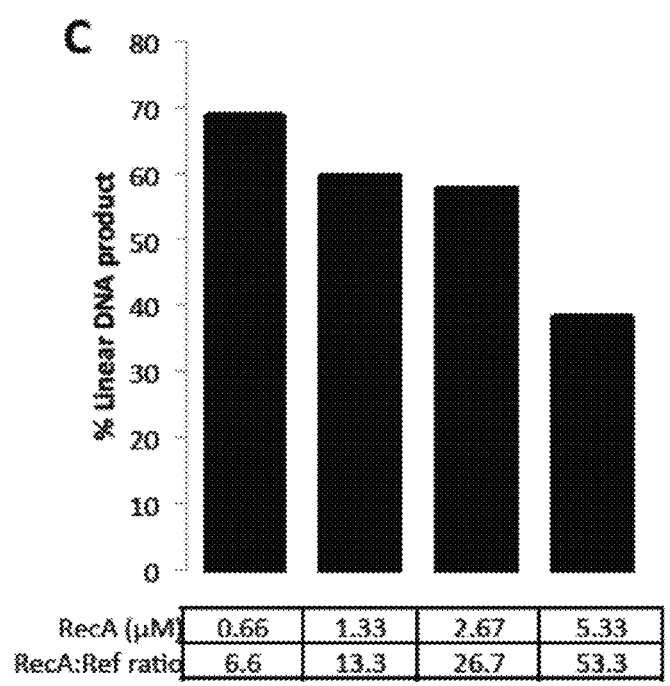

Reactions that contain 0.1-0.2 uM Ref, 1-4 uM n.t. oligo and 1.33 uM RecA all give similar amounts of linear product. If the Ref concentration is increased to 0.4 uM, product formation begins to decrease. If the RecA concentration is increased to 2.66 uM with 0.1-0.4 uM Ref and 1-8 uM n.t. oligo, this also results in decreased product formation, of about 10%. Further optimization data is shown in FIG. 16.

The Ref/RecA ratio is the component with the narrowest range for optimized efficiency. If greater than 400 nM of WT Ref is used, this drastically reduces efficiency. For the disclosed Ref truncation variants, this value may be quite different. Since the DNA binding is different for each variant, the optimal Ref concentration for each variant will also be different. Increasing concentration of Ref truncations (ΔN21-N47) up to 1 uM inhibits the nuclease activity, marking a upper level of optimized concentration.

Example 8

Ref In-Vivo Targeting Assays and Genomic Editing

A system using the disclosed truncated Ref polypeptides has potential for doing a multitude of genomic editing functions including gene deletions, insertions, and point mutations. In this Example, RecA/Ref in vivo targeting elucidates the breadth of the system.

Introduction.

Genome editing is currently done through generation of a double-strand break (DSB). The DSB is generated at a specific site within a gene and this is where many of the genome editing technologies function. Once a DSB is produced, it can be repaired through one of two DNA repair pathways: 1) Non-Homologous End Joining (NHEJ) DNA repair or 2) homologous recombinational DNA repair. The NHEJ repairs the DSB in an error-prone manner that typically produces insertions or deletions. This effectively will lead to frameshifts and premature stop codons, thus disrupting the gene product. In order for the cell to use homologous recombinational repair, a repair template DNA needs to be introduced into the cell. This exogenous piece of DNA containing the desired nucleotide change will be incorporated into the genome upon homologous recombinational repair. Therefore, the desired change is incorporated into a specific gene region.

Since the truncated Ref can be directed to cleave a specific DNA structure generated by RecA, the Ref/RecA system has potential to be used for in vivo genome editing. Strategies of genome editing often utilize double-strand breaks (DSBs) to direct repair and recombinase-mediated homologous recombination with a fragment of DNA containing a desired mutation. A similar technique, CRISPR/Cas9, has become a popular mode of in vivo genome editing in recent years. CRISPR/Cas9 uses an RNA guide rather than a DNA guide to direct induced incorporation of a desired mutation. The CRISPR/Cas9 system has some limitations including the requirement of a protospacer adjacent motif (PAM) that limits certain regions of the genome for editing. Off-target cleavage events have also proven to be problematic. The truncated Ref system is not limited by any target DNA sequence constraints. Due to the length of the oligonucleotide and RecA-catalyzed pairing, nonspecific cleavage of off-target sites may be minimized. It would retain some advantages of the Cas9 system in that the nuclease utilized is always the same. However, the guide would be DNA instead of RNA.

Experimental Procedures.

Nuclease Site-Specific Targeting Assay.

Wild type Ref proteins were tested for targeted nuclease activity in assays as previously described. The reactions were carried out at 37° C. in buffer A, (containing 25 mM Tris-acetate (pH 8.5), 1 mM DTT, 3 mM potassium glutamate, 15 mM magnesium acetate, and 5% w/v glycerol) and an ATP regeneration system (10 U/mL pyruvate kinase and 3.5 mM phosphoenolpyruvate. The above components were incubated for 10 minutes with a targeting oligonucleotide (sequences of targeting oligonucleotides are listed in Table 1 below) and RecA E38K (1.33 µM). ATP (3 mM) was added and incubated an additional 20 minutes, followed by M13mp18 circular dsDNA (8 µMnt) and another 20 minute incubation. Before adding Ref, a zero time point was taken, then Ref (100 nM) was added. The reactions were stopped at the noted time points by removing 20 µL from the reaction and adding it to 20 µL of stop solution (12 mM Tris acetate pH 7.5, 10.8% (w/v) Ficoll, 0.15% (w/v) each bromophenol blue and xylene cyanol, 8% SDS) and incubating at 37° C. an additional 30 minutes. Samples were analyzed by electrophoresis on a 0.8% agarose gel with TAE buffer, stained with SYBR Gold stain, and imaged using the SYBR gold settings on a Typhoon FLA 9000 (GE Healthcare). Gel image was analyzed using ImageQuant TL software (GE Healthcare). Lanes were normalized for loading conditions by reporting individual band intensity as a percentage of the total band intensity in that lane. The only modification was in targeting oligonucleotide utilized.

Electrocompetent Cells for In Vivo Targeting.

Plasmids containing the empty vector (pET21A), P1 Ref only (pEAW584), RecA only (pEAW260), and RecA and P1 Ref (pEAW692) were transformed into chemically competent MG1655 (DE3) ΔrecA (strain EAW20 (DE3)). Each of these cell types were made electrocompetent by growing up to an $OD_{600}$ of ~0.80 at 37° C. and stopping growth on ice for 15 minutes. Cells were pelleted between washing by centrifugation for 10 minutes at 6000 rpm; cells were washed three times with ice cold water. Final pellet was resuspended in 0.5 mL cold 10% glycerol, 40 µL aliquoted were made and cells were frozen in liquid $N_2$ before storing in a −80° C. freezer. When cells were needed, they were thawed on ice.

In Vivo Targeting with the RecA/Ref System.

Targeting of the rpsL gene was used to determine if RecA/Ref can be used to incorporate a desired mutation into the *E. coli* MG1655 genome. Electrocompetent cells with plasmids expressing Ref, RecA, or RecA/Ref were made as described above. A targeting/editing oligonucleotide was introduced by electroporation. Initial targeting experiments were done with AJG 53-140mer oligonucleotide. Experiments to determine optimal oligo length were also performed. Sequences of all oligos utilized are listed in Table 1 below. After electroporation, LB was immediately added and cells recovered overnight at 37° C. and were plated on LB or streptomycin plates. Colony forming units (cfu) were counted and the fraction of streptomycin resistance cells per total cfu was determined as efficiency. Normalized efficiency was calculated as efficiency of cell type expressing RecA/Ref divided by efficiency of the strain expressing only RecA.

Appropriate cell aliquots were thawed on ice and electroporated at 2.5 kV after adding 10 µL of appropriate oligonucleotide at 100 µM (all oligonucleotides were resuspended in water from lyophilized pellets). 1 mL of room temperature LB was added immediately to electroporation cuvette and cell-suspension was transferred to 4 mL room temperature LB and recovered with aeration overnight at 37° C. Dilutions of overnight were made and 100 µL of $10^{-6}$ cells were plated on LB, 1 mL of the overnight was plated on streptomycin (100 µg/mL) and grown overnight at 37° C. Colony forming units (cfu) were counted the next day. Error bars represented as standard deviation of 3 or more independent experiments.

Results.

The RecA/Ref System can be Used to Create Two DSBs Simultaneously In Vitro.

Figure 17:
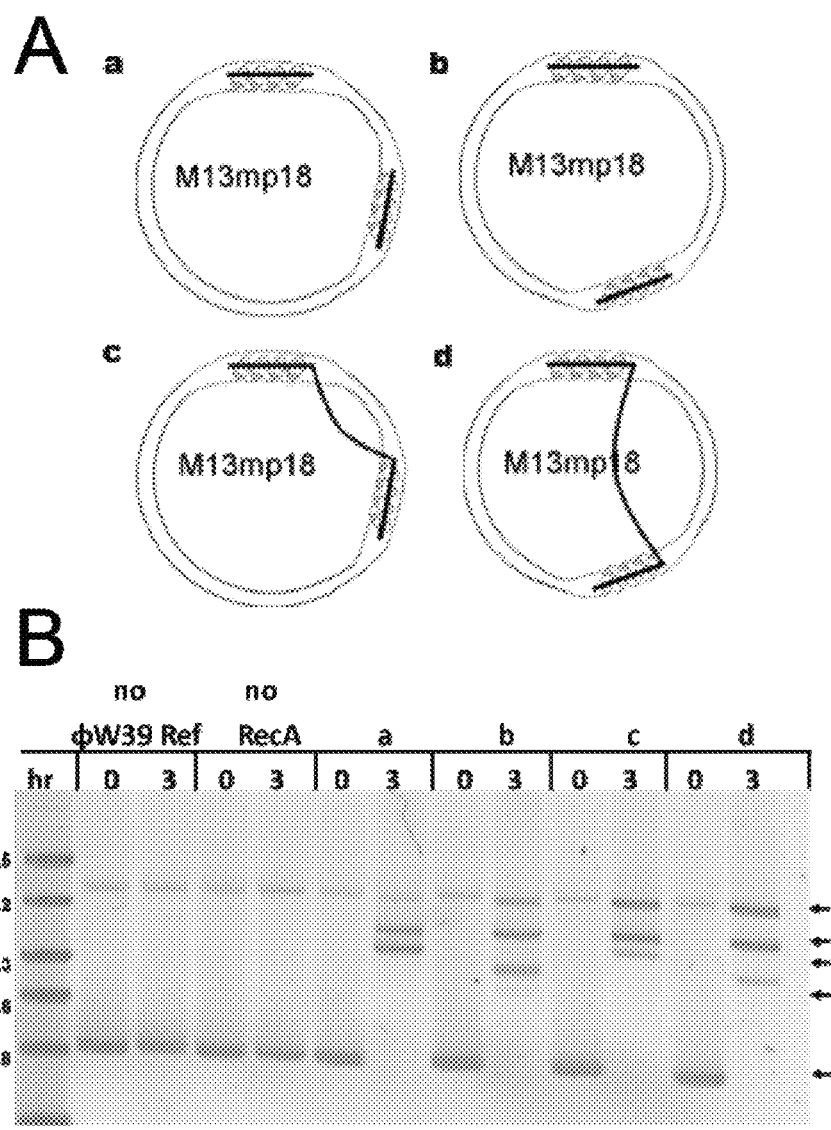
FIG. 17 shows that RecA/Ref system can create "deletions" in vitro by utilizing two separate D-loops. (A) Illustration of each reaction condition before addition of Ref. (a) represents two separate oligonucleotides 500 bases apart, (b) represents two oligonucleotides 1000 bases apart, (c) represents one oligonucleotide whose homologous regions are 500 bases apart connected by 12 nt linker, and (d) represents one oligonucleotide whose homologous regions are 1000 bases apart connected by 12 nt linker. (B) Representative agarose gel of targeted nuclease assay. Reactions a, b, c, and d corresponds with indicated setup in (A).

In the Examples above, we characterized several Ref truncation variants in vitro. In addition to investigating the efficiency of these variants to create targeted DSBs, we were interested in the capacity of the RecA/Ref system for genome editing, specifically gene deletions. A modification of the nuclease site-specific targeting assay was applied in order to demonstrate that more than a single targeted cut could be created in one reaction. Either two oligonucleotides were introduced whose complementary regions were 500 or 1000 bases apart, or one oligonucleotide was introduced whose complementary regions were 500 or 100 bases apart and were connected by an arbitrary 12 base linker (FIG. 17A). The representative gel shows reactions taken at 0 and 3 hours for a targeted nuclease assay performed in the presence of WT φW39 Ref with "no Ref" and "no RecA" controls (FIG. 17B). The initial conditions before addition of Ref are illustrated in FIG. 17A.

The success of reactions a and b (separate oligonucleotides), as well as b and d (linked oligonucleotides) for creating targeted DSBs are shown in FIG. 17B by the appearance of band sizes 6.75 and 6.25 kb at 3 hours. Band sizes 0.50 and 1 kb are not seen on the gel due to their small size. This demonstrates that Ref is capable of creating two separate DSBs in vitro with either two separate oligonucleotides or one linked oligonucleotides, although the reaction including the two separate oligonucleotides is slightly more efficient (quantification not shown).

The RecA/Ref System can be Used for In Vivo Genome Editing.

From our interest in comparing the RecA/Ref to the CRISPR/Cas9 system, the procedure used here was adapted from experiments utilizing CRISPR/Cas9 (see Jiang, W. Y., Bikard, D., Cox, D., Zhang, F., and Marraffini, L. A. (2013), RNA-guided editing of bacterial genomes using CRISPR-Cas systems. *Nature Biotechnology* 31, 233-239). Using this adapted method and an oligonucleotide that similarly confers streptomycin resistance to the cell if properly incorporated, it was possible to measure the efficiency of mutation based on the fraction of streptomycin resistant cells per total colony forming units (cfu).

Figure 18:
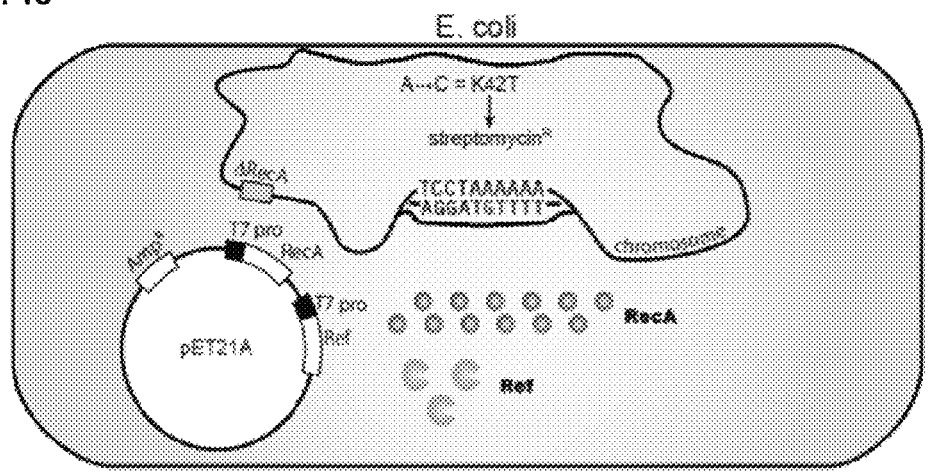
FIG. 18 shows use of the RecA/Ref system for genome editing in *E. coli*. (A) Schematic of RecA/Ref system designed for in vivo genome editing in *E. coli* MG1655. The Ref and RecA are expressed from pET21A and the editing/targeting oligonucleotide incorporates a single nucleotide change to make cells streptomycin resistant. The TCCTAAAAAA sequence shown is SEQ ID NO:29, and the AGGATGTTTT sequence shown is SEQ ID NO:30. (B) Preliminary data for in vivo targeting. Experimental design and details are described in "Experimental Procedures". When RecA and Ref are present, there is a 10-fold increase in streptomycin resistant cells (p value<0.05). This experiment was performed with a 140mer targeting oligonucleotide. (C) Normalized efficiency for varying lengths of targeting oligonucleotide. The 100mer and 140mer are most efficient for targeting. Normalized efficient is defined as the fraction of streptomycin resistant cells per total cfu for RecA/Ref cells divided by the same for RecA only cells.
Figure 18:
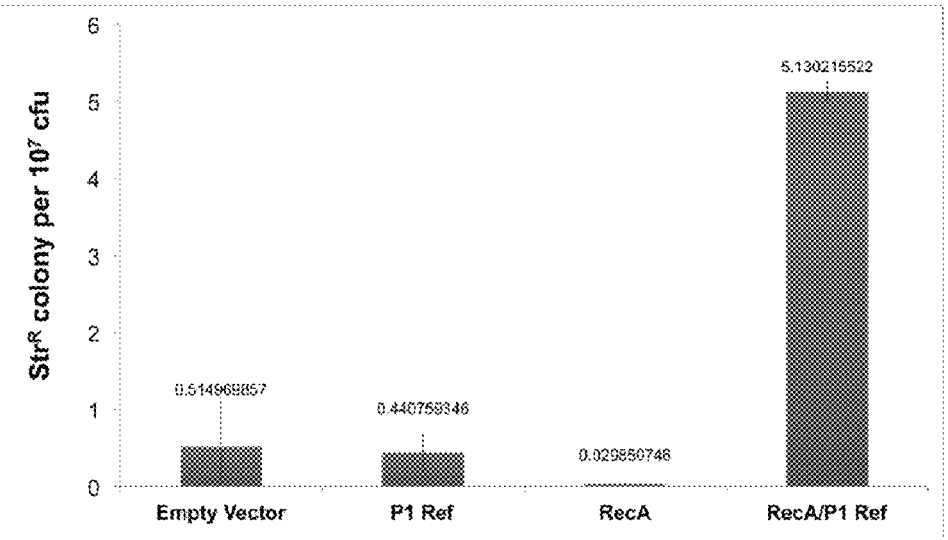
Figure 18:
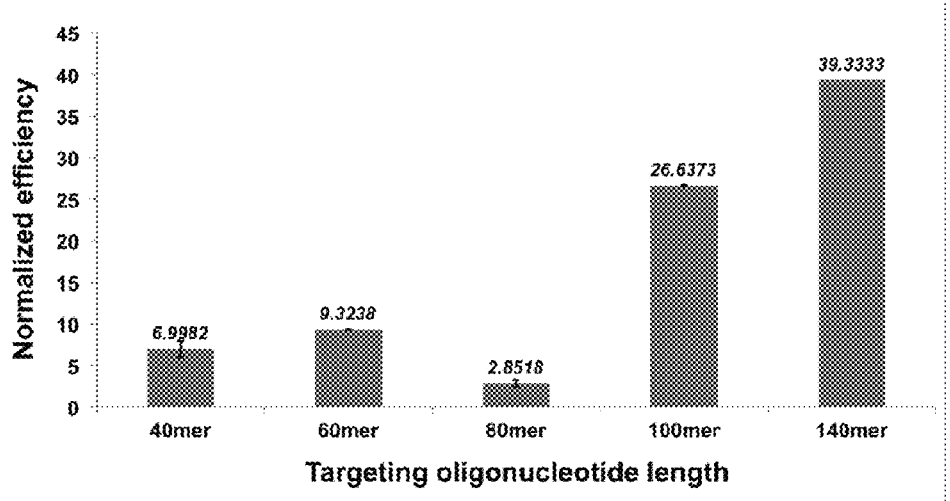

An illustration of this experimental set-up is shown in FIG. 18A. The complementary oligonucleotide is used to target the sequence of interest for creation of a DSB within the RecA-formed D-loop. If the DSB is repaired using the targeting oligonucleotide that has a single base change, the K42T ($Str^R$) point mutation will be incorporated. Experiments were done to determine the efficiency of this system in *E. coli* MG1655. FIG. 18B demonstrates that there is a 10-fold increase in streptomycin resistant cells when RecA, Ref and the targeting oligonucleotide are present (P value<0.05). Incorporation of the desired mutation from the oligonucleotide was confirmed by DNA sequencing. This indicates that the targeting oligonucleotide used to create the double-strand break can also be used as the editing oligonucleotide that incorporates the desired nucleotide change. This data establishes that the RecA/Ref system is capable of introducing a desired mutation into a specific site within the genome of *E. coli* MG1655.

In order to optimize the in vivo targeting, an experiment to determine optimal oligonucleotide length was performed. FIG. 18C demonstrates that, based on normalized efficiency, oligonucleotide length similar to that used in vitro is also best in vivo (150mer compared to 140mer, respectively). Normalized efficiency is defined as fraction of streptomycin resistant cells per total cfu for RecA/Ref cells divided by same for RecA only cells).

Discussion.

This data from the RecA/Ref system for in vivo use has confirmed that this system is able to introduce a desired mutation utilizing a directing oligonucleotide to target a specific site within the genome of *E. coli*. Many variations of this system could be implemented to bring about deletions, insertions, and point mutations. It has been shown in vitro that an oligonucleotide either missing 10 bases of homology or containing a 10 base insert still pairs with the complementary region of cdsDNA and Ref is still capable of creating a targeted DSB within the D-loop (data not shown). In addition, the results presented in FIG. 17B show that Ref is capable of cutting within two D-loops to create two targeted DSBs. If positioned on either side of a gene, this could possibly generate a whole gene deletion.

To utilize this in vivo, the flanking genomic regions would need to be joined and would require an additional repair oligonucleotide. The current procedure requires electroporating one oligonucleotide, so the system may be limited if an additional oligonucleotide needs to simultaneously enter the cell. In the original experiments, the targeting oligonucleotide is also the repair oligonucleotide, which reduces the number of components necessary, a potential advantage over other multicomponent editing systems.

In the CRISPR/Cas9 system, the guide RNA (gRNA)/Cas9 is recruited to the target sequence via base pairing with the complementary target sequence of the genomic DNA. Secondary structures within the guide RNA can lead to partially matched sequences and therefore off target cleavage. In the RecA/Ref system, the long oligonucleotide used may have secondary structures and potentially pair at off target sites. We hypothesize that since the system does not solely rely on base pairing, but rather RecA-catalyzed pairing, the oligonucleotide is less likely to pair to sequences of limited homology.

As stated previously, the CRISPR/Cas9 system uses a short RNA guide that requires a PAM, which limits potential editing targets in the genome, and the potential for off-target effects has already been established. The Ref/RecA system opens the door to the possibility of targeting any region of the genome and the substantially longer DNA guide (100-150 bases) may reduce common off-target effects via RecA-catalyzed pairing. Data gathered so far for the RecA/Ref system in vivo has not shown the efficiency required to target non-selectable genes. The targeting potential of the Ref/RecA system has already been optimized to about 80% in vitro with Ref N-terminal truncation variants disclosed herein. The optimixed RecA/Ref system has promise for becoming a useful tool in biotechnology.

In the previous Examples, we demonstrated Ref truncation variants that had increase efficiency in the in vitro targeted assay. Such variants have been shown to work in these in vitro assays as well, but further testing needs to be done with all Ref truncation variants, utilizing the same preparation of electrocompetent cells, to determine the optimal Ref truncation variant to use in the method.

TABLE 1

Sequences of oligonucleotides utilized for in vitro and in vivo targeting with the RecA/Ref system.

| | | |
|---|---|---|
| rlb1 150 mer | | TTTTGGTTTTTATCGTCGTCTGGTAAACGAGGGTTATGATAGTGTTGCTCTTACTATGCCTC GTAATTCCTTTTGGCGTTATGTATCTGCATTAGTTGAATGTGGTATTCCTAAATCTCAACTG ATGAATCTTTCTACCTGTAATAATGT (SEQ ID NO: 17) |
| AJM25 71 mer | | 56FAM/CAGAAGTAAGTTGGCCGCAGTGTTATCACTCATGGTTATGGCAGCACTGCATAATT CTCTTACTGTCATGC (SEQ ID NO: 18) |
| AJG52 71 mer | | GCATGACAGTAAGAGAATTATGCAGTGCTGCCATAACCATGAGTGATAACACTGCGGCCAAC TTACTTCTG (SEQ ID NO: 19) |

TABLE 1-continued

Sequences of oligonucleotides utilized for in vitro and in vivo targeting with the RecA/Ref system.

| | | |
|---|---|---|
| AJG53 | 140 mer | GTAGGAAGTCACTTCGAAACCGTTAGTCAGACGAACACGGCATACTTTACGCAGCGCGGAGT<br>TCGGTTTTGTAGGAGTGGTAGTATATACACGAGTACATACGCCACGTTTTTGCGGGCATGCT<br>TCCAGCGCAGGCACGT (SEQ ID NO: 20) |
| AJG54 | 100 mer | CCGTTAGTCAGACGAACACGGCATACTTTACGCAGCGCGGAGTTCGGTTTTGTAGGAGTGGT<br>AGTATATACACGAGTACATACGCCACGTTTTTGCGGGCATGCT (SEQ ID NO: 21) |
| TMO12 | 80 mer | ACGAACACGGCATACTTTACGCAGCGCGGAGTTCGGTTTTGTAGGAGTGGTAGTATATACAC<br>GAGTACATACGCCACGTT (SEQ ID NO: 22) |
| TMO13 | 60 mer | CATACTTTACGCAGCGCGGAGTTCGGTTTTGTAGGAGTGGTAGTATATACACGAGTACAT<br>(SEQ ID NO: 23) |
| TMO14 | 40 mer | GCAGCGCGGAGTTCGGTTTTGTAGGAGTGGTAGTATATAC (SEQ ID NO: 24) |
| TMO6 | | TGGTGCCTTCGTAGTGGCATTACGTATTTTACCCGTTTAATGGAAACTTCCTCATGAAAAAG<br>TCTTTAGTCCTCAAAGCCTCTGTAGCCGTTGCTACCCTCGTTCCGATGCTGTCTTTCGCTGC<br>TGAGGGTGACGATCCC (SEQ ID NO: 25) |
| TMO7 | | ATGCTACAGGCGTTGTAGTTTGTACTGGTGACGAAACTCAGTGTTACGGTACATGGGTTCCT<br>ATTGGGCTTGCTATCCCTGAAAATGAGGGTGGTGGCTCTGAGGGTGGCGGTTCTGAGGG<br>TGGCGGTTCTGAGGGTGGC (SEQ ID NO: 26) |
| TMO8 | | ATGTATCTGCATTAGTTGAATGTGGTATTCCTAAATCTCAACTGATGAATCTTTCTACCTGT<br>AATAATGTgctgagctagtaTGGTGCCTTCGTAGTGGCATTACGTATTTTACCCGTTTAATG<br>GAAACTTCCTCATGAAAAAGTCTTTAGT (SEQ ID NO: 27) |
| TMO9 | | ATGTATCTGCATTAGTTGAATGTGGTATTCCTAAATCTCAACTGATGAATCTTTCTACCTGT<br>AATAATGTgctgagctagtaATGCTACAGGCGTTGTAGTTTGTACTGGTGACGAAACTCAGT<br>GTTACGGTACATGGGTTCCTATTGGGCT (SEQ ID NO: 28) |

All publications, patents, and nucleotide and peptide sequences mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

The present invention is not intended to be limited to the foregoing examples, but encompasses all such modifications and variations as come within the scope of the appended claims.

We claim:

1. A purified engineered truncated Ref polypeptide comprising an amino acid sequence comprising a deletion of ten (10) to sixty-six (66) amino acids of the N-terminus of a naturally occurring full length Ref protein, SEQ ID NO:1, or SEQ ID NO:2, and wherein the engineered truncated purified Ref polypeptide exhibits an increased nuclease site-specific targeting activity relative to nuclease site-specific targeting activity of a naturally occurring full length wildtype Ref protein or full length Ref protein comprising the amino acid of any of SEQ ID NOs:1-2.

2. The purified engineered truncated Ref polypeptide of claim 1, wherein the amino acid sequence comprises:

(a) a deletion of the first ten (10) amino acids of the N-terminus of the full length wildtype Ref protein, wherein the amino acid sequence comprises SEQ ID NO: 10 or 11;

(b) a deletion of the first twenty one (21) amino acids of the N-terminus of the full length wildtype Ref protein, wherein the amino acid sequence comprises SEQ ID NO: 8 or 9;

(c) a deletion of the first forty-seven (47) amino acids of the N-terminus of the full length wildtype Ref protein, wherein the amino acid sequence comprises SEQ ID NO:6 or SEQ ID NO:7, (d) a deletion of the first fifty-nine (59) amino acids of the N-terminus of the full length wildtype Ref protein, wherein the amino acid sequence comprises residues 60-186 of SEQ ID NO:1 or residues 60-186 of SEQ ID NO:2; or (e) a deletion of the first sixty-six (66) amino acids of the N-terminus of the full length wildtype Ref protein, wherein the amino acid comprises SEQ ID NO:4 or 5.

3. The purified engineered truncated Ref polypeptide of claim 2, wherein the Ref polypeptide consists of an amino acid sequence selected from the group consisting of SEQ ID NO:4, SEQ ID NO:5; SEQ ID NO:6, SEQ ID NO:7, SEQ ID NO:8, SEQ ID NO:9, SEQ ID NO:10; SEQ ID NO:11, residues 60-186 of SEQ ID NO:1, and residues 60-186 of SEQ ID NO:2.

4. The purified engineered truncated Ref polypeptide of claim 1, wherein the purified Ref polypeptide is a fusion polypeptide.

5. A kit comprising: (i) the purified engineered truncated Ref polypeptide of claim 1; and (ii) a purified RecA polypeptide comprising an amino acid sequence of any one of SEQ ID NOs:12-16.

6. The kit of claim 5, wherein the purified RecA comprises SEQ ID NO:13.

7. The kit of claim 5, further comprising a targeting oligonucleotide.

8. The kit of claim 7, wherein the targeting oligonucleotide is from 60-150 nucleotides in length.

9. The kit of claim 6, further comprising a reaction buffer suitable for an in vitro nuclease site-specific targeting reaction in the presence of the purified engineered truncated Ref polypeptide of (i), the purified RecA polypeptide (ii), a targeting oligonucleotide, and a double stranded DNA comprising a target sequence to be cleaved.

10. A method for cleaving a DNA duplex within a target-defined nucleotide sequence, the method comprising:
(i) providing a complex of a RecA protein, a double stranded DNA, and a targeting oligonucleotide comprising a sequence homologous to a target sequence found within the double stranded DNA; and
(ii) contacting the complex from (i) with the purified Ref polypeptide of claim 1.

11. The method of claim 10, wherein the wherein the amino acid sequence of the Ref polypeptide comprises:
(a) one or more of the group consisting of SEQ ID NO:4, SEQ ID NO:5; SEQ ID NO:6, SEQ ID NO:7, SEQ ID NO:8, SEQ ID NO:9, SEQ ID NO:10, SEQ ID NO:11, residues 60-186 of SEQ ID NO:1, and residues 60-186 of SEQ ID NO:2; or
(b) an amino acid sequence at least 95% identical to one or more of the group consisting of SEQ ID NO:6, SEQ ID NO:7, SEQ ID NO:8, SEQ ID NO:9, SEQ ID NO:10; and SEQ ID NO:11.

12. The method of claim 10, wherein the Ref polypeptide consists of an amino acid sequence selected from the group consisting of SEQ ID NO:4, SEQ ID NO:5; SEQ ID NO:6, SEQ ID NO:7, SEQ ID NO:8, SEQ ID NO:9, SEQ ID NO:10; SEQ ID NO:11, residues 60-186 of SEQ ID NO:1, and residues 60-186 of SEQ ID NO:2.

13. The method of claim 10, wherein the targeting oligonucleotide is from 60-150 nucleotides in length.

14. The method of claim 10, wherein the method is performed as part of a genome editing process.

15. The method of claim 14, wherein the method is performed in vivo.

16. The purified engineered truncated Ref polypeptide of claim 1, wherein the engineered truncated purified Ref polypeptide exhibits an increase of at least 15% in nuclease site-specific targeting activity relative to nuclease site-specific targeting activity of a naturally occurring full length wildtype Ref protein or full length Ref protein comprising the amino acid of any of SEQ ID NOs:1-2.

17. The purified engineered truncated Ref polypeptide of claim 1, wherein the purified engineered truncated Ref polypeptide exhibits an increase of at least 20% in nuclease site-specific targeting activity relative to nuclease site-specific targeting activity of a naturally occurring full length wildtype Ref protein or full length Ref protein comprising the amino acid of any of SEQ ID NOs:1-2.

* * * * *

UNITED STATES PATENT AND TRADEMARK OFFICE
CERTIFICATE OF CORRECTION

PATENT NO. : 9,611,470 B2  
APPLICATION NO. : 14/336828  
DATED : April 4, 2017  
INVENTOR(S) : Michael Matthew Cox et al.

It is certified that error appears in the above-identified patent and that said Letters Patent is hereby corrected as shown below:

In the Specification

Column 15, Line 28, "039" should be --ϕ39--.

Signed and Sealed this  
Twentieth Day of November, 2018

Andrei Iancu  
*Director of the United States Patent and Trademark Office*

SEQUENCE LISTING

```
<160> NUMBER OF SEQ ID NOS: 30

<210> SEQ ID NO 1
<211> LENGTH: 186
<212> TYPE: PRT
<213> ORGANISM: Bacteriophage P1

<400> SEQUENCE: 1

Met Lys Thr Ile Glu Gln Lys Ile Glu Gln Cys Arg Lys Trp Gln Lys
1               5                   10                  15

Ala Ala Arg Glu Arg Ala Ile Ala Arg Gln Arg Glu Lys Leu Ala Asp
            20                  25                  30

Pro Val Trp Arg Glu Ser Gln Tyr Gln Lys Met Arg Asp Thr Leu Asp
        35                  40                  45

Arg Arg Ile Ala Lys Gln Lys Glu Arg Pro Pro Ala Ser Lys Thr Arg
    50                  55                  60

Lys Ser Ala Val Lys Ile Lys Ser Arg Gly Leu Lys Gly Arg Thr Pro
65                  70                  75                  80

Thr Ala Glu Glu Arg Arg Ile Ala Asn Ala Leu Gly Ala Leu Pro Cys
                85                  90                  95

Ile Ala Cys Tyr Met His Gly Val Ile Ser Asn Glu Val Ser Leu His
```

-continued

```
                100                 105                 110
His Ile Ala Gly Arg Thr Ala Pro Gly Cys His Lys Lys Gln Leu Pro
            115                 120                 125

Leu Cys Arg Trp His His Gln His Ala Ala Pro Ala Glu Val Arg Glu
            130                 135                 140

Lys Tyr Pro Trp Leu Val Pro Val His Ala Asp Gly Val Val Gly Gly
145                 150                 155                 160

Lys Lys Glu Phe Thr Leu Leu Asn Lys Ser Glu Met Glu Leu Leu Ala
            165                 170                 175

Asp Ala Tyr Glu Met Ala Asn Ile Met His
            180                 185

<210> SEQ ID NO 2
<211> LENGTH: 186
<212> TYPE: PRT
<213> ORGANISM: Bacteriophage phi W39

<400> SEQUENCE: 2

Met Lys Thr Ile Glu Gln Lys Leu Glu Gln Arg Arg Glu Trp Gln Lys
1               5                  10                  15

Ala Ala Arg Glu Arg Ala Ile Ala Arg Gln Arg Glu Lys Leu Ala Asp
            20                  25                  30

Pro Ala Trp Arg Glu Ser Gln Tyr Gln Lys Met Arg Asp Ser Ile Asp
        35                  40                  45

Arg Arg Ile Ala Lys Gln Lys Glu Arg Pro Pro Ala Ser Lys Thr Arg
    50                  55                  60

Lys Ser Ala Val Lys Ile Lys Ser Arg Gly Leu Lys Gly Arg Thr Pro
65                  70                  75                  80

Thr Ala Glu Glu Arg Thr Ile Ala Asn Ala Leu Gly Thr Leu Pro Cys
                85                  90                  95

Ile Ala Cys Tyr Met His Gly Val Ile Ser Glu Glu Val Ser Leu His
            100                 105                 110

His Ile Ser Gly Arg Thr Ala Pro Gly Cys His Lys Lys Gln Leu Pro
            115                 120                 125

Leu Cys Arg Trp His His Gln His Ala Ala Pro Ala Glu Val Arg Glu
            130                 135                 140

Lys Tyr Pro Trp Leu Val Pro Val His Ala Asp Gly Val Val Gly Gly
145                 150                 155                 160

Lys Lys Glu Phe Thr Leu Leu Asn Lys Ser Glu Met Glu Leu Leu Ala
            165                 170                 175

Asp Ala Tyr Glu Met Ala Asn Ile Met His
            180                 185

<210> SEQ ID NO 3
<211> LENGTH: 140
<212> TYPE: PRT
<213> ORGANISM: Artificial Sequence
<220> FEATURE:
<223> OTHER INFORMATION: TMO hybrid Ref protein

<400> SEQUENCE: 3

Ile Asp Arg Arg Ile Ala Lys Gln Lys Glu Arg Pro Pro Ala Ser Lys
1               5                  10                  15

Thr Arg Lys Ser Ala Val Lys Ile Lys Ser Arg Gly Leu Lys Gly Arg
            20                  25                  30

Thr Pro Thr Ala Glu Glu Arg Ile Ala Asn Ala Leu Gly Ala Leu
        35                  40                  45
```

```
Pro Cys Ile Ala Cys Tyr Met His Gly Val Ile Ser Glu Val Ser
    50                  55                  60

Leu His His Ile Ser Gly Arg Thr Ala Pro Gly Cys His Lys Lys Gln
65                  70                  75                  80

Leu Pro Leu Cys Arg Trp His His Gln His Ala Ala Pro Ala Glu Val
                85                  90                  95

Arg Glu Lys Tyr Pro Trp Leu Val Pro Val His Ala Asp Gly Val Val
            100                 105                 110

Gly Gly Lys Lys Glu Phe Thr Leu Leu Asn Lys Ser Glu Met Glu Leu
        115                 120                 125

Leu Ala Asp Ala Tyr Glu Met Ala Asn Ile Met His
    130                 135                 140

<210> SEQ ID NO 4
<211> LENGTH: 120
<212> TYPE: PRT
<213> ORGANISM: Bacteriophage P1

<400> SEQUENCE: 4

Ala Val Lys Ile Lys Ser Arg Gly Leu Lys Gly Arg Thr Pro Thr Ala
1               5                   10                  15

Glu Glu Arg Arg Ile Ala Asn Ala Leu Gly Ala Leu Pro Cys Ile Ala
            20                  25                  30

Cys Tyr Met His Gly Val Ile Ser Asn Glu Val Ser Leu His His Ile
        35                  40                  45

Ala Gly Arg Thr Ala Pro Gly Cys His Lys Lys Gln Leu Pro Leu Cys
    50                  55                  60

Arg Trp His His Gln His Ala Ala Pro Ala Glu Val Arg Glu Lys Tyr
65                  70                  75                  80

Pro Trp Leu Val Pro Val His Ala Asp Gly Val Val Gly Gly Lys Lys
                85                  90                  95

Glu Phe Thr Leu Leu Asn Lys Ser Glu Met Glu Leu Leu Ala Asp Ala
            100                 105                 110

Tyr Glu Met Ala Asn Ile Met His
        115                 120

<210> SEQ ID NO 5
<211> LENGTH: 120
<212> TYPE: PRT
<213> ORGANISM: Bacteriophage phi W39

<400> SEQUENCE: 5

Ala Val Lys Ile Lys Ser Arg Gly Leu Lys Gly Arg Thr Pro Thr Ala
1               5                   10                  15

Glu Glu Arg Thr Ile Ala Asn Ala Leu Gly Thr Leu Pro Cys Ile Ala
            20                  25                  30

Cys Tyr Met His Gly Val Ile Ser Glu Glu Val Ser Leu His His Ile
        35                  40                  45

Ser Gly Arg Thr Ala Pro Gly Cys His Lys Lys Gln Leu Pro Leu Cys
    50                  55                  60

Arg Trp His His Gln His Ala Ala Pro Ala Glu Val Arg Glu Lys Tyr
65                  70                  75                  80

Pro Trp Leu Val Pro Val His Ala Asp Gly Val Val Gly Gly Lys Lys
                85                  90                  95

Glu Phe Thr Leu Leu Asn Lys Ser Glu Met Glu Leu Leu Ala Asp Ala
            100                 105                 110
```

Tyr Glu Met Ala Asn Ile Met His
        115                 120

<210> SEQ ID NO 6
<211> LENGTH: 139
<212> TYPE: PRT
<213> ORGANISM: Bacteriophage P1

<400> SEQUENCE: 6

Asp Arg Arg Ile Ala Lys Gln Lys Glu Arg Pro Pro Ala Ser Lys Thr
1               5                   10                  15

Arg Lys Ser Ala Val Lys Ile Lys Ser Arg Gly Leu Lys Gly Arg Thr
            20                  25                  30

Pro Thr Ala Glu Glu Arg Arg Ile Ala Asn Ala Leu Gly Ala Leu Pro
        35                  40                  45

Cys Ile Ala Cys Tyr Met His Gly Val Ile Ser Asn Glu Val Ser Leu
    50                  55                  60

His His Ile Ala Gly Arg Thr Ala Pro Gly Cys His Lys Lys Gln Leu
65                  70                  75                  80

Pro Leu Cys Arg Trp His His Gln His Ala Ala Pro Ala Glu Val Arg
                85                  90                  95

Glu Lys Tyr Pro Trp Leu Val Pro Val His Ala Asp Gly Val Val Gly
            100                 105                 110

Gly Lys Lys Glu Phe Thr Leu Leu Asn Lys Ser Glu Met Glu Leu Leu
        115                 120                 125

Ala Asp Ala Tyr Glu Met Ala Asn Ile Met His
    130                 135

<210> SEQ ID NO 7
<211> LENGTH: 139
<212> TYPE: PRT
<213> ORGANISM: Bacteriophage phi W39

<400> SEQUENCE: 7

Asp Arg Arg Ile Ala Lys Gln Lys Glu Arg Pro Pro Ala Ser Lys Thr
1               5                   10                  15

Arg Lys Ser Ala Val Lys Ile Lys Ser Arg Gly Leu Lys Gly Arg Thr
            20                  25                  30

Pro Thr Ala Glu Glu Arg Thr Ile Ala Asn Ala Leu Gly Thr Leu Pro
        35                  40                  45

Cys Ile Ala Cys Tyr Met His Gly Val Ile Ser Glu Glu Val Ser Leu
    50                  55                  60

His His Ile Ser Gly Arg Thr Ala Pro Gly Cys His Lys Lys Gln Leu
65                  70                  75                  80

Pro Leu Cys Arg Trp His His Gln His Ala Ala Pro Ala Glu Val Arg
                85                  90                  95

Glu Lys Tyr Pro Trp Leu Val Pro Val His Ala Asp Gly Val Val Gly
            100                 105                 110

Gly Lys Lys Glu Phe Thr Leu Leu Asn Lys Ser Glu Met Glu Leu Leu
        115                 120                 125

Ala Asp Ala Tyr Glu Met Ala Asn Ile Met His
    130                 135

<210> SEQ ID NO 8
<211> LENGTH: 165
<212> TYPE: PRT
<213> ORGANISM: Bacteriophage P1

<400> SEQUENCE: 8

```
Ala Ile Ala Arg Gln Arg Glu Lys Leu Ala Asp Pro Val Trp Arg Glu
1               5                   10                  15

Ser Gln Tyr Gln Lys Met Arg Asp Thr Leu Asp Arg Arg Ile Ala Lys
            20                  25                  30

Gln Lys Glu Arg Pro Pro Ala Ser Lys Thr Arg Lys Ser Ala Val Lys
        35                  40                  45

Ile Lys Ser Arg Gly Leu Lys Gly Arg Thr Pro Thr Ala Glu Glu Arg
    50                  55                  60

Arg Ile Ala Asn Ala Leu Gly Ala Leu Pro Cys Ile Ala Cys Tyr Met
65                  70                  75                  80

His Gly Val Ile Ser Asn Glu Val Ser Leu His His Ile Ala Gly Arg
                85                  90                  95

Thr Ala Pro Gly Cys His Lys Lys Gln Leu Pro Leu Cys Arg Trp His
            100                 105                 110

His Gln His Ala Ala Pro Ala Glu Val Arg Glu Lys Tyr Pro Trp Leu
        115                 120                 125

Val Pro Val His Ala Asp Gly Val Val Gly Gly Lys Lys Glu Phe Thr
    130                 135                 140

Leu Leu Asn Lys Ser Glu Met Glu Leu Leu Ala Asp Ala Tyr Glu Met
145                 150                 155                 160

Ala Asn Ile Met His
                165
```

<210> SEQ ID NO 9
<211> LENGTH: 165
<212> TYPE: PRT
<213> ORGANISM: Bacteriophage phi W39

<400> SEQUENCE: 9

```
Ala Ile Ala Arg Gln Arg Glu Lys Leu Ala Asp Pro Ala Trp Arg Glu
1               5                   10                  15

Ser Gln Tyr Gln Lys Met Arg Asp Ser Ile Asp Arg Arg Ile Ala Lys
            20                  25                  30

Gln Lys Glu Arg Pro Pro Ala Ser Lys Thr Arg Lys Ser Ala Val Lys
        35                  40                  45

Ile Lys Ser Arg Gly Leu Lys Gly Arg Thr Pro Thr Ala Glu Glu Arg
    50                  55                  60

Thr Ile Ala Asn Ala Leu Gly Thr Leu Pro Cys Ile Ala Cys Tyr Met
65                  70                  75                  80

His Gly Val Ile Ser Glu Glu Val Ser Leu His His Ile Ser Gly Arg
                85                  90                  95

Thr Ala Pro Gly Cys His Lys Lys Gln Leu Pro Leu Cys Arg Trp His
            100                 105                 110

His Gln His Ala Ala Pro Ala Glu Val Arg Glu Lys Tyr Pro Trp Leu
        115                 120                 125

Val Pro Val His Ala Asp Gly Val Val Gly Gly Lys Lys Glu Phe Thr
    130                 135                 140

Leu Leu Asn Lys Ser Glu Met Glu Leu Leu Ala Asp Ala Tyr Glu Met
145                 150                 155                 160

Ala Asn Ile Met His
                165
```

<210> SEQ ID NO 10

<211> LENGTH: 176
<212> TYPE: PRT
<213> ORGANISM: Bacteriophage P1

<400> SEQUENCE: 10

Cys Arg Lys Trp Gln Lys Ala Ala Arg Glu Arg Ala Ile Ala Arg Gln
1               5                   10                  15

Arg Glu Lys Leu Ala Asp Pro Val Trp Arg Glu Ser Gln Tyr Gln Lys
                20                  25                  30

Met Arg Asp Thr Leu Asp Arg Arg Ile Ala Lys Gln Lys Glu Arg Pro
            35                  40                  45

Pro Ala Ser Lys Thr Arg Lys Ser Ala Val Lys Ile Lys Ser Arg Gly
        50                  55                  60

Leu Lys Gly Arg Thr Pro Thr Ala Glu Glu Arg Arg Ile Ala Asn Ala
65                  70                  75                  80

Leu Gly Ala Leu Pro Cys Ile Ala Cys Tyr Met His Gly Val Ile Ser
                85                  90                  95

Asn Glu Val Ser Leu His His Ile Ala Gly Arg Thr Ala Pro Gly Cys
                100                 105                 110

His Lys Lys Gln Leu Pro Leu Cys Arg Trp His His Gln His Ala Ala
            115                 120                 125

Pro Ala Glu Val Arg Glu Lys Tyr Pro Trp Leu Val Pro Val His Ala
        130                 135                 140

Asp Gly Val Val Gly Gly Lys Lys Glu Phe Thr Leu Leu Asn Lys Ser
145                 150                 155                 160

Glu Met Glu Leu Leu Ala Asp Ala Tyr Glu Met Ala Asn Ile Met His
                165                 170                 175

<210> SEQ ID NO 11
<211> LENGTH: 176
<212> TYPE: PRT
<213> ORGANISM: Bacteriophage phi W39

<400> SEQUENCE: 11

Arg Arg Glu Trp Gln Lys Ala Ala Arg Glu Arg Ala Ile Ala Arg Gln
1               5                   10                  15

Arg Glu Lys Leu Ala Asp Pro Ala Trp Arg Glu Ser Gln Tyr Gln Lys
                20                  25                  30

Met Arg Asp Ser Ile Asp Arg Arg Ile Ala Lys Gln Lys Glu Arg Pro
            35                  40                  45

Pro Ala Ser Lys Thr Arg Lys Ser Ala Val Lys Ile Lys Ser Arg Gly
        50                  55                  60

Leu Lys Gly Arg Thr Pro Thr Ala Glu Glu Arg Thr Ile Ala Asn Ala
65                  70                  75                  80

Leu Gly Thr Leu Pro Cys Ile Ala Cys Tyr Met His Gly Val Ile Ser
                85                  90                  95

Glu Glu Val Ser Leu His His Ile Ser Gly Arg Thr Ala Pro Gly Cys
                100                 105                 110

His Lys Lys Gln Leu Pro Leu Cys Arg Trp His His Gln His Ala Ala
            115                 120                 125

Pro Ala Glu Val Arg Glu Lys Tyr Pro Trp Leu Val Pro Val His Ala
        130                 135                 140

Asp Gly Val Val Gly Gly Lys Lys Glu Phe Thr Leu Leu Asn Lys Ser
145                 150                 155                 160

Glu Met Glu Leu Leu Ala Asp Ala Tyr Glu Met Ala Asn Ile Met His
                165                 170                 175

<210> SEQ ID NO 12
<211> LENGTH: 353
<212> TYPE: PRT
<213> ORGANISM: Escherichia coli

<400> SEQUENCE: 12

Met Ala Ile Asp Glu Asn Lys Gln Lys Ala Leu Ala Ala Ala Leu Gly
1               5                   10                  15

Gln Ile Glu Lys Gln Phe Gly Lys Gly Ser Ile Met Arg Leu Gly Glu
            20                  25                  30

Asp Arg Ser Met Asp Val Glu Thr Ile Ser Thr Gly Ser Leu Ser Leu
        35                  40                  45

Asp Ile Ala Leu Gly Ala Gly Gly Leu Pro Met Gly Arg Ile Val Glu
    50                  55                  60

Ile Tyr Gly Pro Glu Ser Ser Gly Lys Thr Thr Leu Thr Leu Gln Val
65                  70                  75                  80

Ile Ala Ala Ala Gln Arg Glu Gly Lys Thr Cys Ala Phe Ile Asp Ala
                85                  90                  95

Glu His Ala Leu Asp Pro Ile Tyr Ala Arg Lys Leu Gly Val Asp Ile
            100                 105                 110

Asp Asn Leu Leu Cys Ser Gln Pro Asp Thr Gly Glu Gln Ala Leu Glu
        115                 120                 125

Ile Cys Asp Ala Leu Ala Arg Ser Gly Ala Val Asp Val Ile Val Val
    130                 135                 140

Asp Ser Val Ala Ala Leu Thr Pro Lys Ala Glu Ile Glu Gly Glu Ile
145                 150                 155                 160

Gly Asp Ser His Met Gly Leu Ala Ala Arg Met Met Ser Gln Ala Met
                165                 170                 175

Arg Lys Leu Ala Gly Asn Leu Lys Gln Ser Asn Thr Leu Leu Ile Phe
            180                 185                 190

Ile Asn Gln Ile Arg Met Lys Ile Gly Val Met Phe Gly Asn Pro Glu
        195                 200                 205

Thr Thr Thr Gly Gly Asn Ala Leu Lys Phe Tyr Ala Ser Val Arg Leu
    210                 215                 220

Asp Ile Arg Arg Ile Gly Ala Val Lys Glu Gly Glu Asn Val Val Gly
225                 230                 235                 240

Ser Glu Thr Arg Val Lys Val Val Lys Asn Lys Ile Ala Ala Pro Phe
                245                 250                 255

Lys Gln Ala Glu Phe Gln Ile Leu Tyr Gly Glu Gly Ile Asn Phe Tyr
            260                 265                 270

Gly Glu Leu Val Asp Leu Gly Val Lys Glu Lys Leu Ile Glu Lys Ala
        275                 280                 285

Gly Ala Trp Tyr Ser Tyr Lys Gly Glu Lys Ile Gly Gln Gly Lys Ala
    290                 295                 300

Asn Ala Thr Ala Trp Leu Lys Asp Asn Pro Glu Thr Ala Lys Glu Ile
305                 310                 315                 320

Glu Lys Lys Val Arg Glu Leu Leu Leu Ser Asn Pro Asn Ser Thr Pro
                325                 330                 335

Asp Phe Ser Val Asp Asp Ser Glu Gly Val Ala Glu Thr Asn Glu Asp
            340                 345                 350

Phe

<210> SEQ ID NO 13

```
<211> LENGTH: 353
<212> TYPE: PRT
<213> ORGANISM: Escherichia coli

<400> SEQUENCE: 13

Met Ala Ile Asp Glu Asn Lys Gln Lys Ala Leu Ala Ala Ala Leu Gly
1               5                   10                  15

Gln Ile Glu Lys Gln Phe Gly Lys Gly Ser Ile Met Arg Leu Gly Glu
            20                  25                  30

Asp Arg Ser Met Asp Val Lys Thr Ile Ser Thr Gly Ser Leu Ser Leu
        35                  40                  45

Asp Ile Ala Leu Gly Ala Gly Gly Leu Pro Met Gly Arg Ile Val Glu
    50                  55                  60

Ile Tyr Gly Pro Glu Ser Ser Gly Lys Thr Thr Leu Thr Leu Gln Val
65                  70                  75                  80

Ile Ala Ala Ala Gln Arg Glu Gly Lys Thr Cys Ala Phe Ile Asp Ala
                85                  90                  95

Glu His Ala Leu Asp Pro Ile Tyr Ala Arg Lys Leu Gly Val Asp Ile
            100                 105                 110

Asp Asn Leu Leu Cys Ser Gln Pro Asp Thr Gly Glu Gln Ala Leu Glu
        115                 120                 125

Ile Cys Asp Ala Leu Ala Arg Ser Gly Ala Val Asp Val Ile Val Val
    130                 135                 140

Asp Ser Val Ala Ala Leu Thr Pro Lys Ala Glu Ile Glu Gly Glu Ile
145                 150                 155                 160

Gly Asp Ser His Met Gly Leu Ala Ala Arg Met Met Ser Gln Ala Met
                165                 170                 175

Arg Lys Leu Ala Gly Asn Leu Lys Gln Ser Asn Thr Leu Leu Ile Phe
            180                 185                 190

Ile Asn Gln Ile Arg Met Lys Ile Gly Val Met Phe Gly Asn Pro Glu
        195                 200                 205

Thr Thr Thr Gly Gly Asn Ala Leu Lys Phe Tyr Ala Ser Val Arg Leu
    210                 215                 220

Asp Ile Arg Arg Ile Gly Ala Val Lys Glu Gly Glu Asn Val Val Gly
225                 230                 235                 240

Ser Glu Thr Arg Val Lys Val Val Lys Asn Lys Ile Ala Ala Pro Phe
                245                 250                 255

Lys Gln Ala Glu Phe Gln Ile Leu Tyr Gly Glu Gly Ile Asn Phe Tyr
            260                 265                 270

Gly Glu Leu Val Asp Leu Gly Val Lys Glu Lys Leu Ile Glu Lys Ala
        275                 280                 285

Gly Ala Trp Tyr Ser Tyr Lys Gly Glu Lys Ile Gly Gln Gly Lys Ala
    290                 295                 300

Asn Ala Thr Ala Trp Leu Lys Asp Asn Pro Glu Thr Ala Lys Glu Ile
305                 310                 315                 320

Glu Lys Lys Val Arg Glu Leu Leu Leu Ser Asn Pro Asn Ser Thr Pro
                325                 330                 335

Asp Phe Ser Val Asp Asp Ser Glu Gly Val Ala Glu Thr Asn Glu Asp
            340                 345                 350

Phe

<210> SEQ ID NO 14
<211> LENGTH: 363
<212> TYPE: PRT
<213> ORGANISM: Deinococcus radiodurans
```

<400> SEQUENCE: 14

```
Met Ser Lys Asp Ala Thr Lys Glu Ile Ser Ala Pro Thr Asp Ala Lys
1               5                   10                  15

Glu Arg Ser Lys Ala Ile Glu Thr Ala Met Ser Gln Ile Glu Lys Ala
            20                  25                  30

Phe Gly Lys Gly Ser Ile Met Lys Leu Gly Ala Glu Ser Lys Leu Asp
        35                  40                  45

Val Gln Val Val Ser Thr Gly Ser Leu Ser Leu Asp Leu Ala Leu Gly
    50                  55                  60

Val Gly Gly Ile Pro Arg Gly Arg Ile Thr Glu Ile Tyr Gly Pro Glu
65                  70                  75                  80

Ser Gly Gly Lys Thr Thr Leu Ala Leu Ala Ile Val Ala Gln Ala Gln
                85                  90                  95

Lys Ala Gly Gly Thr Cys Ala Phe Ile Asp Ala Glu His Ala Leu Asp
            100                 105                 110

Pro Val Tyr Ala Arg Ala Leu Gly Val Asn Thr Asp Glu Leu Leu Val
        115                 120                 125

Ser Gln Pro Asp Asn Gly Glu Gln Ala Leu Glu Ile Met Glu Leu Leu
    130                 135                 140

Val Arg Ser Gly Ala Ile Asp Val Val Val Asp Ser Val Ala Ala
145                 150                 155                 160

Leu Thr Pro Arg Ala Glu Ile Glu Gly Asp Met Gly Asp Ser Leu Pro
                165                 170                 175

Gly Leu Gln Ala Arg Leu Met Ser Gln Ala Leu Arg Lys Leu Thr Ala
            180                 185                 190

Ile Leu Ser Lys Thr Gly Thr Ala Ala Ile Phe Ile Asn Gln Val Arg
        195                 200                 205

Glu Lys Ile Gly Val Met Tyr Gly Asn Pro Glu Thr Thr Thr Gly Gly
    210                 215                 220

Arg Ala Leu Lys Phe Tyr Ala Ser Val Arg Leu Asp Val Arg Lys Ile
225                 230                 235                 240

Gly Gln Pro Thr Lys Val Gly Asn Asp Ala Val Ala Asn Thr Val Lys
                245                 250                 255

Ile Lys Thr Val Lys Asn Lys Val Ala Ala Pro Phe Lys Glu Val Glu
            260                 265                 270

Leu Ala Leu Val Tyr Gly Lys Gly Phe Asp Gln Leu Ser Asp Leu Val
        275                 280                 285

Gly Leu Ala Ala Asp Met Asp Ile Ile Lys Lys Ala Gly Ser Phe Tyr
    290                 295                 300

Ser Tyr Gly Asp Glu Arg Ile Gly Gln Gly Lys Glu Lys Thr Ile Ala
305                 310                 315                 320

Tyr Ile Ala Glu Arg Pro Glu Met Glu Gln Glu Ile Arg Asp Arg Val
                325                 330                 335

Met Ala Ala Ile Arg Ala Gly Asn Ala Gly Glu Ala Pro Ala Leu Ala
            340                 345                 350

Pro Ala Pro Ala Ala Pro Glu Ala Ala Glu Ala
        355                 360
```

<210> SEQ ID NO 15
<211> LENGTH: 186
<212> TYPE: PRT
<213> ORGANISM: Pseudomonas aeruginosa

<400> SEQUENCE: 15

```
Glu Arg Gln Phe Gly Lys Gly Ala Val Met Arg Met Gly Asp His Glu
1               5                   10                  15

Arg Gln Ala Ile Pro Ala Ile Ser Thr Gly Ser Leu Gly Leu Asp Ile
            20                  25                  30

Ala Leu Gly Ile Gly Gly Leu Pro Lys Gly Arg Ile Val Glu Ile Tyr
        35                  40                  45

Gly Pro Glu Ser Ser Gly Lys Thr Thr Leu Thr Leu Ser Val Ile Ala
50                  55                  60

Glu Ala Gln Lys Gln Gly Ala Thr Cys Ala Phe Val Asp Ala Glu His
65                  70                  75                  80

Ala Leu Asp Pro Asp Tyr Ala Gly Lys Leu Gly Val Asn Val Asp Asp
                85                  90                  95

Leu Leu Val Ser Gln Pro Asp Thr Gly Glu Gln Ala Leu Glu Ile Thr
            100                 105                 110

Asp Met Leu Val Arg Ser Asn Ala Val Asp Val Ile Val Asp Ser
        115                 120                 125

Val Ala Ala Leu Val Pro Lys Ala Glu Ile Glu Gly Glu Met Gly Asp
130                 135                 140

Ala His Val Gly Leu Gln Ala Arg Leu Met Ser Gln Ala Leu Arg Lys
145                 150                 155                 160

Ile Thr Gly Asn Ile Lys Asn Ala Asn Cys Leu Val Ile Phe Ile Asn
                165                 170                 175

Gln Ile Arg Met Lys Ile Gly Val Met Phe
            180                 185

<210> SEQ ID NO 16
<211> LENGTH: 274
<212> TYPE: PRT
<213> ORGANISM: Neisseria gonorrhoeae

<400> SEQUENCE: 16

Ala Ile Met Lys Met Asp Gly Ser Gln Gln Glu Glu Asn Leu Glu Val
1               5                   10                  15

Ile Ser Thr Gly Ser Leu Gly Leu Asp Leu Ala Leu Gly Val Gly Gly
            20                  25                  30

Leu Pro Arg Gly Arg Ile Val Glu Ile Phe Gly Pro Glu Ser Ser Gly
        35                  40                  45

Lys Thr Thr Leu Cys Leu Glu Ala Val Ala Gln Cys Gln Lys Asn Gly
50                  55                  60

Gly Val Cys Ala Phe Val Asp Ala Glu His Ala Phe Asp Pro Val Tyr
65                  70                  75                  80

Ala Arg Lys Leu Gly Val Lys Val Glu Glu Leu Tyr Leu Ser Gln Pro
                85                  90                  95

Asp Thr Gly Glu Gln Ala Leu Glu Ile Cys Asp Thr Leu Val Arg Ser
            100                 105                 110

Gly Gly Ile Asp Met Val Val Asp Ser Val Ala Ala Leu Val Pro
        115                 120                 125

Lys Ala Glu Ile Glu Gly Asp Met Gly Asp Ser His Val Gly Leu Gln
130                 135                 140

Ala Arg Leu Met Ser Gln Ala Leu Arg Lys Leu Thr Gly His Ile Lys
145                 150                 155                 160

Lys Thr Asn Thr Leu Val Val Phe Ile Asn Gln Ile Arg Met Lys Ile
            165                 170                 175

Gly Val Met Phe Gly Ser Pro Glu Thr Thr Thr Gly Gly Asn Ala Leu
```

```
            180                 185                 190
Lys Phe Tyr Ser Ser Val Arg Leu Asp Ile Arg Arg Thr Gly Ser Ile
                195                 200                 205
Lys Lys Gly Glu Glu Val Leu Gly Asn Glu Thr Arg Val Lys Val Ile
            210                 215                 220
Lys Asn Lys Val Ala Pro Phe Arg Gln Ala Glu Phe Asp Ile Leu
225                 230                 235                 240
Tyr Gly Glu Gly Ile Ser Trp Glu Gly Glu Leu Ile Asp Ile Gly Val
                245                 250                 255
Lys Asn Asp Ile Ile Asn Lys Ser Gly Ala Trp Tyr Ser Tyr Asn Gly
            260                 265                 270
Ala Lys

<210> SEQ ID NO 17
<211> LENGTH: 150
<212> TYPE: DNA
<213> ORGANISM: Artificial Sequence
<220> FEATURE:
<223> OTHER INFORMATION: Targeting sequence.

<400> SEQUENCE: 17
ttttggtttt tatcgtcgtc tggtaaacga gggttatgat agtgttgctc ttactatgcc    60
tcgtaattcc ttttggcgtt atgtatctgc attagttgaa tgtggtattc ctaaatctca   120
actgatgaat ctttctacct gtaataatgt                                     150

<210> SEQ ID NO 18
<211> LENGTH: 71
<212> TYPE: DNA
<213> ORGANISM: Artificial Sequence
<220> FEATURE:
<223> OTHER INFORMATION: Nuclease assay sequence.

<400> SEQUENCE: 18
cagaagtaag ttggccgcag tgttatcact catggttatg gcagcactgc ataattctct    60
tactgtcatg c                                                          71

<210> SEQ ID NO 19
<211> LENGTH: 71
<212> TYPE: DNA
<213> ORGANISM: Artificial Sequence
<220> FEATURE:
<223> OTHER INFORMATION: Nuclease assay sequence.

<400> SEQUENCE: 19
gcatgacagt aagagaatta tgcagtgctg ccataaccat gagtgataac actgcggcca    60
acttacttct g                                                          71

<210> SEQ ID NO 20
<211> LENGTH: 140
<212> TYPE: DNA
<213> ORGANISM: Artificial Sequence
<220> FEATURE:
<223> OTHER INFORMATION: Targeting oligonucleotide.

<400> SEQUENCE: 20
gtaggaagtc acttcgaaac cgttagtcag acgaacacgg catactttac gcagcgcgga    60
gttcggtttt gtaggagtgg tagtatatac acgagtacat acgccacgtt tttgcgggca   120
tgcttccagc gcaggcacgt                                                140
```

<210> SEQ ID NO 21
<211> LENGTH: 105
<212> TYPE: DNA
<213> ORGANISM: Artificial Sequence
<220> FEATURE:
<223> OTHER INFORMATION: Targeting oliginucleotide.

<400> SEQUENCE: 21
ccgttagtca gacgaacacg gcatacttta cgcagcgcgg agttcggttt tgtaggagtg    60
gtagtatata cacgagtaca tacgccacgt ttttgcgggc atgct                  105

<210> SEQ ID NO 22
<211> LENGTH: 80
<212> TYPE: DNA
<213> ORGANISM: Artificial Sequence
<220> FEATURE:
<223> OTHER INFORMATION: Targeting oligonucleotide.

<400> SEQUENCE: 22
acgaacacgg catactttac gcagcgcgga gttcggtttt gtaggagtgg tagtatatac    60
acgagtacat acgccacgtt                                                80

<210> SEQ ID NO 23
<211> LENGTH: 60
<212> TYPE: DNA
<213> ORGANISM: Artificial Sequence
<220> FEATURE:
<223> OTHER INFORMATION: Targeting oligonucleotide.

<400> SEQUENCE: 23
catactttac gcagcgcgga gttcggtttt gtaggagtgg tagtatatac acgagtacat    60

<210> SEQ ID NO 24
<211> LENGTH: 40
<212> TYPE: DNA
<213> ORGANISM: Artificial Sequence
<220> FEATURE:
<223> OTHER INFORMATION: Targeting oligonucleotide.

<400> SEQUENCE: 24
gcagcgcgga gttcggtttt gtaggagtgg tagtatatac                          40

<210> SEQ ID NO 25
<211> LENGTH: 140
<212> TYPE: DNA
<213> ORGANISM: Artificial Sequence
<220> FEATURE:
<223> OTHER INFORMATION: Targeting oligonucleotide.

<400> SEQUENCE: 25
tggtgccttc gtagtggcat tacgtatttt acccgtttaa tggaaacttc ctcatgaaaa    60
agtctttagt cctcaaagcc tctgtagccg ttgctaccct cgttccgatg ctgtctttcg   120
ctgctgaggg tgacgatccc                                               140

<210> SEQ ID NO 26
<211> LENGTH: 140
<212> TYPE: DNA
<213> ORGANISM: Artificial Sequence
<220> FEATURE:
<223> OTHER INFORMATION: Targeting oligonucleotide.

<400> SEQUENCE: 26
atgctacagg cgttgtagtt tgtactggtg acgaaactca gtgttacggt acatgggttc    60

```
ctattgggct tgctatccct gaaaatgagg gtggtggctc tgagggtggc ggttctgagg      120
gtggcggttc tgagggtggc                                                 140

<210> SEQ ID NO 27
<211> LENGTH: 152
<212> TYPE: DNA
<213> ORGANISM: Artificial Sequence
<220> FEATURE:
<223> OTHER INFORMATION: Targeting oligonucleotide.

<400> SEQUENCE: 27
atgtatctgc attagttgaa tgtggtattc ctaaatctca actgatgaat ctttctacct      60
gtaataatgt gctgagctag tatggtgcct tcgtagtggc attacgtatt ttacccgttt     120
aatggaaact tcctcatgaa aaagtcttta gt                                   152

<210> SEQ ID NO 28
<211> LENGTH: 152
<212> TYPE: DNA
<213> ORGANISM: Artificial Sequence
<220> FEATURE:
<223> OTHER INFORMATION: Targeting oligoneceotide.

<400> SEQUENCE: 28
atgtatctgc attagttgaa tgtggtattc ctaaatctca actgatgaat ctttctacct      60
gtaataatgt gctgagctag taatgctaca ggcgttgtag tttgtactgg tgacgaaact    120
cagtgttacg gtacatgggt tcctattggg ct                                   152

<210> SEQ ID NO 29
<211> LENGTH: 10
<212> TYPE: DNA
<213> ORGANISM: Artificial Sequence
<220> FEATURE:
<223> OTHER INFORMATION: Edited sequence.

<400> SEQUENCE: 29
tcctaaaaaa                                                             10

<210> SEQ ID NO 30
<211> LENGTH: 10
<212> TYPE: DNA
<213> ORGANISM: Artificial Sequence
<220> FEATURE:
<223> OTHER INFORMATION: Edited sequence.

<400> SEQUENCE: 30
aggatgtttt                                                             10
```